US008404462B2

(12) United States Patent
Müller et al.

(10) Patent No.: US 8,404,462 B2
(45) Date of Patent: Mar. 26, 2013

(54) SYNTHETIC PATHWAY ENZYMES FOR THE PRODUCTION OF ARGYRINS

(75) Inventors: Rolf Müller, Blieskastel (DE); Silke Wenzel, Ahnatal (DE); Ronald Garcia, Saarbrücken (DE)

(73) Assignees: Helmholtz-Zentrum Fuer Infektionsforschung GmbH, Braunschweig (DE); Universitaet des Saarlandes, Saarbruecken (DE)

( * ) Notice: Subject to any disclaimer, the term of this patent is extended or adjusted under 35 U.S.C. 154(b) by 0 days.

(21) Appl. No.: 12/999,872

(22) PCT Filed: Jun. 15, 2009

(86) PCT No.: PCT/EP2009/057336

§ 371 (c)(1), (2), (4) Date: Mar. 14, 2011

(87) PCT Pub. No.: WO2010/000601

PCT Pub. Date: Jan. 7, 2010

(65) Prior Publication Data

US 2011/0159537 A1 Jun. 30, 2011

(30) Foreign Application Priority Data

Jul. 4, 2008 (EP) .................................... 08159743

(51) Int. Cl.
*C12P 21/02* (2006.01)

(52) U.S. Cl. ...... 435/68.1; 435/183; 435/69.1; 435/243; 435/252

(58) Field of Classification Search ........................ None
See application file for complete search history.

(56) References Cited

U.S. PATENT DOCUMENTS

| | | | | |
|---|---|---|---|---|
| 6,833,447 | B1 | 12/2004 | Goldman et al. | |
| 7,524,814 | B2 * | 4/2009 | Engelmayer et al. | 514/1.1 |
| 7,863,020 | B2 * | 1/2011 | Hamilton | 435/84 |
| 8,030,272 | B2 * | 10/2011 | Engelmayer et al. | 514/2.5 |

FOREIGN PATENT DOCUMENTS

WO WO 01/83800 11/2001

OTHER PUBLICATIONS

Florenz, Sasse et. al., "Argyins: Immunosuppresive Cyclic Peptides from Myxobacteria". *The Journal of Antibiotics*, vol. 55, No. 6, Jun. 2002.

Rachid, Shwan et. al., "Identification of StiR, the first regulator of secondary metabolite formation in the myxobacterium *Cystobacter focus* Cb f17.1", *Journal of Biotechnology*, 121(2006) 429 441.

Rectenwald, Jürgen et, al., "Nonribosomal biosynthesis of vancomycin-type antibiotics: a heptapeptide backbone and eight peptide synthetase modules", *Database Medline (online) US National Library of Medicine*, Apr. 2002.

* cited by examiner

*Primary Examiner* — Hope Robinson
(74) *Attorney, Agent, or Firm* — Greer, Burns & Crain Ltd.

(57) ABSTRACT

The invention provides the amino acid sequences comprised in or constituting the synthetic pathway enzymes participating in the production of Argyrins, as well as the nucleic acid sequences encoding the synthetic pathway enzymes participating in the production of Argyrins, as well as genetically manipulated micro-organisms containing nucleic acid sequences encoding the synthetic pathway enzymes for the production of Argyrins, e.g. for inserting one or more of these coding sequences, mutating in a targeted manner one or more of these nucleic acid sequences, in a wild type producer micro-organism or in a heterologous micro-organism, for the production of Argyrins.

6 Claims, 4 Drawing Sheets

Figure 1:
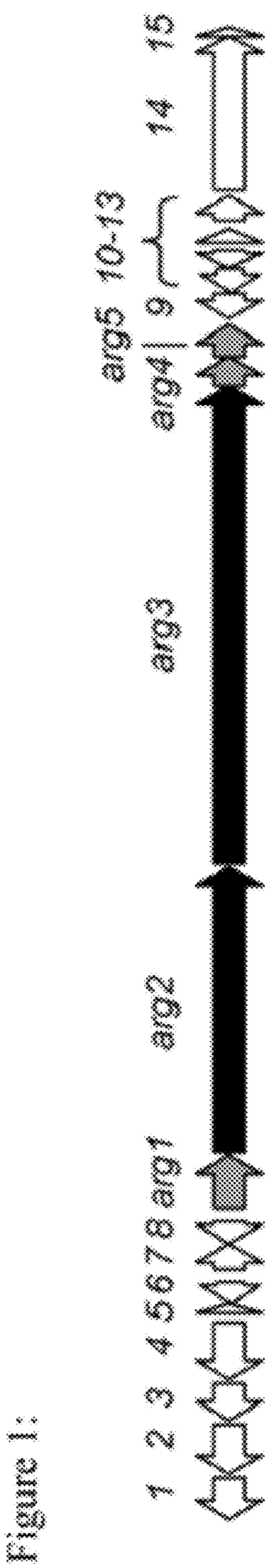

Figure I:

SEQUENCE LISTING

```
<160> NUMBER OF SEQ ID NOS: 13

<210> SEQ ID NO 1
<211> LENGTH: 55848
<212> TYPE: DNA
<213> ORGANISM: Artificial
<220> FEATURE:
<223> OTHER INFORMATION: Seq.-ID No. 1: DNA sequence comprising coding
      sequences for biosynthetic genes of Argyrins
<220> FEATURE:
<221> NAME/KEY: misc_feature
<222> LOCATION: (4)..(1608)
<223> OTHER INFORMATION: orf1: coding sequence from 1608 to 4
<220> FEATURE:
<221> NAME/KEY: misc_feature
<222> LOCATION: (3615)..(1687)
<223> OTHER INFORMATION: orf2: coding sequence from 3615 to 1687
<220> FEATURE:
<221> NAME/KEY: misc_feature
<222> LOCATION: (3661)..(5139)
<223> OTHER INFORMATION: orf3: coding sequence from 5139 to 3661
<220> FEATURE:
<221> NAME/KEY: misc_feature
<222> LOCATION: (5274)..(7388)
<223> OTHER INFORMATION: orf4: coding sequence from 7388 to 5274
<220> FEATURE:
<221> NAME/KEY: misc_feature
<222> LOCATION: (8043)..(8870)
<223> OTHER INFORMATION: orf6: coding sequence from 8870 to 8043
<220> FEATURE:
<221> NAME/KEY: misc_feature
<222> LOCATION: (8048)..(7710)
<223> OTHER INFORMATION: orf5: coding sequence from 7710 to 8048
<220> FEATURE:
<221> NAME/KEY: misc_feature
<222> LOCATION: (10282)..(9293)
<223> OTHER INFORMATION: orf7: coding sequence from 9293 to 10282
```

<220> FEATURE:
<221> NAME/KEY: misc_feature
<222> LOCATION: (10320)..(11057)
<223> OTHER INFORMATION: orf5: coding sequence from 11057 to 10320
<220> FEATURE:
<221> NAME/KEY: misc_feature
<222> LOCATION: (11545)..(13593)
<223> OTHER INFORMATION: arg1: coding sequence from 11545 to 13593
<220> FEATURE:
<221> NAME/KEY: misc_feature
<222> LOCATION: (13706)..(24322)
<223> OTHER INFORMATION: arg2: coding sequence from 13706 to 24322
<220> FEATURE:
<221> NAME/KEY: misc_feature
<222> LOCATION: (24361)..(42201)
<223> OTHER INFORMATION: arg3: coding sequence from 24361 to 42201
<220> FEATURE:
<221> NAME/KEY: misc_feature
<222> LOCATION: (42239)..(43249)
<223> OTHER INFORMATION: arg4: coding sequence from 42239 to 43249
<220> FEATURE:
<221> NAME/KEY: misc_feature
<222> LOCATION: (43309)..(44460)
<223> OTHER INFORMATION: arg5: coding sequence from 43309 to 44460
<220> FEATURE:
<221> NAME/KEY: misc_feature
<222> LOCATION: (45617)..(46507)
<223> OTHER INFORMATION: orf10: coding sequence from 46507 to 45617
<220> FEATURE:
<221> NAME/KEY: misc_feature
<222> LOCATION: (45620)..(44706)
<223> OTHER INFORMATION: orf9: coding sequence from 45620 to 44706
<220> FEATURE:
<221> NAME/KEY: misc_feature
<222> LOCATION: (46504)..(47244)
<223> OTHER INFORMATION: orf11: coding sequence from 47244 to 46504
<220> FEATURE:
<221> NAME/KEY: misc_feature
<222> LOCATION: (47547)..(47975)
<223> OTHER INFORMATION: orf12: coding sequence from 47547 to 47975
<220> FEATURE:
<221> NAME/KEY: misc_feature
<222> LOCATION: (48288)..(49268)
<223> OTHER INFORMATION: orf13: coding sequence from 48288 to 49268
<220> FEATURE:
<221> NAME/KEY: misc_feature
<222> LOCATION: (49483)..(55209)
<223> OTHER INFORMATION: orf14: coding sequence from 49483 to 55209
<220> FEATURE:
<221> NAME/KEY: misc_feature
<222> LOCATION: (55212)..(55565)
<223> OTHER INFORMATION: orf15: coding sequence from 55212 to 55565

<400> SEQUENCE: 1
gggggcctcg tggcccgtgc gtgccacgta ctccgtgtag ccaccgccgt actggtggat 60
gccctccggc gtcagctcca gcacccggtt ggacagcgcc gccaggaagt gccggtcgtg 120
gctcacgaag agcatcgtgc cctcgtagtt ggccagcgcc gtgatgagca tctgcttcgt 180
cgtcatgtcc aggtggttgg tgggctcgtc cagcaccagg aagttgggcg gatcgtagag 240
catctgcgcc agcaccaacc gcgccttctc tcctccggag agcaccttgc acttcttctc 300
gatctcatcg cccgagaagc cgaagcaccc cgccagcgct cgcagcgagc cctgcgaggc 360
cctcgggaac ttgtccacca gcgagtcgta gaccgtctgc tccggcttca gcagctccat 420
ggcgtgctgc gcgaagtagc ccatcttcac gctgccgccg agcgacaccg cgccatcgtc 480
cggccgcgac tcgcccgcga tcagcttgag cagcgtggac ttgcccgctc cgttcacgcc 540
catcacgcac cagcgctcgc ctcgccgcac caggaagtcc aggccgttgt agatgcggcg 600
cttgccgtag cccttcacca cccgctccag cttcgccacg tcgtcgcccg agcgtggcgc 660
ttgctcgaac tcgaacacca gcgtctgccg gcgcttcggc ggctccacct tctcgatctt 720
ctccagcttc ttcacccggc tctgcacctg ggccgcgtgc gaggcgcgcg ccttgaagcg 780

```
ctcgatgaac ttcagctcct tggcgagcat cgcctgctgg cgctcgtact gcgcctgctg    840
gtgcttgtcg ttcagcgccc gctgctgctc gtagaagttg tagtcgcccg agtacgtcgt    900
cagctcgccg ccgtcgatct cgatgatctt cgtcacgatg cggttcatga actcgcgatc    960
gtggctcgtc atcagcagcg cgccctcgaa gcccttgagg aacgtctcca gccagatgag   1020
cgactcgagg tccaggtggt tgctgggctc gtccagcagc atcacgtccg gacgcatcag   1080
caggatgcgc gcgagcgcca cccgcatctt ccacccgccc gacagcgccc ccacgtcccc   1140
gtccatcatc tcctcggtga acccgaggcc cgccaggatc tccctcgccc gtccctccag   1200
cgcgtacccg cccagctcct cgtagcgccc ctgcaccacg ccgaagcgct ccacgagctt   1260
ctccatctcg tccatgcgct ctggatccgc catggccgcc tcaagctgct tcagctccgc   1320
cgccacctcg gacaccggcc ccgcaccgtc catcgcctcc gccaccgccg tcttgcccgc   1380
catctcgccc acgtcctggt cgaaatagcc gatcgtcacg ccgcgatcga tggacacctg   1440
gccctcgtcc gggtgctccc gctggacgat catcttgaag agggtggact tgcccgctcc   1500
gttcggaccg accaggccta ccttctctcc cttgttgagc tgcgcagacg cctccacgaa   1560
gaggatctgc tgcccgtgct gcttgctgat gttgtcgaga cgaatcatgg gacctcagat   1620
gggggcggga taccctcacc ccgtccctct cccaggggga gaggggatgt tttcacagtg   1680
ggggagtcag gctgctccgg cggccaggtt ctgcagctcc tgccaacgcg cgtagaggcg   1740
atccacctcc gccgccgccg cgtccagatc cttctgcacc tcggccgcct tcgttccgtt   1800
ggagtagacg ctcgggtcca cgagctgcgc ttccagctcc gccttgcgcg tctccgcggc   1860
ctcgattgcc gcctccatcc cgtccagctc gcgctgatcc ttgtacgaga gtttccccgg   1920
cttgcgcgcc tgcttcggct cggccacggg cgccggctcg gccttcttcg tcgtgggcgc   1980
gggagccgcc gcggcgcgtg cctcggcctg ctccttcagc cgccggtaca tcgcgaagtt   2040
gccttcgtac cgcgtgacct tcccgtcgcc ctcgaaggcc aggatggacg tggccacctt   2100
gtccaggaag taccggtcgt gcgtcaccag cagcacgctg ccggtgaagt tcagcagcag   2160
cccctcgagg atgttcagcg tgacgatgtc cagatcgttc gtcggttcgt ccagcacgag   2220
gacgttggcg ccctccagga agagccgcgc gagcagcagt cggttgcgct cgccacccga   2280
cagcgccttc accttcatcc gctgcatggg cacggggaag agcaggtcgt ccaggtagtc   2340
gcgcagcgcc acccgttgat ctcccagctc cacccagtca tccccgcgcg gcgaggccgc   2400
ctcgtacacc gtctgctccg ggtccagcga ggcgcgcgtc tggtcgtagt acgccacctt   2460
cgtgttcttc ccgatgacca ccttgccgga gtccggcggc agctccccga gcagcacacg   2520
caggaaggtc gtcttcccca cgccgttggg tcccaccagg cccacgcgct cgccgcgctg   2580
gagcagcagg ttcacgccct tcagcacgtt ccgctcgccg taggacttgt ggacgccctc   2640
ggcctcgatg acggtgtggc ccagccgggg cgcctgcatc acctgcagtc ccgccacctt   2700
cggccgctgg aagcccttct cctccatcag cttgcgcgcc cgctcgatgc gcgccttgct   2760
cttggtgcgc cgcgcctccg ggcccttgcg cagccacgcc acttcctggg caatccagcg   2820
ctcgcgcttg tgctgggcga gggacgcgtt ctcctgggcc accagcttct gctccacgta   2880
cgcctcgtag ttaccggggt acgagatgac gcctccgcca ggctggatct cgacgatgcg   2940
gtccaccagc ccgtccagga agtagcggtc gtgcgtcacc agcagcaggg agccgggcag   3000
cttgtccagc tcctcctcga gccagtccac cgtgtccgcg tccaggtggt tggtgggctc   3060
gtccagcatc agcatgtccg gccgcgtcag cagcgcgcgg gcgatggcca cccgcttgcg   3120
cagaccgccg gagagctccg ccaccggccg gtcccactcc ttcacgccca gccggtccaa   3180
```

```
cagcgtcttc gcgtggtgct ccgtgtccca gccgccgagc tgctcgatgc ggtcggacag   3240
cgccgcgagc tgctccatca gcttttcctg gccctgggcg gacgtggact ccatgcgccg   3300
ggtgagctcg gcctgcgcgg ccagcgcttc cctcagtggc ccctgagcca cgctcaactc   3360
cgaggccacc gtggcacctg gagcgaactc gggctcctgg ggcaggtagg tgacgcgtgc   3420
cccccggcgg agctgcagct cccccgcgtc cgcgcgcgcc acccccgcca atatcttcat   3480
cagcgaggac ttgccggagc cgttcactcc cacgaggccc acgcgctcac cctcttcaat   3540
ggtgagcgtc aggccctgga agacggtacg gctgccgaag gagagttgga cgtcggcggc   3600
gcggagcagg gtcacggttg cctcgaatgc ggtacggagg tgctcgtcac ggctgcttct   3660
ttacagccac ttgggggcgc gaggcctctg ggaaacggcg ggcggtgccg ccggggcgga   3720
cgtagcggga cgggccgcct gggaagccgg ggcctgctgg ctggcgggac ggtcgctccg   3780
aggcggccga gccgactcct ggcctctgga gcctccggag ttgccaccgc ggccgttgcc   3840
accgcgccca cccccgccac gccgacggcg tcctccgaag ccctcgcggc gctcgccccg   3900
ggcctgctgt ccctgctgcc cttgtggcgc acgggggctc tgctggggcc gggccgccgg   3960
agcgggctcg agcgctccag ccacgggagc cggctggttg gagcggtgcg gatgggcctc   4020
caccaccggc acgcgccggc ggatggtgcg ctcgatgtcc ttcaggtacg cgcgctcctc   4080
ggtgtcgcag aaggagaggg cgattcccgc ggcgcccgcc cggcccgtgc ggccgatgcg   4140
gtgcacgtac gtctcgggca cgttgggcag atcgaagttg atgacgtggg tgatgccgtc   4200
gatgtcgatg ccgcgcgccg cgatgtccgt ggccaccagc acccggcagg cgccggactt   4260
gaagtccgcc agcgcccgct cgcgcgcgtt ctggctcttg ttgccgtgga tgggggccgc   4320
gccgatgccc gccgtctcca gctgcttcgc cacgcggttc gcgccgtgct tggtgcgcgt   4380
gaagacgagc acccgctcga tggccttgtc cgtctgcagc aggtggacga ggaggccgcg   4440
cttctgctcc ttctccacga agtacagccg ctgatcgatg gtctccgccg tggtggccac   4500
cggagccacc tcgacccgca ccgggttctt caggatgctg ttggccaggc cctggatctc   4560
cggcggcatg gtggccgaga agaacagtgt ctgccgctgc gtgggcagct tcgcgatgac   4620
gcgcttcacg tcatggatga agcccatgtc cagcatccgg tccgcctcgt cgaggacgaa   4680
tacctcgagc gccttgtagg acacgaagcc ctggtccatc agatccaaca ggcggcccgg   4740
agtggccacg aggatgtcca cgccctgctt gagggcctgc tcctgagcgt tctggcccac   4800
gccgccgaag atgacggcgc tggtgaggcc ggtgaagcgc ccgtaggcgc ggatgctgtc   4860
gccgatctgg gcagccagct cacgcgtggg gctgaggatg agcgagcgga tggggcgccc   4920
acgagcgggc ggcgtcgggc ggcccacgga gagccgctgg aggatgggca gcgtgaacgc   4980
cgccgtcttg ccggtacccg tctgagcgca gccgagcacg tccttgcccg cgagtacgtg   5040
cgggatggcc tgggcctgga tgggcgtggg ggaggtgtag ccctcggcct tcacggcgcg   5100
cagcagggac tcggcaagct tcaggtcttc aaaagtcatg gattctcgtt gtgggggtag   5160
tccccggagg gcccgcgcgg gaatgagccg ccgggcccga aaaaagcgaa ggcgcccccg   5220
ggggaggcgc cttccttcaa cagcctggaa ctgtcaggcc gtgcagcgcg gcattactta   5280
cgcgcggcct gctcggcggc cagcttctcc ttgtactgcg ccatcagggc ctcggcctcg   5340
ttgcgcggca ccggcgagta cttggcgaac tccatcgtga actcgccctt gccctgggtg   5400
gccgagcgga ggtccgtgga gtagccgaac atggtgttca gcggcacctc ggccaccacc   5460
gtcacgtaac cctcggccgt gctggactcg aggatggtgc cacggcgctg gttgatctga   5520
cccaccaccg agccctggaa gtcctcggga gcctggacct ccaccttcat catcggctcg   5580
```

-continued

```
aggatgatcg gcttggcggc cgcgtagccc tcgcggaagc ccatgatggc ggcggtcttg   5640
aacgcctgct cggacgagtc aaccgcgtgg aacgcgccgt cgttgatgac cacgcgcaca   5700
cccaccacgg ggaagccgat gagcgagccc ttcttgatgg cctcctggaa gcccttgtcg   5760
cacgcgggga tgaactcgcg ggggatggag ccgcccacga tgtcgtccac gaactcgtac   5820
tgctgcacgg cgtcggacgg caggggctcg acgtagccgc acacgcgcgc gaactgaccg   5880
gaaccaccgg tctgcttctt gtgcgtgtag gcgaactcgc ccttctggga gatggtctcg   5940
cggtaggcca cctgcggctt accggccacc acctcgcagt tgtactcgcg cttcatgcgc   6000
tcgatgtaga tctccaggtg cagctcaccc atgcccttga tgatcgtctg gccggactcc   6060
tcgtcacggt tcacgcggaa ggtcggatcc tccttggtga agcggttgag ggccttggag   6120
aagttggcct gggcgtcgcg gttcttcggc gccacggcga gcgagatcac cgcgtccggc   6180
acgaacatgg acgtcatcgt gtactgcacg gtgccgtcgg tgaacgtgtc gccggaggcg   6240
cactcgacgc cgaacagggc gacgatgtca ccggcacgcg cctcgttgat gtcgttcatc   6300
tcgttcgagt gcatgcgaac gagacgcggg accttgacct tcttctggtt ggcctggttg   6360
acgatgaagt cacccttgct caccttgccc tggtagatgc gcatgtaggt gagctgaccg   6420
tagcggccgt cctccagctt gaacgccagg cccacgaagg gcttgtccgg gttggactcg   6480
aggatgacct tcgcctcggc gttcttctgg tccagcgcct cgttggtgat ctccgccggg   6540
ttggggaggt aggcgcagat ggcgttgagc agcagctgca cgcccttgtt cttgtaggcg   6600
gagccgcaca tgacgggcgt catcttcagc ccgatcgtgg cgcggcggat ggcgccaatg   6660
atctgctcgt tggtgatggc ggcgtcagcc aggaacagct cgcccagctc gtcgtccacc   6720
tcggcgatct tctcgatcat ctcctggcgg tcggccttgg ccttctcgac caggtcggcg   6780
gggatggcct cctcgcggat gttctcgccg ctctcaccgt cgaagtagaa ggccttcatc   6840
tggatgaggt cgaccagacc ctggaagcgg tcctcggcgc cgatcggaac ctggaggcgc   6900
acggggtggt ggctcagctt ctccttgagc tgggcggcca cgcgctcgta gttggcgccc   6960
gcgcggtcca tcttgttgac gaacgcgatg cggggaacct tgtagcgctt catctgccgg   7020
tccaccgtga tggactggga ctgaacgccg gacacggagc agaggacgag gatggcgccg   7080
tcgagcacgc gcagggagcg ctccacctcg atggtgaagt caacgtgtcc cggggtatcg   7140
atcaggttga tgttgtactc gccccacatc gcgtacgtgg cggcagactg gatcgtgatg   7200
cccttctcac gctccaggtc catcgagtcc atcttcgcgc ccacgccatc cttgccacgc   7260
acctcgtgga tctcgtggat gcggcccgta tagaagagga tgcgctcgga gagcgtcgtc   7320
ttgcccgagt cgatatgggc ggagataccg atgttacgaa ccttttcgat gggaacttgg   7380
gtggccacga gagtcggtcc ttctgctgat tgaagtcctg cgagaacagg gcagggggcg   7440
cccttacttc ccgccgcttg aagtttccag ccaaatcggc atggagccgg ggagccgtct   7500
actccctctt agccccgagg ggaagccccc ctggctgctg ggctgctgga ggtgccctgc   7560
ctacactcgc cgttcataac catgaaagtc cccgaatact tctgtcgctc cagggaatta   7620
cggaggtaga ggaaggggca tcgcccggac ggccgtccgg caggctcaag gggtggaggg   7680
gcccgctccc cctcccgagg aggatgcaca tggcgaagcc cgctggtttc gacagggaca   7740
tcggctactt gaagcccttc ctggatcggg tcgccgccgc ggccggagag ctgacggatg   7800
ccagtgcccg agaggagctg acgcgcctca tggccgagga gaaggtgcgc tgggatcgca   7860
tccagcagct gctcgagggg gccccgggac ggagcacggc gggtggggtt tcgcccccca   7920
cgacgagtgt gggcccgcgc ccccccgccc gggcgcagga gctggcccgc gcccgcgcgg   7980
```

```
atggaatcaa ccgggtggcg ccgcgcgcgg cggggctcac cgtgggcagc ttgaagcgga   8040
agtcatgaag tcgtgacacg cgcgggggc agtgcgaaac gcagcccctc ggagatttcg   8100
gtgtcggtga ggagccggaa ggtgccctcg ggcacgtcca gctccacccc acccaccgcc   8160
tcgcggtgca gggcgcgcac cggcaacccc accgccccca gcatccgctt cacctggtgg   8220
ttgcggccct cggtgacggt cacctccacg gtgtgcgcat cacgcagccg gaccttcgcg   8280
ggccgggccg ggccgtcctc caattgcacg ccgtggcgca acggctccac cttcgcttcg   8340
tccgcctcgc tgaacaccgt ggccacgtag cgcttggtga ggtgcgtctc gggcgacgtc   8400
acgtgcgtga cgagcttgtc atcattggtg aagaggagca gcccggtggt gccccggtcc   8460
agccggccca ccgcgtgcca ggtgaagccg gccagctccg gcggcagctg gggcaggagc   8520
acctcgtaga cggtgcccac cccgtgctgg cccaccgtgg aggtgagcag ctccgccggc   8580
ttgtggaagg ccagcacccg tgtgggcgcc tcgagcgaga cgggcactcc gtccaggcgc   8640
aggctggctt ccgggggcac cggggcgagg gggtgcttca ccaccttgcc gttcaccgtg   8700
acacggccgg cctggatggc gtcctccgcc tcttcctgcg gcagcacccc ggcccgcgcg   8760
agcgcgcgtg atagccaatc cggtttggcc ttgccctccc atcgcccggg gtgggcgtgc   8820
ttggaagggg agggcgaggg ccggcgggga ggaggtggct tgcggggcat gctccgagcc   8880
actgtaacgg ccacgagtca gtgccgcgag ggttcgtcga acgcaccacc ctcggccgag   8940
ccgggcgtcg ggccgggctc accctggggc atccgccgct cctcacgctc ggtgccctcg   9000
gcggcgttgg gcgtgcgctt gggaccgttc tccttctccg cgggagcctc tcgatggggg   9060
cgcttctccg gggtgtcttc cgccgcgtcg ctgacggtca tccgctcgta gggcatgtgc   9120
cacatggttt cgctccttcc agtgtggaaa cttcaaagaa ggtagggacc tggagcgcac   9180
atcactcgga acgcttccag gtcgcccgct ggatggccgg ggggaggaga gcgcttgcgg   9240
ctgaatgctc gctcgcccag gctccccggc cccttccctg gaggacccca tggtgcgttc   9300
catcctgttg cttacccttc tcgccctgcc ggcgctcgcc gccgaaccgg ttcccgctcc   9360
ggcgccgcct cccaagcggc ccgtccacac ctattccatc gtcgcgagag atcccgagac   9420
gggtgagctg ggcgtggcgg tgcagtcgca ctggttctcg gtgggggcga cggtgccctg   9480
ggcggaggcg ggcgtgggcg cggtggccac ccagtccttc gtggatccgt cctacgggaa   9540
gctcggtctg gagttgatga gggtgggccg cggcgccccc gaggcactcg ccgggttgct   9600
ggccgcggac tccgcgagcc aggtgcggca ggtggcgatg atcgacgcga agggccgggt   9660
ggcggcgcac acgggagaca agtgcgtcgc ggccgcgggc cacatcgtgg gcgagaactt   9720
ctcggtacag gccaacatga tggagaagga caccgtgtgg ccggcgatgg ccaaggcctt   9780
ccgggagacg aagggcgacc tggccgagcg gatgctggcg gcgctcgagg cggcggaggc   9840
gcagggcgga gacatccggg gcaagcagtc ggcggggctc atcgtggtgt cgggcaaggc   9900
ctcgggacgt ccctggatgg accgcaagtt cgacctgcga gtggatgacc accccgtgcc   9960
gctgaaggag ctgcgccggc tggtgacgct gcagcgtgcc tacaatctaa tgaacgaggg  10020
agacctggcc atcgagcgca acgacacgga gggggcgctg aaggcctact cggcggcgga  10080
ggcgctggtg ccggggaacg cggagatggt gttctggcac gcggtgtcgc tcgtcaacgt  10140
ggggaaggtg gacgaggcgc tgccactcct ccagaagacg tacaaggtgg acgcacgctg  10200
gaaggaactg ctcaagaggc tgccgaagtc ggggttgctg ccggaggatc cgaagctgat  10260
gaaccggctg ttggggcgct gagccaccct ctccctctgg gagagggccg gggtgagggt  10320
catccccccc tgttccccga gcgcagccgc ttggccaacg tgtgcagggc ggcgagccac  10380
```

```
agcttcgcct ccttgcgagt gagccgggag cggcgcagcg gagcgaacaa gtcccggagc  10440
ccggtgcgcc cgcgggagtc ctcatccacg aggaaaccac cggccacgag cgcgtcctcc  10500
agagcggact ccacgagggt cagctcggtg tcggtggcgg ccacggggag cggagcggcc  10560
ggaggaggcg aggcggccag ggtggccatg cggatttcgt aggcgtacag cagcacggcc  10620
tgggcgaggt tgatggaggg ctgctcgggc gcggtgggca cggcggacag gtcgtgacag  10680
cgctcgacct cggcgttggt gagcccgctg cgctcgtcgc cgaagacgag ggccacgggc  10740
ccctgggtgg cgcgctgcac catctcctcc gccacggccc ggggagacag ccgccgtttg  10800
ccctccacct tgcgtgagct ggtgcccacc acccacacac agtccgccac ggcggcatcg  10860
agcgagtccg cgcggcccga ggcctccagc acatcctcgg cgtggacggc gagtcggcgc  10920
gcgggagcga ggtcctcggc ctcggggtgg acccaggtcc actcagacaa cccgcagttc  10980
ttcatggccc gggcggcggc acccaggttc tccgcgttac gcggacgtag caacaccagc  11040
cggatgggca gaggcatcac accgaatcct ttcagctctc acccctcgaa ctcaggggac  11100
attcacagat gcactcgcgt caaatgtctc tctttttgag aatatcgtac tttctggatc  11160
gcgatgtgtg gggcggcgct gtgatgtcta ccgtccggta ggtagctttg cctccggtgt  11220
gctgtcgcca gtgattccat tgaggatgtg tatcgatgat gttgccgttc aagaacggta  11280
catccatccg agaagattcc ctcttcgaat ctagtcgtgc tgtctttttt tgcgattgtc  11340
tcttgcccta ctgctctgtc tggtctaagt gagggtacct atggggcacc cctcctgtca  11400
gggctcaagc gcgagcctgc aagtggggtc cttacgtgcg ggcaaatggg ggggacttcg  11460
gatgaaggtt gtcgcactgc cccataagtc ccactccagt agctacgaag tcgcagtgcg  11520
cggaatccag ggatctctca ccggatttgt tgctcacgat acgcgtcccg ggcttttctg  11580
atgggccaga ccgacctact cctgctgaac gcatccaatc ttccgcagct cccgatctat  11640
ccgtatgcct tcgtgcaggt tagcgcgatc gctcgtcggt ttggcctttc tgtgcggagg  11700
ctcgatctat tgcaggtgcg ccgcgagttc tggaggccca tgctgcggga gctcatccaa  11760
cggcatcggc cccggatggt gggtatccat ctgcgccagc aggatacggt gcttcatttc  11820
gactatcaca acccacagat gggggtgatg gcggggcgct atttcccggt gcaggacacg  11880
cgggcactga ttgaggtgct tcgtgaggtg ggcgacatgc ccatcaccat gggaggattc  11940
gggttcacgt cccatgccca tctcctgctc gattatctcg gggctgactt cggggtgcag  12000
ggagatccgg atggattctt cgcccgcttc gaggacgtcg tcgcgagacg cgatctggaa  12060
tcggttccag ggctggccta tcgccgcgat ggcacctatc agttcaatcc gcgagggttc  12120
tatcctccgg cggcggagcg cgagtatacg gacgagatcg tcgatgagct gatctccttc  12180
tatggacatg ctcagctcta cggttccaac ccgccaacgg tggccgtgga ggccatgcgc  12240
ggctgcccgt tcagttgcgg tttctgtctg gagccccacg tcaagggacg ccgcatcgcg  12300
taccgcgaca tcgaaaccat cgtgagcgag ctggagttcc ttctcagccg caacctgcgc  12360
cggttctggt tcgttgcctc cgagctcaac atccaggggt cggaattcat cttgaagctc  12420
gccgagcgcg tcatccggct caacgagacc catcccggca gcccgatcga atggtccggt  12480
ttcaccctgc cacgattcaa cgagtcggat ctccggctcc tgcagcgcgc gggctacgcg  12540
ggtgctctca atgacatcct ctcgctcgat gacgaaaacc tgcaccggat gcgggttccc  12600
taccgctcgg gtcaggccat cacctatctg aaggccatgg ccaagatggc cgaggaggag  12660
agccaggcac aggccacgag tccccacggg gtggaggggc tgcgccagcg gctggcgggc  12720
tatttcaccc tgttcctggg caactcccac gccgacgagc ggaccatccg ccgctcgctc  12780
```

```
cagcaggtcg acgagcacgg cctacgcgag aagtaccgcg gggcgttcgt gatggccgcg  12840
actcgggtct acgacatcga gggcaagtac atctgcgcca cgagcgagga agaggcgaag  12900
agcatcatct cgtacgacga gcgtggtgag cgcccgttca acctgctgtg gccgtccttc  12960
tactaccctc ggttcctgat gcagcggctc ggctccacgg cggagatcct caagttcttc  13020
tcgttcgttg gagacacctt cctgtcgctc gctcatcgca tgcgcaagga ttggaactgg  13080
ttcttgtcgc ggaacacgag cgtggaacaa cttcgcgagt ggctcgccgg agcctcctcg  13140
gtgcccctcg gagcccacga ggcgccgccg catgtcctcg agaaggcggc gcacgtcctc  13200
ggagagcccc ggacgcccgc gctcgtgtcg atgatggccc cggaacccga gcagaagccc  13260
ctctggaacg aggtcgccag ggttctgctc gagcacctct tccgggtgca cggcaagtca  13320
gtggcggcgg tgaccacgca tctggggatt caggcggatg agcgtggaat tccgcgattg  13380
tcggaatacc ggctcatgga gcggctgtac caacgctacg attcagtgga gcaactcatc  13440
gaggaggcag gatcttgcct cgatgtgaca ggcgattcgc tggcgatgct ctatctgcaa  13500
tggctgctct atgccaacaa cgtcacgatt cgtcccgaat accgcgaatt gctcttcgag  13560
ccgccggtcg agcctgcttc agcggttggc tagggcatag gcagtcgtac gtctgatgag  13620
aggggccaca cggatggctt ctccgtgatt ttttcatcct cgagttccga cggtggccgt  13680
atggccgcgg agcttcgaga gaagaatgag ccgttgcgaa cagcggcttc gagatagaac  13740
gaaaatggat acgcgcaagc aggcctctgg cgaggtgtgt ttcctcgacc tctttctgcg  13800
tcaagcggag cttcatccgt cgaagtccgc ggtcgaatgc ggctcggccc ggctcaccta  13860
tcaggcgctt gtcgccagga gtgaacggct cgcatccgcg ctgggggcga gcggcgttca  13920
tccaggggat cgcgttgccg tcgtcctgca tcggggactc gacaccgtgg tcgcgatggt  13980
cgccgtgctt cggaccggtg ccgtctatgt gccgattgac gtcacctggc ccgacaaccg  14040
tatccgttac atcctcgatg acctgcagcc gggcgcgatc ctgtgtgacg aggagaactc  14100
gcggcgcgct tgcttcacga gtgatgaccg gctccttctg gcctcctccg aggggacagg  14160
gggctcggat ttcaggcctg gcccgatggc gcccgcctac ttcatgtaca cctcgggctc  14220
aacggggcga cccaagggcg tggtgctcgc tcatggcggt ctggcgagcc ggctgcatgc  14280
gttctctcgc gcatatgaga tccaacccga ggaccgcttt ctcgccctga gctcggtctc  14340
cttcgacgtg tcggtcctcg acctgatgct tcccctcgtc aatggatgct gcaccttcat  14400
tgcgtcggat gagcagcggc gcgatccgga tgcgctgcgg aacctgttcg aggagcgggc  14460
gctgaatgtc gctttcgcca cgcccaccac gatgcgcgcc ctcgtctccg tgggatggaa  14520
ggggagtccc cgcaccaaga tcctctgcgg tggtgaggcg ataccccagt cgctgatgaa  14580
cgaactcgtc gcccgggggc ggttgttcaa cgtctatgga ccgacggaag ccaccgtcgc  14640
ggtcacttcg ccagagctct tcgcgggtga cagtgtgcac ctgggccgcg cgcttccggg  14700
ggtggagttg ctcgtcctgg acgaggccgg agcgatctgt ggaccccggc agccaggaga  14760
gctcgtcatc ggcgggatcg gtgtggcgct ggggtattgg aagaatgacg agctcacccg  14820
gaagaagttc gtcgacggga agtaccggac gggcgatctc gtgagctggg gagaggacgg  14880
caatctctac taccacggtc gcatggatga gcaggtcaag ctccacggtc accgcatcga  14940
gttgctggag atcgaggaga tggcccgctc gttggggctc gtccgtgaca tcaaggtcct  15000
gattcaggag aacgcggcat cccctcggct cgtggccttc ttcatcggtg acgaggcagc  15060
cgcacaatcg ctgcggagga ggctggccag cgagcttcct gcctacatgg tgccgtcggt  15120
gtgggtcggg gtcgagggct ttccccagac gtcgaccggc aagctcgacc ggaaggcgct  15180
```

```
cctggcgaag gtcgacgagc gcgccgaggg gctcgacagt cctccggaag cggctccgtc  15240
cggcggtcgc gaggcgactc tgcttggtat ctggcgggag gtattgcagc ggccggatct  15300
gtccccggac gatgatttct tcgcgagtgg tggggattcg attctggcga tgcgcaccct  15360
gagccgggca cgcgaagcgg gaatcaacta ccgggcggtt catatcttcc agcacccgac  15420
ggtgcggagt ctgctggaga ccgtcgttca ggcgcacgaa gggcccaggc ccgaactgcc  15480
cgagttgacc acctcgggtc tgacgcccgt ccagagatgg ttcttcgagc agccgctggt  15540
caaccggggg ttctggaatc agagcattct gctccggctg acgcgcccga tggagctgcg  15600
agagctccgg gagatcgcgg actgcttgac ccggacgcat cagatcctgg cttgcgagat  15660
cgatgaaaag ggaatgcgac tgggctccag ggacgccgac gcatgctgcg cccaggtgtc  15720
cctgaccacg ggaagcggga cgtcatcccc agaatttgcc cggatcatcg acgatgcgca  15780
ccggagcctg cgccctgagg agggaaggct gcatcgcctg gtcctgatcg aatccagggg  15840
ttctggcgag tggtacctgt tctggacgat tcaccacctg gtcatcgacg gtgtgtcgtg  15900
gcggatcctc ttgagtgacc tggggaccct tctccagcag aaggccagcg gagacgcgct  15960
ccatctggag aaggcccccg tgagcttcct gcattgcagt gagcgtatgc gggcgctcca  16020
cgggaaggtg cgggaggcag agctttcgta ctggaggaag ctccccgagg cgccgttgcc  16080
ctggagctcc gaagtgcggc aggaggtgcc cgaagcggcg cggaccgagc tcgtgctctc  16140
gctctcacag gaggcgacac gcggcctgct ccaggatgtg ctggccggta cggggaaggg  16200
catcaacgat gtcctgctct ccgcgctgct ccaggccgtg tatgacgtgt ctggagagag  16260
acgcctgtca ctgtggctcg aggggcacgg gcgcgaagaa ggtctgctcg aattggatac  16320
gtccaggacg gtgggctggt tcacgtccat gttccctgtc tacctggaga gcccctcgcc  16380
ggaggacttc cagtccacgc tcgaggcgac acgcgcgtcc ctcggcgcga tgccgaaccg  16440
tggcgttggc tacggcatcg tgcgctacct gggagaggat gcgcgcggag aaggccttcg  16500
taccggcaat gagccgcgca tcagcttcaa ctatctgggc caatgggacg acgtcgccag  16560
cgaccatttc tcggtcgtga gcgaacccgg cctcgatgac atcgcgcccg agaacaagtg  16620
gcatcgagag gtggacatca actgcctcgt cgcccagggg atatttaagg tccacctgac  16680
attcgtgcgg cggctccagg acaaggagaa gctcgagagt ctgctgcgtc gcttcatcgc  16740
gcgcctggaa agcgccatcg acgcctacaa gggcgccggc gagttccggc ggaagttccc  16800
cctcctgtcg attcctcccg aggccttcgc ccgcaacggc atcgatctcc aatccgtgca  16860
agatgcctac ccgctgacgc ccatgcagga aggcatgctg ctgcgtgccc tgacggtgcc  16920
ggagagcggc aactatatcg ttcgtacctt cttcgacctc acgggagagc tccatcccga  16980
cgcctggcgg gaggcgtggc gacgggagtt ggccgagcag gaactgctgc gctccgcgtt  17040
cttctgggag cattcaccga ccccttcca ggtcgtcttc tctcacgtcg acctcgattg  17100
gcggacgcac gactggggcc acctcggccc ggaggagcag cagcaggcgt tctcgaagct  17160
ggagaaggct cgtcatgccg agggattctc cctgagcaag gcgcctctgc ttcggatcga  17220
tttcatcgcc aggggcggca gtgattacag gctcctcctg agcttccacc atttgattct  17280
cgatggctgg agtctccagg tcctcctgga gcgggtgctg aagcggtatg ggcaggcgcg  17340
aggtggcggg gaagaacggc tgactccagc atttcgtttc cgcgattacg tcgcctggaa  17400
ccgcaaccac gagtcttctg atgccctgcg gttctggcgc gagcatctcg agggggtcga  17460
ggagccgacc ctgctgggtg acgagcaggg cacccggcac gagtacgcgg aaacggtact  17520
acgtctggaa gaggcccggt ggtctgggct cggtgcccgg tgccggcggc aggggatgac  17580
```

```
caagagcagc ctgattcagg ctgtgtggtg ctgggtggcg aagtcctacg ggcggaagag  17640
ccatgtggtc tatggcttga ctcaagcagg ccgggccgcg gccatcggcg atatcgaaaa  17700
cggcgtgggc ctgttcatca ccacgagccc ggtcgcggtg gacctggaca agcattccaa  17760
gctgtccacg gtgggaagat tcatccagca ggtcaacgcc caggccctac accatgaccg  17820
gctccccctg agtgagatcc agcgcatctc ggggcgcgag atcggacaac cgctattcga  17880
ttgcctgttg gtattcgagc aggagccgat ccccgaactc gcgggaggcg tgagcggcgg  17940
cctgtcggtg gccggtactc ggacgtatga gtcaacggag taccctctga ccctgagcat  18000
cctggagaag agggatggga gctgcgatct ccgcttctat ttcaacaaga agaacttcag  18060
tgagttcagg gtagaaggac tccggcttct gttcgaggaa atccttgccg cgtgggaaag  18120
agagcaggaa ctcgagctct cttccctgcc tgccttcccg agccgggatg gcgcgcttct  18180
ctcgcggtgg aacgcgaccg ggtcggacta cccggcccaa tccctgacgg agctcttcct  18240
gcagcaggcc cggcgtaccc ccaaccaccg tgccgtgcga tacggcgagc gcgagctatc  18300
gtacgcggaa ttggccgagc ggacggggac cctggcccgg cgcctggagg cgctcggagt  18360
ccgcccccgga acccccgtgg cggtgcacat gcatcgcagc ctcgagatgg tcatcgcgct  18420
acacgcgatt gttcgagcgg gtggcgccta tgtgccgatc gatccggagt atccggcggc  18480
gcgggtgcgg acgatcctgg aggatgtggc ggcacccgtc gtcatcttcc acgacgcggc  18540
tcccttgaag tgccaggtgg gtggcaccgt tttggatgtc acccggattg tcgaggaggg  18600
tcatggcggg gcggaccacc gcgccgcgga gtatgacccc gagcggttga tgtacatcat  18660
ctacacctcg ggctccacgg gacggcccaa gggcgtcaag tgtagacacg agggggccgt  18720
caaccggatc tgctggatgc agcgaagcta cccgttgtca tccgacgacg tggtcctgca  18780
gaagaccccg tacacgttcg acgtttctgt ctgggaattc ttctggcctc tggcggtggg  18840
cgccagcctc gtggtcgcgg caccgggcgt gcaccaggac gcgagcgccc tggctgctct  18900
gatcgagcgc gaaggtgtca cacacctgca cttcgtgccc tccatgctgg atgtgttcct  18960
cgcgagcaag gggggcgctc gctgtgcctc cttgcgccgt gtcttctgca gcggagaggc  19020
attgccctcg ccggtggtca aggagttctt ccgctccgtg ccacatgcgg agctgcacaa  19080
tctctatggg ccgaccgagg cctccatcga cgtgacggcg tgggactgtc ggtccgacag  19140
tccggtggcc tcgattccca tcggctacgc gatccagaac gtgcggctcc atgtgttgga  19200
tgagaagcag gctcccgtgc cccacggtgt tccgggcgag ctctgcatcg cgggaatcgc  19260
cctggccgaa ggctatgtga accggccgga ggagacggcg aagcgcttcg tccagtcctc  19320
gtgggatgcg cgggagcgcc tctatcgcac gggcgatctg gcccgttacc tccccaatgg  19380
agccatcgaa tacctggggc gactggatca gcaggtcaag ctgcgagggt tgcggatcga  19440
gctcgatgag gtctcgagcg tgctcttgcg cgatgcccgg gtgcggcagg ccgtggtccg  19500
cgtcgtcgcg ggtcccgcgg ggcaacccgt gctggccgcc tacgtcgttg ctcacgaagg  19560
ctcggccgga acgttggagg aggcactgaa ggcggagctc gagcgctccc tgccgaggta  19620
catggtgccg gagttcttct tcttcctgga ggcgctcccg gtcaatcgca atggcaagct  19680
ggatgccgat gctctgccca ggcccggggc ctcttcctct cgggagtggg agccgcccca  19740
gaccgaggtc gagaaggatc tcgccgcgat ctggcagcgg gtgctgggtg tcgagagggt  19800
agggaggaac gacagcttct tcgccctggg gggcgattcg atcctgagca tccggatcct  19860
ggcgctcgcg aaggagcgcg gatgggacgt gagcctcggg gagttgttcc ggtctccgcg  19920
gttgagcgac ttcgccagga ccgcgaaggc ggcggcgcac acgcccgtgc tcgcgcgctc  19980
```

cgccttcagt ctgatcagcg ctcgtgaccg ggccgcgatg ccggcaagcg tggtggatgc 20040
cctccccatc gcggccctgc aagcgggaat gctcttccac acgaagctcg cggaggaagg 20100
tgtcatgtac cgcgacagct tcctctacgt cattggtggg gagttcaacg agcaggcgtt 20160
ccggcaggcg ttgaaggagt tggtgcatcg ccacccgatg ctccgcacca gtttcgagct 20220
cggtgcatac tccgagcccc tgcaacgggt ggagcgggaa gtggagttgc cgctgcggct 20280
cgaggactgg cgtgacagcc aggatcagga gcagcgtctg tcggcgtggc atgagagcta 20340
ccgcccgacg ttcgacatca ctcgagcgcc gctgttcaag atggaggtca agctcctgag 20400
cggtgccagg ttcgccctgg gtctctgctt ccaccatgca atcctggatg ggtggagcat 20460
cgcgtcgatg atgacggagc tgctcctgga ctaccagcgc ctgctgacgg gtcgtgggcg 20520
ggcgatcgag ccgctggggt ctggatacgc tgactatctg gagctggaga agcgtgtcgt 20580
cgaggatccc cagcagaagg ccttctggtc cacgtacctg aatgacgccc agtcgttgag 20640
gttgcccgtc aagcaggagg tggagcatcg gaatcggcgt ggaacgagtg tccacggccg 20700
gttcgacatt cccgaggagc tcgtcgggca gctggagcgg atcgccaggt ccctggagat 20760
caccaagagg catctgttcc tcgcggccca tttccgcgtc ctcgcgatga tctgcgggca 20820
taaggacatc gtctccgggg tcgttacgaa cggaagacca gagacggtgg acgctgaacg 20880
gatcgtcggg ttgttcctca atgcgccccc gatgcgcttg acgctcgggg gtggaagctg 20940
gcgccagctg atccaggcca tcgtcgagga ggagcggaac atccttcccc acagaaggta 21000
tccggtctcc gagatgaaac ggcattgtgt ccaggccgac ctcttcgacg tggcgttcaa 21060
ctatgtggac ttccacgtct attcgcgggc gggcgagctg gcgtcggtgg gcatccagac 21120
gctcaaggcg aaggaggtga cgaacttcgg gctgtacgtc accttctacc agggctggcc 21180
gtacagcaat cagttcacgc tggcgtatga tccggatctc ttcgaccggg agcaggtcga 21240
tcaattcgcc cggtattatc tggcggcgct gcgtgcgatg gcgcagtcgc tcgagggcag 21300
gtatgagctg tcattgctca cgcccgagga gcggtccgcg ctcctgatct ccggtgagcc 21360
acctgcctcc aagccggccc tggtggagaa gatctggagc aatgcccgtg ctcatccgga 21420
gcggcaggca ctcacggatg ggtcgcggtc cctcagctac cgggaactcg cgtcactcag 21480
cgactcgttg gctcgtgcgc tccatcaggc ggaggtgaaa cccggcgata tcgtcgcggt 21540
gaacctccgc agggacgtcc atctgccggt cgcgctcctg ggcgtgatgc gcgcgggggc 21600
cacctacctg ccgctcgaca atcgcttccc gctcgaacgg caggcgttca tgttgcagga 21660
cagcggcgcg aagctggtgc tctgtgacaa tgagacgcgc cccgcctcgg gcggaacggc 21720
ccggctcttc aatctggacg aggagaagtg gcaggaccac ggcggcgagc ggccgcttcc 21780
agagctccac gcggagtcga tcgcgtacct gatctataca tctggctcca cgggcaagcc 21840
caagggcgtg ctcatccgcc accggaatct cgacaacttc atcgcgagca tggagaggtc 21900
tcccggtttc tcccagggcg accggctgct cgcggtcacg acggtggcgt tcgacatcgc 21960
ggcgctcgag ctgttcctgc cactctcttg tggcggtcag gtcgttctcg cgccagagca 22020
ggtcggcaag gatgccacgc tgttgatgga gtggttgaag cggcacgaca tcacggtcat 22080
gcaggccact ccagccacgt ggcagcagtt cgtcgacctg ggatggcggg gcaaaccaga 22140
cctgaagatc ctcgttggtg gtgaggctct gcccccggca ctcgcccgtg ggctcttgac 22200
ccgctgccgt gagctgtgga acatgtatgg gcccaccgag accacggtgt ggtccagctg 22260
catgcggatc gcggacagca cccgtatccg gatcggccag ccgatcgcgg acacccggct 22320
ctatgtcctg gatgcctatg gaaacccggc tccccggcag accgtgggcg agctgtacat 22380

```
cgcgggcgga ggtgttgccg cgggctactg gcggcggccg gatctgaccc gtgagcgctt  22440
ccaggatgac cccttcttcg ggggtccgat gtatcggacc ggcgatctgg cgaggatcga  22500
ttcgcgcaac gaagtcgagt gcctggggcg tacggaccac caggtgaagc tgcggggtta  22560
tcgcatcgag ctcggcgaga tcgatgcggc catccaggag cacccggacg tcagtcagtc  22620
cgccgtgatt ctccggaggc actcggaacg tggtgatgag ctggccggct actacaccct  22680
gcacgatgaa gcgctctcca ggcgggcgaa tgagctctat ggagagcagg tcgtccgctg  22740
ggaggccgtc tggtcggaga cctatggccg gtcgaaggag aaccggggcg cgttgaatct  22800
ggcgggttgg aacagcagct acacgggtca acccatgccc gaagcggaga tgcgggagtg  22860
gattgacgag acggtcgcac ggattcgctc actcggcgcg aagcggatac tcgagattgg  22920
ttgcggtacg ggtctcctgc tggcccgtct ggccccccat tgcgagcggt acaccgccac  22980
cgacttctct ccggccgcgc tggagtatgt ccagagcgcc atcgtccctc agctctctca  23040
cctggactgt gaggtgcaac tggtccgcgc cacggccgac aggttggagg gggtggagga  23100
tgggcagttc gatctggtca tcctgaactc ggtggttcag tacttcccga gccgggagta  23160
cctcgacaag gtgctcgcgg cggcgatccg gaagacccgg cagccgggta ggatcttcgt  23220
gggtgatgtc aggcatttcg gcctgggccg cgcgttccat gcctccatcg ccgactacca  23280
gtccaaggga gcactggctc cggcggccct ggaggagaag gtcgcgcagg gcctgcggaa  23340
ggagacggag ctcctgttgt cgccgcgcta cttcctctcc ctgtcctctc tgggcgtcgc  23400
ccatgcggag atcgagctca ggcgggggac gcaccacaat gagttgaccc ggttccgcta  23460
tgacgcggtg ctgtccattg gccagcgtcc ggagcagctc gagacccgct ggtacgagtg  23520
ggaaacccat cctctttccg ggatgagct ctcgacgaag ttgaagcagg cgggtgagtg  23580
ctttggactc cgagccgtcg gcaacgcgcg gctggcgaga gagcgtgagc tgctgggggc  23640
tcggagtgac gagacccagg gctcagcggg agctggcgcg ggactcgatc cggagcagct  23700
ctaccggctg gcggaggctc atgggtacag ggccaagacg agctgggcct cggagcacgc  23760
ctatggcgcg ttcgatgtgg ccttcatccc ggccggaaag aacgccacgc ccctgttcga  23820
gctggcgcaa ggctcggcac gtttgagcaa tgccccttg ctctcacaga ttgatgtccg  23880
ggtgggcgcg gagatccggc gggccctcca gaagaacctc ccggagtaca tggtccccgc  23940
gcggctcgtt ctcctggatt cgatgccgca cacgcccaat ggcaaggtgg accggagcag  24000
gttgccggat gtggggcgca acgccgtctc ctccgagttc gtcgagcctc ggaacgagaa  24060
cgagcgcaag ctctgccaga tgtggcagga gttgctgggc ctggagcgcg tgggcgtgag  24120
ggacgacttc ttcgccctgg gcggccactc gctgctcgcc acacagctga tcacacgtat  24180
caacaaacag ttcgagtgca atctcagcct gcgggccctc ttcgatttcc cgacgatcga  24240
gcagctcgtc cgggagattg agcggagccg gacgctccag ggccccgcca tgccgaagat  24300
tcagcgccgc aagaagaatt agagaatccg ccaacaccgg aacagttgag agatcgagcc  24360
atgcatctcc ccgagcttct tcctttgtcg tttgctcaga cccggttgtg gttcctcgag  24420
cagttgttcc ctggccgggc cacgtaccac atccccagt tctggcgtct gcgggggggg  24480
gtgaacgtga gtgccctggt gaaggccttg aagaacacgg cggcgcgtca cgagtccctc  24540
cggaccacgt tcgtcaccga gaacggtgag ccgaggcagg ccatccacga ggacatggcg  24600
ctggacttcg agtgtgagac gctggatgag cgagggggag agacgctcga ctcctatctc  24660
tcggcgttga cggcgcggac attcagcgtc tccgaggggc cgctatggcg tgtgcggctg  24720
gtgcggacga gcgctcgtga acaggtgttg gccgtcgtct tccaccacat catctgcgat  24780
```

```
gggtggtcga tggggatctt cagccgggag gtcagccatc attacaacca ggccatcggc  24840
gaaagcttgg gtgagctgag tgagcctccc attcaattcg gagacttcgc ccagtggcag  24900
cgggagtggt tgcagggcga gcgtctggag cttcagctgt cgtactgggc ggagaaattg  24960
aagggtgccc ctgacctgct cgcgttgcca acggacttct cgcggcctcc agcggcgagc  25020
aacaagggca agctctacgg gacattcgtt cccccagagg tcgtgcagcg cctgaaggac  25080
ctggcccggc aggagaaggc caccctgttc atggtgctca tggctgcctt caaggtgctt  25140
ctccgccggt attcgggctc ggatgacatc gtcgtgggaa cgccgattgc caaccggcat  25200
tatcccgatg tcgaggaggt gttcgggtac ttcgcgaaca ccctggccct tcgcaccccg  25260
ctggagggca gcgcgagctt caggcaggtg ctgcagcggg tgaagcactc gacgctcgag  25320
gcgtatgagc atcaggacct tcccctcgag ctcgtcgtcg acaagctggg cgtggagcgg  25380
gacctgagca ggcatcccgt gttccaggtg atgttcgctc tcctgaccga aggccgctcg  25440
accctgggtg ttggcaagac ggagcttcgc ctcgaaggac tggaggtgga gagcctgcgg  25500
ggcgtcggtg attgtgccaa gttcgacctg gcgctgctcg ccgaggagac agagcagggt  25560
ctgttcctcg agttcgagta ttcgaccgac ctcttcgaac aggcgaccat cgagcgggtt  25620
gcccgccact tccagaacct cctcgtggag gtggtcgccg ggccgggatc gtcgatcgat  25680
gactacttcg tcctgagtga tgcggaaatc gccgagcgga tcgcctgtct ggatggatat  25740
ggactccccc acgacaccga gatctgtctg catcagtggg tggagcgctt cgcggcacga  25800
acgcctcagg cgatcgccct ccgggatcag acggggtcga tgacctaccg ggagttgaac  25860
gaggaggcga accggctggc gcgctgtctg ctcgagcgtg gtctgggcca tggacagatt  25920
gtcgggctcg ccctccctcg gacgagggag ctcatcgtcg cgatggtcgc ggccttgaag  25980
gcacgagcgg cctatcttcc gctggacctc ggctatccga gccagcgtct gcgcttcatc  26040
ctggaggacg cggagaccgc cgcggtcctc accacccggg cgcatgtcga gtccctgcgg  26100
gggcactgca agcacatcat cgccctggag gatgtggcgg cggaggtcgc tggccagtcc  26160
gcggggaacc tggacctgga ttacgcgtcc ggggatctgg cgtacctgat ctacacctcg  26220
ggctccacgg gcaagcccaa gggcgccacg atctgccacc gcaatgtgac gcggctcttt  26280
cccgatccgg aacctctcta ccggttccgc ccggatgatt gctggacgtt cttccactcg  26340
tgcgcgttcg atctctctgt ctgggagatc tggggcgcgt tgagccacgg ctccacgctc  26400
tccgtggtgc cagccgaggt ggctcgatcg accgacgagt tccgcgagtg gctggtcgcg  26460
catcgggtta cggtcctcaa ccagacgccc tctgcctacg agcagcttct ctcgtatatc  26520
agcagggagg gcgggagcga cgggctgcgg ctgcacaccg tgatgcttgg cggcgagggg  26580
tggggagagg ccttggcgga gcgccatcgc cagctcctac cgcatgtctc cctttacaac  26640
gagtacggtc cggcggagtg cgccgtctgg acgacacacg gctgcgtcta tgatgcggag  26700
acggtgcagt cgtatccgct ggatctgggg atcgcgcaca gccagagtct ggccctcatc  26760
ctgaacgatg gtcatcgtgt taccccgacg ggcgtcgtgg gcgagctcta cctcggcggt  26820
gagggtgtca cccaggggta ttggaagcgg ccagagctga acaaggagaa gttcgtccac  26880
gtctcccttc ccggaaaggg caacgtccgc ctctacaaga cgggcgatct cggaaggtac  26940
aagagcaacg gacgtatcga attcatcggc cggcgcgatc accaggtgaa ggtgagaggc  27000
taccggatcg agctgggtga gattgagagc atcctccgga gccttccggg tgtccgggat  27060
gcgctcgtca tgttgagcga gagcggccgt cagctcgtgg cctacgtcgt ggtgggtgag  27120
ggcgggacgc tcacgcagga gacgatcgcg taccagctca aggatgcgct gccagcctac  27180
```

```
atggtgcctt ccttcttcgt gctcctggag cgcttcccga tgacgaataa cgggaaggtg  27240
gatcgggccg ccctccccaa gccccacgcg acgacaggtc agtcggttgg ggctcaggcc  27300
ttcgtcgcac ccagcgggcc actcgaggaa ggtatcgcca gtgtgttctc cgagctgctg  27360
gcgatcaccc ccttctccgc ggagggcaat ttcttctcgt tgggtgggca ctcgctgctc  27420
gccacacagg cggcggcgaa gatccatcag cgtctgggca tcgcgtgccc ggtgcgtacc  27480
ttgttcgaga gcagcacccc gagggcgttg gcctggaagt tgggacagga gggcacgaag  27540
caggccgtgg ctggagccgc gctgcccgtg ctccagccga atgagcagga ccgtcaccag  27600
cccttcccgc tgacggacat ccaggaggcc tactggattg gccgcaaggg ggcactgacg  27660
ctcggggaag tctcggtcca ttgctacatc gagtacgaca tggacgagct ggacgtgggt  27720
cggctggagc gggcgctcaa ccgcctcgtt cagcgccacg aggccatgcg tctggtggtg  27780
gaggagagcg gacagcagcg ggtgctggaa agcgtcccct tctacaagat cgaggtgacg  27840
gagctgtccc gggggtcgcg agaggaggag gcacgtgctc tcgccagcgt gcgtgagcgc  27900
atggctcacc aggtgctccc cgcggatcgt tggccgctgt tcgagatcag ggcgagcagg  27960
gctcatggct tctggcgtct gcacgtgagc ctggatgcgc tcgtgctgga tgcctggagc  28020
ctgaatctga tcttcaatga gtgggcccgg ctctaccgcg atgaggagac ccggctcgag  28080
cccctgaacg tcagcttccg ggactacgtc atcgccgaga aggcgttcaa gagcacgcag  28140
acgtggcaga aggcgaagga ctactggctc gcacgagtcg ccacgttgcc ggatgcgccg  28200
cagttgccgc tggcgcagag ccagacacgg ctcgacgcgc agcacttcaa tcgcgagcag  28260
aagcgcctga ctcccgaggc cctgcggtca ctgcggaagc tcgcggacaa gcacaaggtg  28320
tccctgtcca gcgtcctggg cgcggtcttc gccgacgtcc tgtcactgtg gagcagcaag  28380
ccgcacttca ccctgaacat gacgctcttc aaccggctgc cggttcatga gcagatcaac  28440
gacatcgccg gtgatttcac gtcactcaat ctgctcgagg tcgactggcg cggaagtgac  28500
gtgccgttca tcgagcgcgt ccgcaaggtg caggagcaac tctggagcga cctggatcac  28560
cggttcttca gcggcgtgca ggtgctgcgt gagctggccc gggctcgcaa caacccggca  28620
gtggccatgc cagtggtgtt cacgtgcctg ctgggatcga ccgaaggga gggacaggct  28680
cacgagtggg agcgtctgtt cccgaacgag gtcttcaaca tcacccagac tcctcaggtg  28740
tggctcgact accaggtcta cgagtcccag ggcgagctgg tggtctgctg ggattatgtc  28800
gagggtctct tccccgaggg actggtgggg gccatgcacg aggcctacat caccagcctc  28860
gagaggctcc tgcgcgagga gagcgcctgg aatgagacgc gcctgacgaa tctccccgag  28920
tcccagcgaa tccggcgtga ggaggcgaac gcgacggcct ggcgtgagcc ggaactgctc  28980
atgcatcagt tgttcgagcg ccaggtcggc gtggctcccg atgcgaccgc ggtcatcgac  29040
agcgagggaa gttacaccta ccgccagttg aatgtggccg cgaaccggat cgcacgaagg  29100
ctcgcgtccc tgggtctgga gccgaacgag cgcgtcgccg tgctggcgcc gaaggggtgg  29160
cggcaggtcg tggcctgtct gggtatccag aaggctggcg ccgcgtacct gcccgtggat  29220
gggagtgcac ccgccgagcg gatcaacaag gtcctggagc ttggacgggt gagggccgct  29280
gtcgtcgcgt ctctcgagta cggcggggcg ttcggaagca atgccctcat cgtcctcgat  29340
gacgggctgc tggcgcccgc ttccggaacg gaggatgtga gcaatccggc gccgaagcag  29400
accttggcgg acctcgcgta tgtgatcttc acctccggtt cgacgggaac acccaagggc  29460
gtgatgatcg atcaccgggg ggcggtgaac accctcctgg acatcaacga gagattcggc  29520
gtgcgccagg atgacagggt gctcgcgctc tcgagcctga ctttcgacct gagcgtctac  29580
```

```
gacatcttcg ggttgctggc cgctggtgga gcggtcgtca ttcctcccga ggcccatgtc  29640
aaggagccgg cggagtggtg tcactggctc gtccagcacc aggtgaccgt gtggaacacg  29700
gtcccgatgt tcatgcagat gctcatggag ttcgtgggcg cactgccagt ggccgaacgg  29760
gaggcgctct cgcggacgct ccggctggtc atgatgagtg gcgactggat tcccgtcgag  29820
ctgccgaaca cgatcaagcg ggtcttccaa cgcgaggacc tgcgggtgat gagcctcggt  29880
ggcgccacgg aggcgtcgat ctggtcgatc gcctacgaga tcaaggacgt cgcgaaggac  29940
tggacgagca tcccgtacgg gaagccgctg cggaatcaga ccttccatgt cctggacgaa  30000
gggatgcgtc ctcgtccgga cttcgtgcca ggccagctct acatcggcgg catgggcgtc  30060
gccctcgggt acttcggaga cgaggcgaag acagccgcga gcttcctccg ccatccccac  30120
accggagaac ggctctatcg gaccggagac ctcgggcgct acctggccga cgggaacatc  30180
gagttcctcg gcagagagga tctgcaggtc aaggtgggtg gccaccggat cgagctcggt  30240
gagatcgacc accatctgca caagtgcgga tggatccgtc aggggttgac gcacgtcttc  30300
aagcccgatg gcaggaaccc gcagctcgtc gcctacctgg ttcccgaggg agtgacaggc  30360
aagagcgagc aggagcgtgc ggaagagctc tcgttcaagc tggccgggca caacctcagg  30420
aagacggggg gcgcgggcca tcggctcgtg acggagctcg aacccaaggt ctacttccag  30480
cgcaagagct atcgcgtgtt cgccggagag gagtcccggt tgagccagct ggaggcgtgg  30540
ctgcggagcg cgctgctccc gggcaagcct ctcgcgacgg agcggcggga atggacggtg  30600
gcggagatgc tcgcgccgct gctggctctt cgtgaggacg gcctgctgct gccgaaatac  30660
cgctacggtt ccgcgggctc gctctacccg gttcagacct acctcgtcat gggagagggg  30720
cggaaggagc tcgcccccgg cgtctattac ctcgaccccg tgaagcacga gctggtgcgt  30780
ctcgcggacg gcgcgctggc ctgctcctgg ttgagccggc gaggtgttcc cctggcgctg  30840
tgcttcgtcg agaagcgctc ggcgatcgaa cccctctatg gcacgcgcag tgacctctac  30900
agcgccatcg aggccgggag catggcggcg ctcgtcgcct cctcgaccgc cgcggccggc  30960
atttcgtggc ggacccggtc cgcaccagac ctggaggaac tggcgcccgt cgtcctggag  31020
tccgctgact gctccgcgat cgcggtcctc gagccccgcg agctccaggc cctcgacgag  31080
cgcggcaagg actccgatgt ctccgtcctg atgtacgtga tgcgagggtc ggagcatggc  31140
ccacggacgg gttggtaccg ctggtccggg gaccacttcg aggccttcag tgctccggcg  31200
ctcagcatgg tgccgtcgaa ccccgcgaac tggtccatct gccagaatgc gtccttcgcg  31260
ctcttcgtga tggagggaaa ggcacagccg cggacctcct cggcgctctt cacggggcgt  31320
ctgatccagt ccttgatgga gaaaggcgtg gggctgggcc tgggtggctg ctcgatcgga  31380
gaaatggacc ccgagggcgg gcggctcctg agagaagtgc atgacggtga gttcgttcat  31440
gccttcttcg gtggaccggt ggattccgcc cagatctccg cggtgggcac ttccgaggcg  31500
gagccgttcg agcaactcgt gaagcggaag acgcgctcgg tcctcgaggg ctcgcttccc  31560
gggtacatgg ttcccgacca ctacgtcctg ctcgacagct tccccctgtc gagcaatggc  31620
aaggtcgatc gttcccggct cgccgccccg gagttggaga gaccccagaa gcaagacgcc  31680
ctggtgcggc cctggaacag caccgaggcg gtcatcgcga gcatctgggc gcagttgttg  31740
ggcgtggagc cggacgcggc cgacaacttc ttcgcgctgg gcggccattc gctgaccgcc  31800
acgcagctct gtacgcgtct gcgagaggcg tttggcgtag aggttcctct gcgcgaggtc  31860
tttggtaggg cggatgtgcg gtcccaggcc agcatggtcg agggcctgct gaaacagcac  31920
gtcggtcgtg gggcttcgat tccccgcaga gccgggacgg gccggtccgt ggcgtcgtat  31980
```

```
gcgcagaagc ggctctggtt cgtcgagcaa ctggcggaga acggttcggt ctacggaatg  32040
ccggtcgcgg tcgcgctcca gggccccatg gactgggatg ccttcaagaa ggcgctcgcg  32100
ggggtcgtgg cgcggcatga aatccttcgt acgaccttcc acatggagca gggggagttg  32160
tggcaggtga tccacgagga gatcaccgcc cccttcgaga cggagcagtg ccccgagggc  32220
tccgtgatgg agaagcgcgc gtatgtgcgg aagcggatgc gcgagctggc gcgggtgccg  32280
ttcgacttga gcaccggtcc gctgctccgg ttccatgcgt tcgcgctgtc cagggagcag  32340
cacatcctgt tcggcgcgat gcaccacatc atctccgatg gctggtccgt ggatgtcttc  32400
cagtcggagt tgagcgctct ctacaacgcg gcgctgagcg ggagcacgcc ccagttccag  32460
gagctctcca tccagtacgc ggatttcgcg gcctggcagc gggattggct ccgtgggccg  32520
cgctccgaga agcagctcca gttctggaag gactccctcg cgggtgctcc ggagctcctc  32580
caactcccca ccgatctccc caggcccgaa cgtcagagct tccgcggtgg cgtggttcgc  32640
aggacgctcg atgcgcagtt gaccgcggag atcgactcgc gctgccgtga gtggggcgtc  32700
accccccttca tgttctatct cgcggcctac aaggtgcttc tgtccaagct gagtggacag  32760
gcggacattc tcgtgggcac cccggccgcg aaccggcact actcccaggt cgaacgcctg  32820
attggttact tcgcgaacac gctggccatc cggagccgcg tcgaggggca gcggagcttc  32880
gccgagtatg tccaggcggt tcgtgaagga gtgctggcgg cgaacgagaa ccaggacgtt  32940
cccttcgagc aggtcgtcga gagcctccag cttcgtcgca gtctggcgta ccagcctgtc  33000
ttccaggtca tgttcgtgtt cgagaacgag gggcgctcca gcctttcgtt gaacggcgtg  33060
agcgtgcagc cggtatccct ggacgcgcag gtcgcgcgct tcgatctgac gctgctcatc  33120
cgcaacgcgg gagacgcacg ggagatctcc ttcgagtatt cggaggacct gttcaagcgc  33180
gaaacggccg ctgaatggct cgatggagtc atcagcctgg tggaagccgc gacgcgggac  33240
agcagccagc ccctggccgc gctgccctcg atgtccgagg ccacgctgga gaaggtcctc  33300
ggccagttca gccggggaga gcgcacggcg agccccaagc tgtgtctgca tgagcagttc  33360
gagcgtgtgg tggcccggca gggagagctc tgcgccattc aaacgcctcg cagtgagatc  33420
acgtacgagc agctcaacga cagggcgaac cgcgtggcgc gtctgttgtc ctcgcatggg  33480
atccgcaagg gggacgtggt cgcgctctgt ctgaagcgct cgccggatct gttcgcctgt  33540
tacctggcgg tgctcaagct gggtgcggtg tatgtggcca tcgatgggga gtacccggaa  33600
cgccggatcc agcacatgct gaccgacgcg ggcgcgaagc tcgtcgtggc ctccccccgtc  33660
tatgcggaca agctgggaac ggccccggtc ctcgtgacgc tggaggagtg tgaggaccgg  33720
ctggagtcga tggcgggctc caacctctcc gtcaaggtct ccccggagga tgtggcgtac  33780
atcatctaca cctcgggaac gaccggtctg cccaagggcg cgcgggtcaa gcatcgcggt  33840
gtctccaacc tcgtgctcgc gcagcaggag tacttcgtgg cggggcccgg aaagcggctc  33900
ctgcaattcg cctcgtgcag cttcgacggg gccatctggg agtggacgac cgcgttgctc  33960
aacggcgcga ccctctgcct cgtcgcggag agcagcgccg aggtcgtcag ccgcctcacc  34020
cgccgcgacg agcagccgcg gatcgacatc gccgccctgc ctccgtccgt ggtcgccagc  34080
cttccggacg attgcctgcc agggctcgag gtgctgctgg tcgcagggga gagctgcccg  34140
cggggtgtgg tggaccgctg gtctcggcgt acgcggatgt tcaacgccta tggcccgtgt  34200
gaagccagtg tgacgtcgac gatgttcgag ttcgatggca ctcgcggtgc gtcgaccatc  34260
gggcgtcctc tgcgcaactg cgatgtctac atcctggatg agcggatgct ccctgtccct  34320
ccaggagtgg ccggagagct ctgcatcgcg ggactgggac tcgcggaggg gtaccacaac  34380
```

```
cgggcggagg agacggagcg gcggttcgtc gaggcgagca tcggctcgga gaccgtgcgg  34440
atgtaccgca cgggtgatcg tgggcgttgg gcgagcgacg ggaacatcga gttcctgggc  34500
cgcctcgaca atcagatcaa gatccgcggg attcgcgtgg aaccggatga ggtccgcacg  34560
cagctcctcc aggtgcccgg tgtggcccag gcggctgtcg tcgtcgatcg ggaggggcag  34620
gagacgcggt tgctcgcata cgtcgtggcc tcgccggagg tcccgctcga cctggagcac  34680
gtgcgcaaac ggctacgggc cgcgctgccc gaggccctgg ttccctcgtg gttctgcccg  34740
gttgctacgc ttccgatgac gctcaatggg aagctcgatg tggaggccct tcccaggcca  34800
ggcgaggagc ggaccgaagc gcggttcgaa gagggtgcca cggaggtgga gcggaagctc  34860
caggccctca tcgcgggcgt gctggagggc aggcggctcg gccggcacga cgacttcttc  34920
cgaaacggag gtcattcgct caaggcgatc catctcgtcg cggagatccg gaaggaactc  34980
ggtgccgagt tggcggtgaa gaccatcttc gacgctccga cagtggccga gctggcccgg  35040
gtgatcgaat ccgaaagaag acaggaaggt ccgaccgcct cgcgtccccg cctggagggc  35100
tcccggttca cgctgtccgc cctgcagcgg cagatgtggc tggccgagaa ggtgttgcag  35160
cggagcggcg cctacaacat gccgctctgc ctggagcttc gtggcgcgcc ggatgcttcc  35220
gccctgcaga acgccgtcga catgctcctg cagcggcatg gtgtcttgcg gtggcagttc  35280
aaggaggagt cgggcgagcc ctatgcggag gattgtggcg tcgacacggt gacgctcgcc  35340
acgctcgact ggagggagct ggggcagcag gagaaggaca ccgcactcgc cgggctcatc  35400
gcgacgccgt tcaacctgtc tcaggggcct ttgtggcggg gcgcgctcat ccgaatcgga  35460
gaggagcgct tctggctcct gctctgcgcc catcacctgc tggcggatgg atggtcgctg  35520
ggactccttc tcggagagct ggccgagctc tacaacgcgc gagtaggtca tggcacggcc  35580
cggttgccgg cgcctggcac cgagtactcc cgctatgtcg agcagagtgt cggggatgag  35640
cgggagctcg agcgtcaact cgagttctgg cgtcatcagc tcgagggtgc tccgcagcgg  35700
ctggcgttgc ccatggagtt gaagcggtcc ctgtcacccg gaaaggccgg tgccgtcgac  35760
ttcgaggtgg gtccggagct gaccgctcgt ctccgtgagc tggcggaaca gcggggcagc  35820
agcctcgtca tggtgctcat gagcacgtat caggccgtgc tcgcccggtt cgcgggcgcc  35880
gatgacgtgc tcatcggaac gcctgtcgcg tgccggcaca agccggagct gttgaacacg  35940
atcgggctcc tggtgaatac cctccccatc cgtttgagcc tcaccccgcg tacgacattc  36000
gccgaggcgc tcgcgcaggt ccggcagcgg ttgctcgagg ggatggctca catggacgtt  36060
cccttcgagc gcatcgtctc cgcggtcgca caggagcgcg agcccggtgt ccccgcgctc  36120
tgtcaggcga tgttcgtctg ggaggagggc gctcgtggtg acctgaagct tcggggtctc  36180
gacgtctcac tgaaggcgac cccggtcacc tccgcgaaat acgacctcgc cctcttggcg  36240
agcgaacagg acggccgtgt cacggggcgg ctcgagtatc ccgaggggct ctatgaccgg  36300
gcatccgtgg agcagctcgc cctcagctac gtgaagctgc tctccgagat ggcgaaggat  36360
ctggagggga tcgtcgcgca ggccgagctg atgtcccagg agcagcggcg gcaattggag  36420
gcgtggttcg agtaccggcc ggagttcctc gaggctccca acctccacac gctgatcgag  36480
cgtcaggcgg ccaccgcgcc cgcgtcgtca gcgctgcgct acaagggtga gagctacagc  36540
tacgagtggt tgaataccca ggccaataga ctggcgcgct acctcggggc tcggggcatc  36600
gggcgcggca gcgtcgtcgc gctgtgcctc gcgcgctcgc cggagctcgt ggtcgcgtgg  36660
gtggccgtgc tcaagtccgg ggcggcgttc gtctcgctcg atccccatat gcctcaggcc  36720
aggaggcggt tcatcctgga tgacagcagg accgcgctcg tgctgtcgca cgccgccttc  36780
```

```
gcggaggagc tcgggaccgg tacggacatc gccgtctggg aagaggtggc gaagcagctg  36840
accgggctcc cggcggagaa cctggagctg gaggtccgtc aggaggagct ggcgtacctc  36900
atctacacct cggggaccac gggcaatccc aaggggacca tgctggcgca ccgggggatg  36960
atcaacctgg cggtcagcga gaagcagcgc agcggaatgg gtcctcagag caaggtcctc  37020
cagttcacca ccgccacctg tgacggttcg atctgggagt ggacctcggc cctggtgaat  37080
ggcgccgagc tctggctgtt ggatgcgagc aatccgcagg agcaggtggc tcaggccatg  37140
caactcctgt cggagcctgg gattaccacc gtcgcgctga cgccgagtgt ggtggagctc  37200
ctccccccgg aagcgatgcc cacggtgcaa tcactcaccc tggcgggtga ggcttgcccg  37260
ttggcgctgc tggagaagtg gtccgcgagg atccccggag tcgccaacgt ctatggtccg  37320
accgaagcaa cggtgaccac ggccacattc cccttccggc ccggctatcc cgcgaacacc  37380
atcggcaagc cgctggcgaa cgtgcaggtc tacatcctgg atgagcacgg caagctgctc  37440
cctccaggcg tcatcggcga gctctgcatc gcgggtgtgg gtctggctct gggctatctg  37500
gatcgcgacg agctgacaca acggaagttc gtcacccatc cgattggacc tcgaggcgag  37560
cccgttcgcg tctaccgctc gggtgacctg gcccgctatc tgccggatgg ccatatcgtg  37620
ttcgagggcc gcagggacaa tcaggtcaag gtgcgaggct atcgcgtcga gctggatgag  37680
gtggcctggg tcctcaagca gcacccgcag gttcagcagg cctcggtgat cgtctcgcag  37740
gccgggaagc ggtatccgta tctcgttgcc tacgtcgtgc cgcgcacccc gccgtcttct  37800
ccggccagcc tgcgggcgga gctgcgtgcg tacatggccg agcggttgag ccactacatg  37860
gttccggagg cctacgtctt catcgagtcg ctgccgctca atcgctccag catgaaggtg  37920
gaggtctcgc tgctgcctcc tcccgagggg gactccttcg ttcgtgacac gctggtgccg  37980
ccagagacgg ccgtggagaa ggagctggcc accctgtgga tggagctcct cggtgtgggg  38040
agcaccggcc gtcatgacag cttcttccgg ctcggcggca actccctgct cgccgtcaag  38100
ctgggtcacg ccatcggcga gcggtggggt tgtgacatct ccctcccacg tatcttcgag  38160
aacgacacgt tggcggcgct cgcgcggtgc atcgaggccg acgagagaag gagccatgac  38220
ctccagctcg ccagggccag tgagcgcgag agctggcccc tctcttttgc tcagggacgg  38280
atgtggttcc tcgagcatct gacccagggg agctccgcct accacgtgcc actcgtcctc  38340
cggctcatcg gcaaggtctc gttcgagcgg ctcgcccagg ccttgagcgc gttggtggtt  38400
cgccatgagg tcctgcgcac cgcctatgtc gaagacggga acacgctgag ccagaagatc  38460
ctcgacgccg ttgccgtcga gatggcgagc agcgacctga gcccgatcgc tcccagtgaa  38520
cggcaggcgg ccgtggatcg tctcctcggt gcggatctcg cgcggccgtt cgcactggcc  38580
gcgggcgaga acgtgagggc acggctcgtg cgcttctcgg aggacgagca cctgctctgc  38640
ctctgcctgc accacatcgc gttggatggt tggtcgatca gcgttcttct gcgggagctg  38700
ggttcgctgt accgggggca gccactccaa cccctgccgc tgcggtacgt ggacttcgcc  38760
tgctggcagc gcgacgtcct cgagaagcgc ttcgcggagc agctggacta ctggaaggcc  38820
gagctgcggg agctcccgcg gcagctcgag ctgccatggg atcatccccg tccgcccagg  38880
caggactacc gtggtgcttc cgcgcgtcgc ccactgtccg gggaactacg agccgcgttg  38940
aagcaggtgg ccgagcgcta cgatgtgacc gacttcatgc tctacctgac gtcgttccag  39000
ctctggctcg gacggctcag caacagctgc gatgtggtgg tcggcacacc ggtagccaat  39060
cgccactaca acggcgtcga gtccatcgtc ggcctgttcg tcaacacgct gccgctccgc  39120
cttcggtatg acggctccga gacgttcggc ggcgtcgttc gcaggatgaa gtcgaaggtg  39180
```

-continued

```
ctggaggcgt acagccacca ggatgtgccc ttcgagtacc tcgtggacca tctggaagtg  39240
cccagggagc tgagccacgc ccccatcttc caggcgatgt tcctgctgca ggacgagtcg  39300
gggcgcgaga tcgacctggg tgacgtccag gggcggatcg ctcccgtggc tggcacggtc  39360
gccagattcg atgtgtcgct cctggttgag ttcgatgagg aaggcgcgga gctgaatctc  39420
gagtacgcga gcgctctctt caggcccgag accatcgacg agtggttgga gagcttcgag  39480
ctgttcttgc gcgcgatcgc ggcggacgcg gaggctccgg ttcggcggtt cgagctgttg  39540
ccgccgcgga tgcggtcctt cctgtccgag gtgggcaccg gaccccggcg agagtatggg  39600
agccttcctc tgcccgagct cgtagcggag caggcgaagc atggcggaca gcggatcgcg  39660
gtcgagggtg tccgggaatc gtggacctat ggtgagctcc tcgccgccgc ggagcgtgtc  39720
gcggccggcc tgcagcgccg cggggttcgt cctggcgacg ggtggcgat cgcgctgcct  39780
cgcgaccatc ggttgccctc cgccatgctg ggcgtcctga aggcaggtgc cttctacgtt  39840
cccctggatc tcacgcatcc ggagcgcagg ctccagtaca tcgcggggga tgcgaaggcg  39900
cggttcgtca tcacgggagg cgagacccgg ttcggattcg acatccctcg tgtgaacctg  39960
gacgagctgt tggaggagac ctcggaagcg cggccggtgc ccatcgcacc gtcgagcctg  40020
gcgtacgtca tctacacctc gggctccacc ggtgaaccca agggcgtcat ggtgagccac  40080
gccagcctct cgaacttcct gcacgcgatg gtggaggagc tcggcttcgg gccggatgag  40140
cgtctgctgg ccatcacgac gatcgcgttc gacatctcgg gcctggagct gttcctgccg  40200
ctcatccgcg gggctcgcgt cgtgatcgcg gacgaggact ccacgaggga tccgcggctc  40260
ctgtccaggt ggatcgacga gcgacggatc tccgtcatgc aggccactcc ggcgacctgg  40320
cggatgctca tggatgcctc ctgggtggca cctggatcct tcaaggcgct ggtcggcgga  40380
gaggcgttgc cgcggaacct ggcggacttc atgacgagcc gggtgagcca ggtctggaat  40440
gtgtacggtc ccaccgaggc gacgatctgg agcacgatcg cgcggctgaa gtcgggtgag  40500
cgggtccaca tcgggcggcc cctggcgaac accgaggcct tcgtgctcga tgatgggttg  40560
cgagccgtgc ctcgcggaac cctgggcgag ctccatctcg gtggttccgg tctggccacg  40620
gggtacctgg gtagggagga gctcacccgg cagaagttcg tgcatcaccc ggagctcggc  40680
cggcggctct acaagaccgg agacctcgcc cgggtcttgc cctccggcga catcgagttc  40740
gtcgcccggc gggatgcgca gctgaagatc cgtggcttcc ggatcgagcc gggagaggtc  40800
gaggccgtcc tgagcagggt ccccggggtg gcgcgagtca cagtcctgcc cgtgggggag  40860
ggggagggca cccagctcgc cgcgttccta ttgacggggg atgagcggct ccaggcccag  40920
gcgagagcac tcgcggagca gcaactgccc gaatacatgc ggcctgcccg gtacgtggtc  40980
gtgcccgagt tcccgctgac gcccaacggc aaggtggata cgaaggcgct gcgggcgctg  41040
gtctcggagc aggtggaaga ggcggcgggt tccgcgccga aaaacccgat cgagttcagg  41100
atctcccggt tgtggtcggc gctcctgggc gtccgccatc cgggcacgcg ggacaacttc  41160
ttcgcgctcg gggcacgtc actggccgcg gtccggctcg ctcgcgagct ggagagcgaa  41220
ttcggtatcg aggtgcgggt cggtgacatc ttccggaagc ccacgatcgc ggagctcgcg  41280
ggtctggtgg agacgcaagg ctcggagcgg gtcctcgagc ccctcgtcct cttgagccgg  41340
gagcagcaga agccgcccct cttcgtgatc cacccgcgg gtgggatggc gtactgctac  41400
gccgggctcg cacaggaact ctccggattc acggtccacg gcctgaatca accgcactac  41460
tacgagctgg agcaccgctt cgagacgttg gcggagatgg cggcggatta cgtcgccaga  41520
atcaagcggc tccagccgac cggaccctac cgtctcctgg gctggtcgtt tggtgggacc  41580
```

```
ctggcctatg agatggcgag gcagttggag caggcgggag aggccatctc cggcgtggtg  41640
atgctggacg cgcatcacgt ctcgccgctg ggcgcgaacc tgccaacggt cgatgtctcg  41700
gcgatgctgg ccaacctggg tctgggcggc gagatggccg acccctacct ggagaaggac  41760
atccgcgaga gcgagcggct ctcccgggac tacaaggcct cgcccgtgcg cttccccgtg  41820
ctcctgttca agcccaccga gcggaatggg ttcgaggaga ggctttacgc ggacctctac  41880
aacggttgga gggagtgcgc ggagaactcc gtggtgcgca gtgtcaccgg cgatcatggt  41940
ggagtcctgg accggcgcaa cgtcagcgag ctggccaggg tcgtcgaggc cttcctgtca  42000
ggaggttacg gagtgctcct gcgtgaagcg gttcagcccg ccctcgcgtt cgcgctcgcg  42060
gagcgtgacc gtttcgtcgc caggcggctg gtggagcaac tgccgcggga tctggtggag  42120
cgctggctga agtcggcgat cgactgtctg ccggagtcag tccggccaga ggggtcgttc  42180
gttcaggcgc tgctcgaata ggtgatgtga agacatacat ggatatggag agtgagcgat  42240
gattcccagc agcctcgaaa aggccatcta cggtgtgtat gcaacgcatg ccctgcacct  42300
ggcggacaag cacaacgtct tcgcgtatct ggcggagaag ggcgccgcgg cgcctggaga  42360
gatcgcgaag gcggtggcgg tcgatgggga gaccctcgag aggttgatgc tcgtcctggg  42420
tgccttggag ctcgtccagg ccgggtccga cgggaagtac cggttgcgtg aggggatggg  42480
gccctatctg gacaagaagg atccccgcta cgtgggtggt ttcgtcacgc atctcatcaa  42540
cagcacgtct ggccggatgg gacacctgga tgcatacctg tccaaaggca aggcggtggt  42600
ggacgcggct ctgccttcgc cgttcgacgt catctacaag gacgaggcgt cgacgaagga  42660
gttcatggac gccatgtggc agttgagctt cgacgtctca cgggagctcg tgaagctggc  42720
gggtctggat tcctgccggc agctcgtgga tgtgggcggc gcgagtgggc ctttctcggt  42780
cgccgcgctg cagcactcca gggagttgcg gtccaccctg ttcgatctgc ccaaggtcgg  42840
gcgctacgtc gatgagaccc gccggaccta cgggctcgag gagcggctgc gtttcgtccc  42900
gggcgacttc ttccgggagg agctcccgga gggggactgt ttcgccttcg ggtacatcct  42960
ctcggattgg gacgatgcga catgtctcga gctgcttcga aaagcccatc gagcgtgtag  43020
ggcgggcggg cgcgtgctcg tgatggagcg gctgttcgat gaagacaagc gagggccttt  43080
cgcgaccgtt ttcatgaacc tctcgatgca tgtcgagacc cagggcaggc acaggaccgc  43140
ccgggaatac gtgggcctgt tggaggccgc gggtttccgt gggtgcgagg tgcggcgctc  43200
ctcgcgcgac aagcatctgg tcatcggttt gaaacacgtc accacctgac cacggctggc  43260
aggggaacca gccacgagct ggtcgccagc caagagagag attcgatgat gcgggttcac  43320
ctgccaggcg agtgcgaaga cattgtccgg ctgcaaaaga gagcgggccg tgctgccctg  43380
ctggagtccg agtgcgaggc gctgtcgctg ctgtatgacc gggtctcggt ggagggcccc  43440
tccgaggagg aggagatcct ggccctgctg acgaggccct tcagccggcg tctggccatc  43500
ccggagtact accagtacac cagcctgcac gtgtacggct ggttcctgtc ccactaccgg  43560
agggatccgc tccgcgggtc cctcgtcgca ctgcacacga ccctggtcga tctgctgtcg  43620
gtggaggagc agggagcccg gctcggcgag gccacgccgg cctatattca tgagcggatt  43680
cgcgggttgc gaggtctgct cgggcagctc gatgagatcc ccgtggatcg gaacgggccc  43740
ctgttcgtcg cggacgtgct caagggcagc aagaaggatg ctcaggagca gtggcgcgcc  43800
ttcgtcctgg cgcgttgtac gggattcccg aagtcgcaag tacacgatga gtacatcttc  43860
ctccggtcgg tccacgcctg tgagatcgtc ttcttccagg tgcggtggtt ggccctgcgc  43920
atctcggaga tgatcgccgt ggaccggaag gaagccgtct tcctcctggg gcagttgacg  43980
```

```
agcttcgcag agctcctgaa caagatcttc gacgtgctga agaccatgtc gcccgagcgt  44040
ttcatgagct ttcgagcaca aacgggaaac gccagcgcag ttcagtccct gaatcatcac  44100
gcgatggaga tcgccgtctt tggcttcgac cccgggcggg cgagcgtgtt cgatggcttc  44160
gagcatctga agcggttgaa cgagccgctg tttcgggagc acgcgtcgtt gcggagtgtc  44220
gtcgaagcca cggcggacgg ggcgctggcg gaaggattcg cgaaactcga taggtgtctc  44280
ctccgctggc ggggagggca ctatgggttc gcccggaagt acctgccggt tgacatcaag  44340
ggctctggag gaacggaggg ggctccgtat ctcaagaggt tcatcaagaa ggacgactgt  44400
cagtcaggcg ggcagcggcc gggtaccgac agcgagctgg cgcggttctt cttctgctga  44460
gcgcgggtga tcggattcct ggacgttgac ccgtgaccgt gagccgccct ggcgtcccgg  44520
gtcgacttcc aaggtcccac ccgggccgga gacaggctgc ggctcgaggc tgcgatgacg  44580
acgagcaact ccgggggaaa cgggcgaagc ccgcgatggc gagggtcatg ggtggtaggg  44640
cgctccggac ccggatactc ttcctcgtgg gacaggccgg cggggtgacc ttcgaggtgg  44700
tgcggtcagt cgaggaagcg gcgctgccac tgccgcatgc gcgtcggatt gagtgagcgc  44760
cagcggagtt tctcctcgta caaatatggc tccagtacgc gggccagctc ccggtagggc  44820
cgcagcgctt ccgattgcgc ctcatggccc atggcgggcc attctcccag cgccaccatg  44880
accttgtcct gttccaattc ctggatgtct attcctgggc gatgtagctg ctccaggagc  44940
cccctggctc ccccgagttg tcccagcagg ggttgtccga agaaattcag ccaataggct  45000
cctcttacac cggcaccaat ggcctgggtg gtggcgctca gggcgtgcac atccaatccc  45060
gggtattgga cgcaaagctc tcggatgatt cgatcggccc cgagcacttg catcgagttg  45120
aaggcgaggc tggcatatcc ggaggtgagc ggcagaacgc gcgccagcgc cacggccagt  45180
tctctcaccc gtcctggtcc ccgctcctcc aggtactccg ttggcagcca gcaagaaacc  45240
ccgctcacca tgccagaccg ctgggccgcg gtgggtgtct cgagcttgtt cccattgtac  45300
tcgaagcgat acccggccac ctgatgagcg tgctccagca actcgagaga gcatgcctcg  45360
gcatgagtcg tgtccaggag ccgggagcgg atgtatttcc aacccgtgtc atccaatggc  45420
cggaactccc catctggagc ggcgtaccag ccaagcgtgt cgcgtcccac ggtgtcgaga  45480
tagacatcca gcgcgcgagc cacgaggggg gacacgtccg cgtgcgagcg ttgcatgaag  45540
aagcacagat gaagcccctc acgcagggcc aacaacccat ctttggagta cctcctcact  45600
cgcgggtacc gctcgctcat cgcttgattc cttttcttgg gatgacgagg ctgggtcgca  45660
cgccgaatgc gttccagtag accagttcct gggtgctgcc tgcgtagggt ccccgcaggt  45720
aggtcgtcca tgtcgtggag gagccttgga cgcaggggaa tttgaattcg tagacgaaac  45780
gtgcctgtgt gggttctcca gagtggacga ccacatcggg ctccacggtt cccttgagtt  45840
ctttttcccg gcccgcccgc acgagtcgat cgacttcctc cttgctcagg ggcttgatcc  45900
gccacctttt cttgtcgacg cgatagcgtt gctcgatgag gaggtgcccc gggatgagtc  45960
cccccagtgc ctcctcgatg cacttgaatg cttccttgtg cttctccttg cccagctcca  46020
tggctcgcgt gacgggcttg ccgttcttat ccctgcctac cacctcattg cactctgcgg  46080
aggagaggat tctttccatc aactgccgcc ggttgaccgt ctgctccgcg cgctcggcgc  46140
actcctgcat gaactcgtcc agttcgtcct ggaggtcatc gaggtcatca tcatcgccat  46200
ggagcagcac tccaatggcc cagcctgctg caaatccggc tgttgccgcc acggccgttt  46260
gactgacgga tgcgccctgg ctcgtgggag aggtgagtcg gaaggttgcg acttctgctc  46320
cttcgagccc attacagaca tgggtctcat aaggatgcct ttccaaacag caggtgtagg  46380
```

```
tggtggtgca tgctttcggt gtatcgagta gacaaccacc ggtgccgacg ctggcgagta  46440
gcaggacgag cataggagat agcgcccaca gcctgggcct ttcggtggtg cgggcgtgcc  46500
gagtcacagg gcggccccgg cctgtgtctc ggcgtctttg atacgaattt cgccggagag  46560
gagcttgggg aggagagtgt cacggagttg cgcaagtgca tggttttgct gctcgttccg  46620
taccttgtcg aggtcaggcc gtgcgtggtc cttgggcagc acgcccttga ggctcgggta  46680
gtctcgctcg atggcgacca tcgcgtcatc cacgagcttg ccgatgacgg gctgcttggt  46740
gttggccttc agcttcgccc agcgcgcctc cttcggcacc cagaacacgt tgtgagcccg  46800
gtactcgtct ggatcctccg gatcggcgcc cttggccacc tctgcgacca gttgggtgtg  46860
ccgctcctcg aaggcgtcgc tgacgtactt gaggaagatg agtccgagga ccacgtgctt  46920
gtactcggcc gcgtccatgt tgccgcgcag gggctcggga tggccgagga tgcgctggac  46980
gagcacttcc ttctcgcgtc caccccggtc caggcccagg gcgtcgcaga tggcctggag  47040
ctcctcgcgc ttgagctggc ccaggagccc ggcgaagtcc accgagcggg agcggacgag  47100
ggcgttgatg tggttctcgg tgacacggcg gtcctcgacc tcgaggccga gctgctccgt  47160
gagctgcgag agccggttcc ggtctagtac caggagcgcg gcccggtgct gctggggcga  47220
gagacgaatc tcctgtgatg gcatgggcgc aggttaccgc atggcccccc ccggcgttgg  47280
cgggtgaaat cgtgcttacg gagttcacag cgcgggtagc atggctcgca tgctgcgttg  47340
ggctgggcga gagaaggggc gggccgtgct ggtgttcgcc gccgtgtcgc tgctggtcct  47400
cccgctggtg ggactcgtca tcctgtggag ccgggcgccc gaggagcggg tggtcgatgg  47460
gtggcgcttc gtcccctgct tgacggccgc ggaactccgc gcgaggccca ccctccgtca  47520
gccgtgccag ggagacgcgc agtgtgatgc tccgctggtc tgtgcctacg acccatacga  47580
gcagcaacgg ctgtgcacgg ccagtagctg tgactcggat tcgtggtgcg cgccgtatgg  47640
ggtctgtcgc tccctcccca ttcgaagtgg gcaacgggtg gccagtcgcg tctgtgttct  47700
cgaggggacc cgtgaggagg gagagccgtg tctccgttcc ccgaggccga accagaggga  47760
atggggctgt ggtcaggggc tcgtctgcgc gggtgctggc tggtgcggcc ggcggtgtgt  47820
gcccggacag gaggggtcgt gtccggaggg cttcttctgt gctcgcggtg accccgatgg  47880
acccgtatgc cagcccacgt gcgagggccg cgcgtgtccc gagggccagc agtgcatcca  47940
gtgcgagggg ggtgtgtcgg tatgtgcgag ggtgaaagga cgcgcatgcc ctggcgagcc  48000
ctgtaccggg aaccgggtgt gtgtgacgga gatgtccgtc cacgccgtgg gggaggcgcg  48060
gaggcggtgc gtgcagccct gtggtcaggg cgggcccggc gaatgtgagg agaggtttcg  48120
ctgccaccag gggcaatgcc gccggcattg tctcgtgggg cagcccgaag tgtgcggccc  48180
gttccggttc tgcgtacgca ccgatgaggc gggtaacggc gtgtgcctgt catcgctgga  48240
gcaatgggac atgaacgccg agccggcccg ggagggcgag tggaatcgtg cgccgggccc  48300
actgcgcagg tagcatggcg cgcatgatgc gaagggttgg gcgggagaag gggcgggccg  48360
tgctggtgtt cgccgccgtg gtgctgctgg tcctcccact ggtgggactc gtcatcctgt  48420
ggagccgggc gcccccggag cgggtggtcg atgggtggcg cttcgttcca tgggtgtctc  48480
ccggggaggc ccgcgaacgg cccaccctcc ttcaaccctg cctgggtgac gagcagtgtg  48540
acgccccgtt cgtgtgtttc catgacccgc gctatcagca acggtggtgt acggccagtg  48600
attgcgagtc ggactcctgg tgccccaccc agacggcctg ccggtccatt cccatgcggg  48660
gacggcagaa gatggctctc cgcgcatgtg ccctcgaggg cacgcgaaag gagggggagc  48720
ggtgcctccg gtttcctcag gcggtcctgc gggagtgggc ctgcggggag ggactcgttt  48780
```

```
gcgccggttc cggctggtgc ggccgacgat gtgttcccgg gcaggagggg acatgcccgg  48840
agggcttctt ctgtgccccc ggcgaccccg atgggcccgt gtgccagccc acgtgcgagg  48900
gccgcgcgtg ccccgagggc caggagtgcc tccaactgga gggcggcgcg tcggtgtgcc  48960
tgaaggtgca gggacgctca tgtcaggacg atgaaccctg ctccgatgga gaggtgtgtg  49020
tgacggagcc gttcctttcc ttgaaggggc aggcctggag gtcgtgcgtc cagacctgtg  49080
gacacgaagg tgccgcgagc tgtccagagg actccgtctg cttccacggc cgctgccgcc  49140
tgcgctgctc gttgctgcgt ccctacccgt gttggacccg gttctgcgtg agcaccgacg  49200
acgcgggcaa cggcgtgtgc ctgtcctcgc cggagcaatg ggacatggtg gacgccgagc  49260
atcgttgacc cgcgaccacg agccgcccta gcgttcgagg ccgattccaa ggtcccaccc  49320
gggccggaga cgggctgcgg ctcgctggcc accgtgtggg cgcccgaccg cgtgggggga  49380
cgcgagcggg ccgtgtgctt ccaaccacac ctcccctcca gaacggcgtc cggcaccccg  49440
gcacgccgcg tgaacaaccc gagccatttc ctcggaggaa ccatgggtcc gcagtccgtt  49500
tcaatgccga agccgttccg cacggccagg gcgcgctggt tgctggcggc gctgctggtg  49560
ggcgcgatcg ccggctgcaa caaggacgaa tccacgagca ccccggcacc gtccggtccg  49620
gcccccacct cgggggcccc ggccagcggc agcggtccat ccggaacgag cactccgagt  49680
gccccgccct cggcggactc cctcgccccc gtcatccacg agatcggccc cgagggcatg  49740
gtgccgcgcg aggtggtgct ggagttcccc cgctcggtgg cgcccgagaa ccaggaggtg  49800
aagaagggca ccgtcttcac ggtgtctccg aacgtgccgg gctcgctgag cttccgcggc  49860
ggctccacgc tcgtcttcac cccgcgcgag agcttcgcct tcaagaccga gtacactgtc  49920
tcgctcgatg cgctcgagct ggccgacggc accgtggtga agccccaggt cgcggggggg  49980
tggagccgca ccttcaccac gcctgccttc gccttcctgc gcctgtcgcc ccggcagatg  50040
gacgtacgca agggcaaggt ggaagcggac ctggtcttct ccggcccggt ggacgtggcc  50100
aacgtgcgcc gcttcgcttc cttctccgtg gacggcaagg cgctgtccga cgtgaagctg  50160
cgctcccacc cctcggaccg tcacatcgtc accgcggccc tgggggcgc gagccttcgt  50220
cccggcgcgg aggtgaagtt caccctcaag cagggcctgg cctcggctgg ccgcaatggg  50280
ggcaccgcgg cggcggggga gggctccttc gcgctgcacg tgggcaagcg cctcgacatc  50340
accaacgcct acgcgcagga gggcgcctcc ggtcattaca tcgaggtccg ctgccgcgag  50400
gtggagggtg acgcggcgcc cagccacccg gagggtgagg aggattacga ctattactat  50460
ggagaaggtg gcgagcgctg cagcctcgac gaggactccg ccgcggacac catccacttc  50520
aacccgccgg tgaagctctc cgtgtcgccc tcgcgctggg gcttccgcgt cttcggtgac  50580
ttcaagcgtg gctcctattc catgcgcatc gacgcgggcg ccacctcgtc caagggcggc  50640
acgctgctgt ccacctacga gaagtccttc tccatctccg cgcgcagccc gcagatcagc  50700
ttcggctcca ccggccgcta cctgccgcgc agcgcctggc gcaacctgcc cctcaaccac  50760
ctcaacctgg actcggtgga gctcgtggtg cggcacgtgc cccaggagaa cctcctcttc  50820
tggatgagca atgacggtca ggaggccgcc gacgagcgca cctccaacgt gctgctgcgc  50880
aagacgctgg ccctgaaggg cgcgcaggac acgctggcca ccacctggct ggacgtgggc  50940
agcctcgtgc ccgcgagcac ccggggcctc gtggagatca ccgcctcggg cagctacaag  51000
tcgtccgcct cgcgcatcct cctcacggac ctgagcctgg tggccaagcg cggcctggcg  51060
ccccggggct cggaggcgaa ggaggaggtg ttcgtgtggg cgctcggcat ggagagcacc  51120
gagccgctgt ccggcgtcga ggtctccctg gtgaagaaga gcggccaggt ggtggcccgc  51180
```

```
tgcaccaccg gggcgccga cgggtgcaag ctgacggtcc ccgcgccggg ggtggatacg  51240
gccgagccct tcgccctgct cgcgcgcaag ggagatgagt tcacctacct caagtacaac  51300
gagctgaaga cggagatcgc caactcggac gtgcagggcg agccgtaccg ctcggacaag  51360
ccctaccgtg cctccgtcta ctcggaccgg ggcgtgtacc gcccgggtga caccgcgcac  51420
gtggtggcgg tgttgcgcgg ccaggacgac gtggcgccgc cggtgggcat gccagtggag  51480
ctgaaggtgg tggacccgcg cgagcgcgac ctgaagaagg tgacgctgaa gacgaacgag  51540
gcgggcctgg tgtcgctgga cgtgcccttc gaggcctacc aggacacggg cgcctaccac  51600
gtggtgctga gcgtggccgg caagcaggtg acctcgtacg gcctcaacgt ggaggagttc  51660
gtccccgagc gcatgaaggt gacggcccag gcggagaagt ccggctacgt gcagggcgag  51720
gaggtgccgc tgacggtgga ggccgcgtac ctcttcggtg gctcggcgga gaacagcccg  51780
gtggaggtga cgtgccggct ggagccgtcc gtcttccgcc cgaaggacaa cgcgcagtac  51840
gcctacgggg tatggcgtcc ggagggctcg gacgcgaagg ccaccgtgtt ggggcaggtg  51900
aaggccgagc tggacgcgaa gggccgcacg ttggtgcgct gcccggcgca gcaggacgcg  51960
ggcggcttca agggcccggc gaagctggtg gcgcaggcca gcgtcttcga ggccggcagt  52020
ggccgctcca cgctgggcga ggccaccgtg ccggtacacc cggaggcgta ctacgtgggc  52080
ctccaggcca acgtggacaa ggtgaaggcg aaccagccct tcaccgtctc cggcgtggtg  52140
gtggactggc agggcgctcc ctacggcaag gccgtcaaac cgctcgacgt ggagtacctg  52200
cgcctggatg aggagtacgg ctacttctat gacgagggct cgggcgagga gcgctaccag  52260
cgccacctgc gtcccgtgcg cgagggccgc accaccgtca agcccgaggg cgggaagttc  52320
tccttccagg tgacgccgtc cacggatgcc gcgggctacg tggtgcgggt gaagtccggc  52380
gcggcgcaga cggatctgca gctcgagggc cacggccgtt attactggtg ggacgagtcc  52440
tcctcgcggg tggaccagac gccccggccg gcgcggccca cctcgctctc ggtggagctg  52500
ccacgctcgg cgaaggtggg ggactccatc acggtgaagg tgaaggctcc ctaccgtggc  52560
cgcatgctct tcaccgccga gacggatggg gtgcaggccg ccgagtggaa ggcggtggag  52620
ccgggcgagg tgacgtggac cttcaagccc tcggccttcg cgcccaacgt ctacgtcagc  52680
accttcctgg tgaaggaccc gcacctcgag tccgcccagg ccttcatgcc ggaccgggcc  52740
ttcggcgtgg ccagcatgac tctggagccg gtggacttca cgcaggccgt cacgctgaac  52800
gtgcccaagg aggttcgctc caatgacacc ctctcggtgg acctggagct gggctcggtg  52860
gaggcgggta ccttcgccac ggtggcggtg gtggacgagg gcatcctctc gctcacgcgc  52920
ttcaagagcc cggatccgct cgcggagctc ttcacccggc gggccctggg cgtgcagacg  52980
tacgagacgc tcgggtggac gttgctgatt cctcccgccg gcgccagccg ctccacgggt  53040
ggtgacggcg agggcgatgc ttcaggccgc gtgcagccgg tgaagccggt ggccctctgg  53100
agtggcgtgc tgccggtgcc cgccaacggc aagctgcgcg tcccccttcaa gctgccgcag  53160
tatcgcggcg cggtgcgggt gatggcggtg acgagtggcc ccaagcgcat cggccacgcc  53220
agcgcgcagg tgctggtgcg ggatccgctg gtgttgcaga ccacgctgcc ccgcttcctc  53280
agccaggggg atgagattca aatccccgtc ttcgtgacca acctctccgg caaggcgcag  53340
gacgtgaagg tgtccctcac cgcggagaac ctcccggtgc cgggcatggc gatgcccgcg  53400
tccatggcct cgccgctgca actgctcggc aagagcgagg gcaaggtgcg gctggaggag  53460
ggcaaggcgg ccacgctcgt cttccaggcg aaggcggtgc aggccgtggg cgcggctcgc  53520
ctcaaggtga cggcggaggg cggtggacac acctccttcg agcagctcga cgtgcccttc  53580
```

```
cttccctcgg gcccgcgcga gcgcaaggtg cagcggctcg aactggccgc cggcacgttg  53640
gatctgtcgc agtacctgca gggctggctg cccaccagcg agcgctcgac gttctgggtg  53700
accacgaatc cctacgccga gtccttccag cacctctcgt acctggtgca gtacccgcac  53760
ggctgcatcg agcagacgac gtcctccacc cgcccgctgc tctacgtctc cgagctcgtg  53820
gacagcgtgg acccgacgct cacggccaac gcgaaggtgg aggacatggt gatgtcgggc  53880
gtgaaccggg tgctctccat gcagacgccc tcgggcggct tcggctactg gccgggcgcc  53940
accgagccgg tggagtgggg cacggcctac gccacgcaca tgctgttgga tgcgcagaag  54000
cgcaagtacg cggtgccgca ggaccgcatc gacaccgcga tcgattggat gaaccagcag  54060
gtgacgcgcc gcgagggccg ctcgggctcg ggtgactaca acgatggctc cgaggcctac  54120
atgcactacg tgctggccat gtccggcaag ggtcacaagg cgcgggtgca gaagctcatc  54180
gaccagctcg ggagccagaa gttctggagc aacggccagc gggcggagca ggaattcatg  54240
ctcaaggccg cgctgtacca ggccggcgac cgccgctacg agaaggacct gcgcaacccg  54300
gacgcctcgg cggtggtgga ggagcggtgg aacggttggt ccttctactc ggaccggcgc  54360
cggcgcggct tcatgctgag cacgttccag gacctgttcg gggatgacgc ggcgggcgag  54420
ccgctcgcgc agcaggtggc cgaggccctc aagcaggagc gcagcagcta ctacaccacg  54480
caggagctgg tctggggcat caccggcctg ggcaagcgcg tggcgggagc ggcctcgaag  54540
ttcgctccgg cggtgctgac ggcggatggc aaggaggtgg cgacgcggga gggcgtcaag  54600
caacgcgcct ccgatcggac gtgggcgctg gtgcgcgcga gcgagcgcaa gggcctgacc  54660
ttgaaggtcc cggagaaggg tgagggcaag ctctacctgg tgctcgcgag cgagggcgtg  54720
cgctcggacg gccagtaccg cacgggcggc gaggggcttt ccctggagcg tcactaccgc  54780
aacctcgcgg gcgacgtgct cgatgtgcag ggcggctcgg tggccctggc ggacctcgtc  54840
tacgtggagg tgaagatcaa gaacacctcg cgtgagcgca tccagaacat cgcgctggtg  54900
gaccggctgc cggcgggctg ggagatcgag aacgcacggc tcgggcgcgg gggcgcggtg  54960
gagtgggcct ccagcgagga gcagtggagc gcggactacg tgaacatccg ggacgaccgg  55020
atggaggtct tcggaagtct ggaggcgggc gagacgaaga cggtggtcta cgcggtgcgc  55080
gcggtgacgt cgggcaagtt cacgctgccg ccggtcgagg cggaggcgat gtacgacccc  55140
cgcatctggg cgcgcgaggt gggaggctcg gtcgaggtct ccggcccctg gaaggacttc  55200
ctgctgtagt catggcggag gcggtcgctc tggcggggac cctggaaaca gggtcctcgt  55260
caaagaacac gctggagcac tcgaggatcc acgacacggg caattaccag ccgggatatg  55320
gcgaaggcgc ttatgtcggt tccgatgcca gctcggccaa tgacaacacc ctcatccggt  55380
acaacgaagg ctaccggaac gggaacgcct ccgtggtgga cgccttccag gtccgcacgc  55440
acggcagcgg tgatgatgct ccgggatacg tggtgtatgc gacgagcgcg accacgggca  55500
cgacagcctc cggtgatgtc aggattggcg gcgggaatct gtataacggc aacgtgaaca  55560
gatgagacgg cgctccgggc cttcgaggtg cgccctcagc gctggggcca ggacaggatg  55620
atgcgcgctc cgcccagggg cgcgtccgct acacgggcgc ttccctggtg cgcctgcatg  55680
atgcggtgga cgatggccag gcccagtccg tggccacccg tcttgcggtt gcggctgtcg  55740
tccaggcggg tgaagggcag gaagatgcgc tccctgtccc gaggcgggat gccggggccg  55800
tcgtcgtcga cgagcacgga gtagcccgag tcgttcctct ccaactgg              55848
```

<210> SEQ ID NO 2
<211> LENGTH: 2049

<212> TYPE: DNA
<213> ORGANISM: Artificial
<220> FEATURE:
<223> OTHER INFORMATION: Seq.-ID No. 2: arg1

<400> SEQUENCE: 2

```
atttgttgct cacgatacgc gtcccgggct tttctgatgg gccagaccga cctactcctg      60

ctgaacgcat ccaatcttcc gcagctcccg atctatccgt atgccttcgt gcaggttagc     120

gcgatcgctc gtcggtttgg cctttctgtg cggaggctcg atctattgca ggtgcgccgc     180

gagttctgga ggcccatgct gcgggagctc atccaacggc atcggccccg gatggtgggt     240

atccatctgc gccagcagga tacggtgctt catttcgact atcacaaccc acagatgggg     300

gtgatggcgg ggcgctattt cccggtgcag gacacgcggg cactgattga ggtgcttcgt     360

gaggtgggcg acatgcccat caccatggga ggattcgggt tcacgtccca tgcccatctc     420

ctgctcgatt atctcggggc tgacttcggg gtgcagggag atccggatgg attcttcgcc     480

cgcttcgagg acgtcgtcgc gagacgcgat ctggaatcgg ttccagggct ggcctatcgc     540

cgcgatggca cctatcagtt caatccgcga gggttctatc ctccggcggc ggagcgcgag     600

tatacggacg agatcgtcga tgagctgatc tccttctatg gacatgctca gctctacggt     660

tccaacccgc caacggtggc cgtggaggcc atgcgcggct gcccgttcag ttgcggtttc     720

tgtctggagc cccacgtcaa gggacgccgc atcgcgtacc gcgacatcga aaccatcgtg     780

agcgagctgg agttccttct cagccgcaac ctgcgccggt tctggttcgt tgcctccgag     840

ctcaacatcc aggggtcgga attcatcttg aagctcgccg agcgcgtcat ccggctcaac     900

gagacccatc ccggcagccc gatcgaatgg tccggtttca ccctgccacg attcaacgag     960

tcggatctcc ggctcctgca gcgcgcgggc tacgcgggtg ctctcaatga catcctctcg    1020

ctcgatgacg aaaacctgca ccggatgcgg gttccctacc gctcgggtca ggccatcacc    1080

tatctgaagg ccatggccaa gatggccgag gaggagagcc aggcacaggc cacgagtccc    1140

cacggggtgg aggggctgcg ccagcggctg gcgggctatt tcaccctgtt cctgggcaac    1200

tcccacgccg acgagcggac catccgccgc tcgctccagc aggtcgacga gcacggccta    1260

cgcgagaagt accgcggggc gttcgtgatg gccgcgactc gggtctacga catcgagggc    1320

aagtacatct gcgccacgag cgaggaagag gcgaagagca tcatctcgta cgacgagcgt    1380

ggtgagcgcc cgttcaacct gctgtggccg tccttctact accctcggtt cctgatgcag    1440

cggctcggct ccacggcgga gatcctcaag ttcttctcgt tcgttggaga caccttcctg    1500

tcgctcgctc atcgcatgcg caaggattgg aactggttct tgtcgcggaa cacgagcgtg    1560

gaacaacttc gcgagtggct cgccggagcc tcctcggtgc cctcggagc ccacgaggcg    1620

ccgccgcatg tcctcgagaa ggcggcgcac gtcctcggag agccccggac gcccgcgctc    1680

gtgtcgatga tggccccgga acccgagcag aagcccctct ggaacgaggt cgccagggtt    1740

ctgctcgagc acctcttccg ggtgcacggc aagtcagtgg cggcggtgac cacgcatctg    1800

gggattcagg cggatgagcg tggaattccg cgattgtcgg aataccggct catggagcgg    1860

ctgtaccaac gctacgattc agtggagcaa ctcatcgagg aggcaggatc ttgcctcgat    1920

gtgacaggcg attcgctggc gatgctctat ctgcaatggc tgctctatgc caacaacgtc    1980

acgattcgtc ccgaataccg cgaattgctc ttcgagccgc cggtcgagcc tgcttcagcg    2040

gttggctag                                                             2049
```

<210> SEQ ID NO 3
<211> LENGTH: 10617

<212> TYPE: DNA
<213> ORGANISM: Artificial
<220> FEATURE:
<223> OTHER INFORMATION: Seq.-ID No. 3: arg2

<400> SEQUENCE: 3

```
atgagccgtt gcgaacagcg gcttcgagat agaacgaaaa tggatacgcg caagcaggcc     60
tctggcgagg tgtgtttcct cgacctcttt ctgcgtcaag cggagcttca tccgtcgaag    120
tccgcggtcg aatgcggctc ggcccggctc acctatcagg cgcttgtcgc caggagtgaa    180
cggctcgcat ccgcgctggg ggcgagcggc gttcatccag gggatcgcgt tgccgtcgtc    240
ctgcatcggg gactcgacac cgtggtcgcg atggtcgccg tgcttcggac cggtgccgtc    300
tatgtgccga ttgacgtcac ctggcccgac aaccgtatcc gttacatcct cgatgacctg    360
cagccgggcg cgatcctgtg tgacgaggag aactcgcggc gcgcttgctt cacgagtgat    420
gaccggctcc ttctggcctc ctccgagggg acagggggct cggatttcag gcctggcccg    480
atggcgcccg cctacttcat gtacacctcg ggctcaacgg ggcgacccaa gggcgtggtg    540
ctcgctcatg gcggtctggc gagccggctg catgcgttct ctcgcgcata tgagatccaa    600
cccgaggacc gctttctcgc cctgagctcg gtctccttcg acgtgtcggt cctcgacctg    660
atgcttcccc tcgtcaatgg atgctgcacc ttcattgcgt cggatgagca gcggcgcgat    720
ccggatgcgc tgcggaacct gttcgaggag cgggcgctga atgtcgcttt cgccacgccc    780
accacgatgc gcgccctcgt ctccgtggga tggaagggga gtccccgcac caagatcctc    840
tgcggtggtg aggcgatacc ccagtcgctg atgaacgaac tcgtcgcccg gggggcggttg   900
ttcaacgtct atggaccgac ggaagccacc gtcgcggtca cttcgccaga gctcttcgcg    960
ggtgacagtg tgcacctggg ccgcgcgctt ccgggggtgg agttgctcgt cctggacgag   1020
gccggagcga tctgtggacc ccggcagcca ggagagctcg tcatcggcgg gatcggtgtg   1080
gcgctggggt attggaagaa tgacgagctc acccggaaga agttcgtcga cgggaagtac   1140
cggacgggcg atctcgtgag ctggggagag gacggcaatc tctactacca cggtcgcatg   1200
gatgagcagg tcaagctcca cggtcaccgc atcgagttgc tggagatcga ggagatggcc   1260
cgctcgttgg ggctcgtccg tgacatcaag gtcctgattc aggagaacgc ggcatcccct   1320
cggctcgtgg ccttcttcat cggtgacgag gcagccgcac aatcgctgcg gaggaggctg   1380
gccagcgagc ttcctgccta catggtgccg tcggtgtggg tcggggtcga gggctttccc   1440
cagacgtcga ccggcaagct cgaccggaag gcgctcctgg cgaaggtcga cgagcgcgcc   1500
gaggggctcg acagtcctcc ggaagcggct ccgtccggcg gtcgcgaggc gactctgctt   1560
ggtatctggc gggaggtatt gcagcggccg gatctgtccc cggacgatga tttcttcgcg   1620
agtggtgggg attcgattct ggcgatgcgc accctgagcc gggcacgcga agcgggaatc   1680
aactaccggg cggttcatat cttccagcac ccgacggtgc ggagtctgct ggagaccgtc   1740
gttcaggcgc acgaagggcc caggcccgaa ctgcccgagt tgaccacctc gggtctgacg   1800
cccgtccaga gatggttctt cgagcagccg ctggtcaacc gggggttctg gaatcagagc   1860
attctgctcc ggctgacgcg cccgatggag ctgcgagagc tccgggagat cgcggactgc   1920
ttgacccgga cgcatcagat cctggcttgc gagatcgatg aaaagggaat gcgactgggc   1980
tccagggacg ccgacgcatg ctgcgcccag gtgtccctga ccacgggaag cgggacgtca   2040
tccccagaat ttgcccggat catcgacgat gcgcaccgga gcctgcgccc tgaggaggga   2100
aggctgcatc gcctggtcct gatcgaatcc aggggttctg gcgagtggta cctgttctgg   2160
acgattcacc acctggtcat cgacggtgtg tcgtggcgga tcctcttgag tgacctgggg   2220
```

```
accccttctcc agcagaaggc cagcggagac gcgctccatc tggagaaggc ccccgtgagc   2280
ttcctgcatt gcagtgagcg tatgcgggcg ctccacggga aggtgcggga ggcagagctt   2340
tcgtactgga ggaagctccc cgaggcgccg ttgccctgga gctccgaagt gcggcaggag   2400
gtgcccgaag cggcgcggac cgagctcgtg ctctcgctct cacaggaggc gacacgcggc   2460
ctgctccagg atgtgctggc cggtacgggg aagggcatca acgatgtcct gctctccgcg   2520
ctgctccagg ccgtgtatga cgtgtctgga gagagacgcc tgtcactgtg gctcgagggg   2580
cacgggcgcg aagaaggtct gctcgaattg gatacgtcca ggacggtggg ctggttcacg   2640
tccatgttcc ctgtctacct ggagagcccc tcgccggagg acttccagtc cacgctcgag   2700
gcgacacgcg cgtccctcgg cgcgatgccg aaccgtggcg ttggctacgg catcgtgcgc   2760
tacctgggag aggatgcgcg cggagaaggc cttcgtaccg gcaatgagcc gcgcatcagc   2820
ttcaactatc tgggccaatg ggacgacgtc gccagcgacc atttctcggt cgtgagcgaa   2880
cccggcctcg atgacatcgc gcccgagaac aagtggcatc gagaggtgga catcaactgc   2940
ctcgtcgccc aggggatatt taaggtccac ctgacattcg tgcggcggct ccaggacaag   3000
gagaagctcg agagtctgct gcgtcgcttc atcgcgcgcc tggaaagcgc catcgacgcc   3060
tacaagggcg ccggcgagtt ccggcggaag ttccccctcc tgtcgattcc tcccgaggcc   3120
ttcgcccgca acggcatcga tctccaatcc gtgcaagatg cctacccgct gacgcccatg   3180
caggaaggca tgctgctgcg tgccctgacg gtgccggaga gcggcaacta tatcgttcgt   3240
accttcttcg acctcacggg agagctccat cccgacgcct ggcgggaggc gtggcgacgg   3300
gagttggccg agcaggaact gctgcgctcc gcgttcttct gggagcattc accgaccccc   3360
ttccaggtcg tcttctctca cgtcgacctc gattggcgga cgcacgactg gggccacctc   3420
ggcccggagg agcagcagca ggcgttctcg aagctggaga aggctcgtca tgccgaggga   3480
ttctccctga gcaaggcgcc tctgcttcgg atcgatttca tcgccagggg cggcagtgat   3540
tacaggctcc tcctgagctt ccaccatttg attctcgatg gctggagtct ccaggtcctc   3600
ctggagcggg tgctgaagcg gtatgggcag gcgcgaggtg gcggggaaga acggctgact   3660
ccagcatttc gtttccgcga ttacgtcgcc tggaaccgca accacgagtc ttctgatgcc   3720
ctgcggttct ggcgcgagca tctcgagggg gtcgaggagc cgaccctgct gggtgacgag   3780
cagggcaccc ggcacgagta cgcggaaacg gtactacgtc tggaagaggc ccggtggtct   3840
gggctcggtg cccggtgccg gcggcagggg atgaccaaga gcagcctgat tcaggctgtg   3900
tggtgctggg tggcgaagtc ctacgggcgg aagagccatg tggtctatgg cttgactcaa   3960
gcaggccggg ccgcggccat cggcgatatc gaaaacggcg tgggcctgtt catcaccacg   4020
agcccggtcg cggtggacct ggacaagcat tccaagctgt ccacggtggg aagattcatc   4080
cagcaggtca acgcccaggc cctacaccat gaccggctcc ccctgagtga gatccagcgc   4140
atctcggggc gcgagatcgg acaaccgcta ttcgattgcc tgttggtatt cgagcaggag   4200
ccgatccccg aactcgcggg aggcgtgagc ggcggcctgt cggtggccgg tactcggacg   4260
tatgagtcaa cggagtaccc tctgaccctg agcatcctgg agaagaggga tgggagctgc   4320
gatctccgct tctatttcaa caagaagaac ttcagtgagt tcagggtaga aggactccgg   4380
cttctgttcg aggaaatcct tgccgcgtgg gaaagagagc aggaactcga gctctcttcc   4440
ctgcctgcct tcccgagccg ggatggcgcg cttctctcgc ggtggaacgc gaccgggtcg   4500
gactacccgg cccaatccct gacggagctc ttcctgcagc aggcccggcg tacccccaac   4560
caccgtgccg tgcgatacgg cgagcgcgag ctatcgtacg cggaattggc cgagcggacg   4620
```

```
gggaccctgg cccggcgcct ggaggcgctc ggagtccgcc ccggaacccc cgtggcggtg   4680
cacatgcatc gcagcctcga gatggtcatc gcgctacacg cgattgttcg agcgggtggc   4740
gcctatgtgc cgatcgatcc ggagtatccg gcggcgcggg tgcggacgat cctggaggat   4800
gtggcggcac ccgtcgtcat cttccacgac gcggctccct tgaagtgcca ggtgggtggc   4860
accgttttgg atgtcacccg gattgtcgag gagggtcatg gcggggcgga ccaccgcgcc   4920
gcggagtatg accccgagcg gttgatgtac atcatctaca cctcgggctc cacgggacgg   4980
cccaagggcg tcaagtgtag acacgagggg gccgtcaacc ggatctgctg gatgcagcga   5040
agctacccgt tgtcatccga cgacgtggtc ctgcagaaga ccccgtacac gttcgacgtt   5100
tctgtctggg aattcttctg gcctctggcg gtgggcgcca gcctcgtggt cgcggcaccg   5160
ggcgtgcacc aggacgcgag cgccctggct gctctgatcg agcgcgaagg tgtcacacac   5220
ctgcacttcg tgccctccat gctggatgtg ttcctcgcga gcaagggggg cgctcgctgt   5280
gcctccttgc gccgtgtctt ctgcagcgga gaggcattgc cctcgccggt ggtcaaggag   5340
ttcttccgct ccgtgccaca tgcggagctg cacaatctct atgggccgac cgaggcctcc   5400
atcgacgtga cggcgtggga ctgtcggtcc gacagtccgg tggcctcgat tcccatcggc   5460
tacgcgatcc agaacgtgcg gctccatgtg ttggatgaga agcaggctcc cgtgccccac   5520
ggtgttccgg gcgagctctg catcgcggga atcgccctgg ccgaaggcta tgtgaaccgg   5580
ccggaggaga cggcgaagcg cttcgtccag tcctcgtggg atgcgcggga gcgcctctat   5640
cgcacgggcg atctggcccg ttacctcccc aatggagcca tcgaatacct ggggcgactg   5700
gatcagcagg tcaagctgcg agggttgcgg atcgagctcg atgaggtctc gagcgtgctc   5760
ttgcgcgatg cccgggtgcg gcaggccgtg gtccgcgtcg tcgcgggtcc cgcggggcaa   5820
cccgtgctgg ccgcctacgt cgttgctcac gaaggctcgg ccggaacgtt ggaggaggca   5880
ctgaaggcgg agctcgagcg ctccctgccg aggtacatgg tgccggagtt cttcttcttc   5940
ctggaggcgc tcccggtcaa tcgcaatggc aagctggatg ccgatgctct gcccaggccc   6000
ggggcctctt cctctcggga gtgggagccg ccccagaccg aggtcgagaa ggatctcgcc   6060
gcgatctggc agcgggtgct gggtgtcgag agggtaggga ggaacgacag cttcttcgcc   6120
ctggggggcg attcgatcct gagcatccgg atcctggcgc tcgcgaagga gcgcggatgg   6180
gacgtgagcc tcggggagtt gttccggtct ccgcggttga gcgacttcgc caggaccgcg   6240
aaggcggcgg cgcacacgcc cgtgctcgcg cgctccgcct tcagtctgat cagcgctcgt   6300
gaccgggccg cgatgccggc aagcgtggtg gatgccctcc ccatcgcggc cctgcaagcg   6360
ggaatgctct tccacacgaa gctcgcggag gaaggtgtca tgtaccgcga cagcttcctc   6420
tacgtcattg gtggggagtt caacgagcag gcgttccggc aggcgttgaa ggagttggtg   6480
catcgccacc cgatgctccg caccagtttc gagctcggtg catactccga gcccctgcaa   6540
cgggtggagc gggaagtgga gttgccgctg cggctcgagg actggcgtga cagccaggat   6600
caggagcagc gtctgtcggc gtggcatgag agctaccgcc cgacgttcga catcactcga   6660
gcgccgctgt tcaagatgga ggtcaagctc ctgagcggtg ccaggttcgc cctgggtctc   6720
tgcttccacc atgcaatcct ggatgggtgg agcatcgcgt cgatgatgac ggagctgctc   6780
ctggactacc agcgcctgct gacgggtcgt gggcgggcga tcgagccgct ggggtctgga   6840
tacgctgact atctggagct ggagaagcgt gtcgtcgagg atccccagca gaaggccttc   6900
tggtccacgt acctgaatga cgcccagtcg ttgaggttgc ccgtcaagca ggaggtggag   6960
catcggaatc ggcgtggaac gagtgtccac ggccggttcg acattcccga ggagctcgtc   7020
```

```
gggcagctgg agcggatcgc caggtccctg gagatcacca agaggcatct gttcctcgcg   7080
gcccatttcc gcgtcctcgc gatgatctgc gggcataagg acatcgtctc cggggtcgtt   7140
acgaacggaa gaccagagac ggtggacgct gaacggatcg tcgggttgtt cctcaatgcg   7200
cccccgatgc gcttgacgct cgggggtgga agctggcgcc agctgatcca ggccatcgtc   7260
gaggaggagc ggaacatcct tccccacaga aggtatccgg tctccgagat gaaacggcat   7320
tgtgtccagg ccgacctctt cgacgtggcg ttcaactatg tggacttcca cgtctattcg   7380
cgggcgggcg agctggcgtc ggtgggcatc cagacgctca aggcgaagga ggtgacgaac   7440
ttcgggctgt acgtcacctt ctaccagggc tggccgtaca gcaatcagtt cacgctggcg   7500
tatgatccgg atctcttcga ccgggagcag gtcgatcaat tcgcccggta ttatctggcg   7560
gcgctgcgtg cgatggcgca gtcgctcgag ggcaggtatg agctgtcatt gctcacgccc   7620
gaggagcggt ccgcgctcct gatctccggt gagccacctg cctccaagcc ggccctggtg   7680
gagaagatct ggagcaatgc ccgtgctcat ccggagcggc aggcactcac ggatgggtcg   7740
cggtccctca gctaccggga actcgcgtca ctcagcgact cgttggctcg tgcgctccat   7800
caggcggagg tgaaacccgg cgatatcgtc gcggtgaacc tccgcaggga cgtccatctg   7860
ccggtcgcgc tcctgggcgt gatgcgcgcg gggccacct acctgccgct cgacaatcgc   7920
ttcccgctcg aacggcaggc gttcatgttg caggacagcg gcgcgaagct ggtgctctgt   7980
gacaatgaga cgcgccccgc ctcgggcgga acggcccggc tcttcaatct ggacgaggag   8040
aagtggcagg accacggcgg cgagcggccg cttccagagc tccacgcgga gtcgatcgcg   8100
tacctgatct atacatctgg ctccacgggc aagcccaagg gcgtgctcat ccgccaccgg   8160
aatctcgaca acttcatcgc gagcatggag aggtctcccg gtttctccca gggcgaccgg   8220
ctgctcgcgg tcacgacggt ggcgttcgac atcgcggcgc tcgagctgtt cctgccactc   8280
tcttgtggcg gtcaggtcgt tctcgcgcca gagcaggtcg gcaaggatgc cacgctgttg   8340
atggagtggt tgaagcggca cgacatcacg gtcatgcagg ccactccagc cacgtggcag   8400
cagttcgtcg acctgggatg gcggggcaaa ccagacctga agatcctcgt tggtggtgag   8460
gctctgcccc cggcactcgc ccgtgggctc ttgacccgct gccgtgagct gtggaacatg   8520
tatgggccca ccgagaccac ggtgtggtcc agctgcatgc ggatcgcgga cagcacccgt   8580
atccggatcg gccagccgat cgcggacacc cggctctatg tcctggatgc ctatggaaac   8640
ccggctcccc ggcagaccgt gggcgagctg tacatcgcgg gcggaggtgt tgccgcgggc   8700
tactggcggc ggccggatct gacccgtgag cgcttccagg atgacccctt cttcgggggt   8760
ccgatgtatc ggaccggcga tctggcgagg atcgattcgc gcaacgaagt cgagtgcctg   8820
gggcgtacgg accaccaggt gaagctgcgg ggttatcgca tcgagctcgg cgagatcgat   8880
gcggccatcc aggagcaccc ggacgtcagt cagtccgccg tgattctccg gaggcactcg   8940
gaacgtggtg atgagctggc cggctactac accctgcacg atgaagcgct ctccaggcgg   9000
gcgaatgagc tctatggaga gcaggtcgtc cgctgggagg ccgtctggtc ggagacctat   9060
ggccggtcga aggagaaccg gggcgcgttg aatctggcgg gttggaacag cagctacacg   9120
ggtcaaccca tgcccgaagc ggagatgcgg gagtggattg acgagacggt cgcacggatt   9180
cgctcactcg gcgcgaagcg gatactcgag attggttgcg gtacgggtct cctgctggcc   9240
cgtctggccc cccattgcga gcggtacacc gccaccgact tctctccggc cgcgctggag   9300
tatgtccaga gcgccatcgt ccctcagctc tctcacctgg actgtgaggt gcaactggtc   9360
cgcgccacgg ccgacaggtt ggagggggtg gaggatgggc agttcgatct ggtcatcctg   9420
```

```
aactcggtgg ttcagtactt cccgagccgg gagtacctcg acaaggtgct cgcggcggcg   9480
atccggaaga cccggcagcc gggtaggatc ttcgtgggtg atgtcaggca tttcggcctg   9540
ggccgcgcgt tccatgcctc catcgccgac taccagtcca agggagcact ggctccggcg   9600
gccctggagg agaaggtcgc gcagggcctg cggaaggaga cggagctcct gttgtcgccg   9660
cgctacttcc tctccctgtc ctctctgggc gtcgcccatg cggagatcga gctcaggcgg   9720
gggacgcacc acaatgagtt gacccggttc cgctatgacg cggtgctgtc cattggccag   9780
cgtccggagc agctcgagac ccgctggtac gagtgggaaa cccatcctct ttccggggat   9840
gagctctcga cgaagttgaa gcaggcgggt gagtgctttg gactccgagc cgtcggcaac   9900
gcgcggctgg cgagagagcg tgagctgctg gggctcgga gtgacgagac ccagggctca   9960
gcgggagctg gcgcgggact cgatccggag cagctctacc ggctggcgga ggctcatggg  10020
tacagggcca agacgagctg ggcctcggag cacgcctatg gcgcgttcga tgtggccttc  10080
atcccggccg gaaagaacgc cacgcccctg ttcgagctgg cgcaaggctc ggcacgtttg  10140
agcaatgccc ccttgctctc acagattgat gtccgggtgg gcgcggagat ccggcgggcc  10200
ctccagaaga acctcccgga gtacatggtc cccgcgcggc tcgttctcct ggattcgatg  10260
ccgcacacgc ccaatggcaa ggtggaccgg agcaggttgc cggatgtggg gcgcaacgcc  10320
gtctcctccg agttcgtcga gcctcggaac gagaacgagc gcaagctctg ccagatgtgg  10380
caggagttgc tgggcctgga gcgcgtgggc gtgagggacg acttcttcgc cctgggcggc  10440
cactcgctgc tcgccacaca gctgatcaca cgtatcaaca aacagttcga gtgcaatctc  10500
agcctgcggg ccctcttcga tttcccgacg atcgagcagc tcgtccggga gattgagcgg  10560
agccggacgc tccagggccc cgccatgccg aagattcagc gccgcaagaa gaattag     10617
```

<210> SEQ ID NO 4
<211> LENGTH: 17841
<212> TYPE: DNA
<213> ORGANISM: Artificial
<220> FEATURE:
<223> OTHER INFORMATION: Seq.-ID No. 4: arg3

<400> SEQUENCE: 4

```
atgcatctcc ccgagcttct tcctttgtcg tttgctcaga cccggttgtg gttcctcgag     60
cagttgttcc ctggccgggc cacgtaccac atcccccagt tctggcgtct gcgggggggg    120
gtgaacgtga gtgccctggt gaaggccttg aagaacacgg cggcgcgtca cgagtccctc    180
cggaccacgt tcgtcaccga gaacggtgag ccgaggcagg ccatccacga ggacatggcg    240
ctggacttcg agtgtgagac gctggatgag cgagggggag agacgctcga ctcctatctc    300
tcggcgttga cggcgcggac attcagcgtc tccgaggggc cgctatggcg tgtgcggctg    360
gtgcggacga gcgctcgtga acaggtgttg gccgtcgtct tccaccacat catctgcgat    420
gggtggtcga tggggatctt cagccgggag gtcagccatc attacaacca ggccatcggc    480
gaaagcttgg gtgagctgag tgagcctccc attcaattcg gagacttcgc ccagtggcag    540
cgggagtggt tgcagggcga gcgtctggag cttcagctgt cgtactgggc ggagaaattg    600
aagggtgccc ctgacctgct cgcgttgcca acggacttct cgcggcctcc agcggcgagc    660
aacaagggca agctctacgg gacattcgtt cccccagagg tcgtgcagcg cctgaaggac    720
ctggcccggc aggagaaggc caccctgttc atggtgctca tggctgcctt caaggtgctt    780
ctccgccggt attcgggctc ggatgacatc gtcgtgggaa cgccgattgc caaccggcat    840
tatcccgatg tcgaggaggt gttcgggtac ttcgcgaaca ccctggccct tcgcaccccg    900
```

```
ctggagggca gcgcgagctt caggcaggtg ctgcagcggg tgaagcactc gacgctcgag    960
gcgtatgagc atcaggacct tcccctcgag ctcgtcgtcg acaagctggg cgtggagcgg   1020
gacctgagca ggcatcccgt gttccaggtg atgttcgctc tcctgaccga aggccgctcg   1080
accctgggtg ttggcaagac ggagcttcgc ctcgaaggac tggaggtgga gagcctgcgg   1140
ggcgtcggtg attgtgccaa gttcgacctg gcgctgctcg ccgaggagac agagcagggt   1200
ctgttcctcg agttcgagta ttcgaccgac ctcttcgaac aggcgaccat cgagcgggtt   1260
gcccgccact tccagaacct cctcgtggag gtggtcgccg ggccgggatc gtcgatcgat   1320
gactacttcg tcctgagtga tgcggaaatc gccgagcgga tcgcctgtct ggatggatat   1380
ggactccccc acgacaccga gatctgtctg catcagtggg tggagcgctt cgcggcacga   1440
acgcctcagg cgatcgccct ccgggatcag acggggtcga tgacctaccg ggagttgaac   1500
gaggaggcga accggctggc gcgctgtctg ctcgagcgtg gtctgggcca tggacagatt   1560
gtcgggctcg ccctccctcg gacgagggag ctcatcgtcg cgatggtcgc ggccttgaag   1620
gcacgagcgg cctatcttcc gctggacctc ggctatccga gccagcgtct gcgcttcatc   1680
ctggaggacg cggagaccgc cgcggtcctc accacccggg cgcatgtcga gtccctgcgg   1740
gggcactgca agcacatcat cgccctggag gatgtggcgg cggaggtcgc tggccagtcc   1800
gcggggaacc tggacctgga ttacgcgtcc ggggatctgg cgtacctgat ctacacctcg   1860
ggctccacgg gcaagcccaa gggcgccacg atctgccacc gcaatgtgac gcggctcttt   1920
cccgatccgg aacctctcta ccggttccgc ccggatgatt gctggacgtt cttccactcg   1980
tgcgcgttcg atctctctgt ctgggagatc tggggcgcgt tgagccacgg ctccacgctc   2040
tccgtggtgc cagccgaggt ggctcgatcg accgacgagt tccgcgagtg gctggtcgcg   2100
catcgggtta cggtcctcaa ccagacgccc tctgcctacg agcagcttct ctcgtatatc   2160
agcagggagg gcgggagcga cgggctgcgg ctgcacaccg tgatgcttgg cggcgagggg   2220
tggggagagg ccttggcgga gcgccatcgc cagctcctac cgcatgtctc cctttacaac   2280
gagtacggtc cggcggagtg cgccgtctgg acgacacacg gctgcgtcta tgatgcggag   2340
acggtgcagt cgtatccgct ggatctgggg atcgcgcaca gccagagtct ggccctcatc   2400
ctgaacgatg gtcatcgtgt taccccgacg ggcgtcgtgg gcgagctcta cctcggcggt   2460
gagggtgtca cccaggggta ttggaagcgg ccagagctga acaaggagaa gttcgtccac   2520
gtctcccttc ccggaaaggg caacgtccgc ctctacaaga cgggcgatct cggaaggtac   2580
aagagcaacg gacgtatcga attcatcggc cggcgcgatc accaggtgaa ggtgagaggc   2640
taccggatcg agctgggtga gattgagagc atcctccgga gccttccggg tgtccgggat   2700
gcgctcgtca tgttgagcga gagcggccgt cagctcgtgg cctacgtcgt ggtgggtgag   2760
ggcgggacgc tcacgcagga gacgatcgcg taccagctca aggatgcgct gccagcctac   2820
atggtgcctt ccttcttcgt gctcctggag cgcttcccga tgacgaataa cgggaaggtg   2880
gatcgggccg ccctccccaa gccccacgcg acgacaggtc agtcggttgg ggctcaggcc   2940
ttcgtcgcac ccagcgggcc actcgaggaa ggtatcgcca gtgtgttctc cgagctgctg   3000
gcgatcaccc ccttctccgc ggagggcaat ttcttctcgt tgggtgggca ctcgctgctc   3060
gccacacagg cggcggcgaa gatccatcag cgtctgggca tcgcgtgccc ggtgcgtacc   3120
ttgttcgaga gcagcacccc gagggcgttg gcctggaagt tgggacagga gggcacgaag   3180
caggccgtgg ctggagccgc gctgcccgtg ctccagccga atgagcagga ccgtcaccag   3240
cccttcccgc tgacggacat ccaggaggcc tactggattg gccgcaaggg ggcactgacg   3300
```

-continued

```
ctcggggaag tctcggtcca ttgctacatc gagtacgaca tggacgagct ggacgtgggt   3360
cggctggagc gggcgctcaa ccgcctcgtt cagcgccacg aggccatgcg tctggtggtg   3420
gaggagagcg gacagcagcg ggtgctggaa agcgtcccct tctacaagat cgaggtgacg   3480
gagctgtccc gggggtcgcg agaggaggag gcacgtgctc tcgccagcgt gcgtgagcgc   3540
atggctcacc aggtgctccc cgcggatcgt tggccgctgt tcgagatcag ggcgagcagg   3600
gctcatggct tctggcgtct gcacgtgagc ctggatgcgc tcgtgctgga tgcctggagc   3660
ctgaatctga tcttcaatga gtgggcccgg ctctaccgcg atgaggagac ccggctcgag   3720
cccctgaacg tcagcttccg ggactacgtc atcgccgaga aggcgttcaa gagcacgcag   3780
acgtggcaga aggcgaagga ctactggctc gcacgagtcg ccacgttgcc ggatgcgccg   3840
cagttgccgc tggcgcagag ccagacacgg ctcgacgcgc agcacttcaa tcgcgagcag   3900
aagcgcctga ctcccgaggc cctgcggtca ctgcggaagc tcgcggacaa gcacaaggtg   3960
tccctgtcca gcgtcctggg cgcggtcttc gccgacgtcc tgtcactgtg gagcagcaag   4020
ccgcacttca ccctgaacat gacgctcttc aaccggctgc cggttcatga gcagatcaac   4080
gacatcgccg gtgatttcac gtcactcaat ctgctcgagg tcgactggcg cggaagtgac   4140
gtgccgttca tcgagcgcgt ccgcaaggtg caggagcaac tctggagcga cctggatcac   4200
cggttcttca gcggcgtgca ggtgctgcgt gagctggccc gggctcgcaa caacccggca   4260
gtggccatgc cagtggtgtt cacgtgcctg ctgggatcga ccgaagggga gggacaggct   4320
cacgagtggg agcgtctgtt cccgaacgag gtcttcaaca tcacccagac tcctcaggtg   4380
tggctcgact accaggtcta cgagtcccag ggcgagctgg tggtctgctg ggattatgtc   4440
gagggtctct tccccgaggg actggtgggg gccatgcacg aggcctacat caccagcctc   4500
gagaggctcc tgcgcgagga gagcgcctgg aatgagacgc gcctgacgaa tctccccgag   4560
tcccagcgaa tccggcgtga ggaggcgaac gcgacggcct ggcgtgagcc ggaactgctc   4620
atgcatcagt tgttcgagcg ccaggtcggc gtggctcccg atgcgaccgc ggtcatcgac   4680
agcgagggaa gttacaccta ccgccagttg aatgtggccg cgaaccggat cgcacgaagg   4740
ctcgcgtccc tgggtctgga gccgaacgag cgcgtcgccg tgctggcgcc gaaggggtgg   4800
cggcaggtcg tggcctgtct gggtatccag aaggctggcg ccgcgtacct gcccgtggat   4860
gggagtgcac ccgccgagcg gatcaacaag gtcctggagc ttggacgggt gagggccgct   4920
gtcgtcgcgt ctctcgagta cggcggggcg ttcggaagca atgccctcat cgtcctcgat   4980
gacgggctgc tggcgcccgc ttccggaacg gaggatgtga gcaatccggc gccgaagcag   5040
accttggcgg acctcgcgta tgtgatcttc acctccggtt cgacgggaac acccaagggc   5100
gtgatgatcg atcaccgggg ggcggtgaac accctcctgg acatcaacga gagattcggc   5160
gtgcgccagg atgacagggt gctcgcgctc tcgagcctga ctttcgacct gagcgtctac   5220
gacatcttcg ggttgctggc cgctggtgga gcggtcgtca ttcctcccga ggcccatgtc   5280
aaggagccgg cggagtggtg tcactggctc gtccagcacc aggtgaccgt gtggaacacg   5340
gtcccgatgt tcatgcagat gctcatggag ttcgtgggcg cactgccagt ggccgaacgg   5400
gaggcgctct cgcggacgct ccggctggtc atgatgagtg gcgactggat tcccgtcgag   5460
ctgccgaaca cgatcaagcg ggtcttccaa cgcgaggacc tgcgggtgat gagcctcggt   5520
ggcgccacgg aggcgtcgat ctggtcgatc gcctacgaga tcaaggacgt cgcgaaggac   5580
tggacgagca tcccgtacgg gaagccgctg cggaatcaga ccttccatgt cctggacgaa   5640
gggatgcgtc ctcgtccgga cttcgtgcca ggccagctct acatcggcgg catgggcgtc   5700
```

```
gccctcgggt acttcggaga cgaggcgaag acagccgcga gcttcctccg ccatccccac   5760

accggagaac ggctctatcg gaccggagac ctcgggcgct acctggccga cgggaacatc   5820

gagttcctcg gcagagagga tctgcaggtc aaggtgggtg gccaccggat cgagctcggt   5880

gagatcgacc accatctgca caagtgcgga tggatccgtc aggggttgac gcacgtcttc   5940

aagcccgatg gcaggaaccc gcagctcgtc gcctacctgg ttcccgaggg agtgacaggc   6000

aagagcgagc aggagcgtgc ggaagagctc tcgttcaagc tggccgggca caacctcagg   6060

aagacggggg gcgcgggcca tcggctcgtg acggagctcg aacccaaggt ctacttccag   6120

cgcaagagct atcgcgtgtt cgccggagag gagtcccggt tgagccagct ggaggcgtgg   6180

ctgcggagcg cgctgctccc gggcaagcct ctcgcgacgg agcggcggga atggacggtg   6240

gcggagatgc tcgcgccgct gctggctctt cgtgaggacg gcctgctgct gccgaaatac   6300

cgctacggtt ccgcgggctc gctctacccg gttcagacct acctcgtcat gggagagggg   6360

cggaaggagc tcgcccccgg cgtctattac ctcgaccccg tgaagcacga gctggtgcgt   6420

ctcgcggacg gcgcgctggc ctgctcctgg ttgagccggc gaggtgttcc cctggcgctg   6480

tgcttcgtcg agaagcgctc ggcgatcgaa cccctctatg gcacgcgcag tgacctctac   6540

agcgccatcg aggccgggag catggcggcg ctcgtcgcct cctcgaccgc cgcggccggc   6600

atttcgtggc ggacccggtc cgcaccagac ctggaggaac tggcgcccgt cgtcctggag   6660

tccgctgact gctccgcgat cgcggtcctc gagccccgcg agctccaggc cctcgacgag   6720

cgcggcaagg actccgatgt ctccgtcctg atgtacgtga tgcgagggtc ggagcatggc   6780

ccacggacgg gttggtaccg ctggtccggg gaccacttcg aggccttcag tgctccggcg   6840

ctcagcatgg tgccgtcgaa ccccgcgaac tggtccatct gccagaatgc gtccttcgcg   6900

ctcttcgtga tggagggaaa ggcacagccg cggacctcct cggcgctctt cacggggcgt   6960

ctgatccagt ccttgatgga gaaaggcgtg gggctgggcc tgggtggctg ctcgatcgga   7020

gaaatggacc ccgagggcgg gcggctcctg agagaagtgc atgacggtga gttcgttcat   7080

gccttcttcg gtggaccggt ggattccgcc cagatctccg cggtgggcac ttccgaggcg   7140

gagccgttcg agcaactcgt gaagcggaag acgcgctcgg tcctcgaggg ctcgcttccc   7200

gggtacatgg ttcccgacca ctacgtcctg ctcgacagct tccccctgtc gagcaatggc   7260

aaggtcgatc gttcccggct cgccgccccg gagttggaga gaccccagaa gcaagacgcc   7320

ctggtgcggc cctggaacag caccgaggcg gtcatcgcga gcatctgggc gcagttgttg   7380

ggcgtggagc cggacgcggc cgacaacttc ttcgcgctgg gcggccattc gctgaccgcc   7440

acgcagctct gtacgcgtct gcgagaggcg tttggcgtag aggttcctct gcgcgaggtc   7500

tttggtaggg cggatgtgcg gtcccaggcc agcatggtcg agggcctgct gaaacagcac   7560

gtcggtcgtg gggcttcgat tccccgcaga gccgggacgg gccggtccgt ggcgtcgtat   7620

gcgcagaagc ggctctggtt cgtcgagcaa ctggcggaga acggttcggt ctacggaatg   7680

ccggtcgcgg tcgcgctcca gggccccatg gactgggatg ccttcaagaa ggcgctcgcg   7740

ggggtcgtgg cgcggcatga aatccttcgt acgaccttcc acatggagca gggggagttg   7800

tggcaggtga tccacgagga gatcaccgcc cccttcgaga cggagcagtg ccccgagggc   7860

tccgtgatgg agaagcgcgc gtatgtgcgg aagcggatgc gcgagctggc gcgggtgccg   7920

ttcgacttga gcaccggtcc gctgctccgg ttccatgcgt tcgcgctgtc cagggagcag   7980

cacatcctgt tcggcgcgat gcaccacatc atctccgatg gctggtccgt ggatgtcttc   8040

cagtcggagt tgagcgctct ctacaacgcg gcgctgagcg ggagcacgcc ccagttccag   8100
```

-continued

```
gagctctcca tccagtacgc ggatttcgcg gcctggcagc gggattggct ccgtgggccg   8160
cgctccgaga agcagctcca gttctggaag gactccctcg cgggtgctcc ggagctcctc   8220
caactcccca ccgatctccc caggcccgaa cgtcagagct tccgcggtgg cgtggttcgc   8280
aggacgctcg atgcgcagtt gaccgcggag atcgactcgc gctgccgtga gtggggcgtc   8340
accccccttca tgttctatct cgcggcctac aaggtgcttc tgtccaagct gagtggacag   8400
gcggacattc tcgtgggcac cccggccgcg aaccggcact actcccaggt cgaacgcctg   8460
attggttact tcgcgaacac gctggccatc cggagccgcg tcgaggggca gcggagcttc   8520
gccgagtatg tccaggcggt tcgtgaagga gtgctggcgg cgaacgagaa ccaggacgtt   8580
cccttcgagc aggtcgtcga gagcctccag cttcgtcgca gtctggcgta ccagcctgtc   8640
ttccaggtca tgttcgtgtt cgagaacgag gggcgctcca gcctttcgtt gaacggcgtg   8700
agcgtgcagc cggtatccct ggacgcgcag gtcgcgcgct tcgatctgac gctgctcatc   8760
cgcaacgcgg gagacgcacg ggagatctcc ttcgagtatt cggaggacct gttcaagcgc   8820
gaaacggccg ctgaatggct cgatggagtc atcagcctgg tggaagccgc gacgcgggac   8880
agcagccagc ccctggccgc gctgccctcg atgtccgagg ccacgctgga gaaggtcctc   8940
ggccagttca gccggggaga gcgcacggcg agccccaagc tgtgtctgca tgagcagttc   9000
gagcgtgtgg tggcccggca gggagagctc tgcgccattc aaacgcctcg cagtgagatc   9060
acgtacgagc agctcaacga cagggcgaac cgcgtggcgc gtctgttgtc ctcgcatggg   9120
atccgcaagg gggacgtggt cgcgctctgt ctgaagcgct cgccggatct gttcgcctgt   9180
tacctggcgg tgctcaagct gggtgcggtg tatgtggcca tcgatgggga gtacccggaa   9240
cgccggatcc agcacatgct gaccgacgcg ggcgcgaagc tcgtcgtggc ctccccccgtc   9300
tatgcggaca agctgggaac ggccccggtc ctcgtgacgc tggaggagtg tgaggaccgg   9360
ctggagtcga tggcgggctc caacctctcc gtcaaggtct ccccggagga tgtggcgtac   9420
atcatctaca cctcgggaac gaccggtctg cccaagggcg cgcgggtcaa gcatcgcggt   9480
gtctccaacc tcgtgctcgc gcagcaggag tacttcgtgg cggggcccgg aaagcggctc   9540
ctgcaattcg cctcgtgcag cttcgacggg gccatctggg agtggacgac cgcgttgctc   9600
aacggcgcga ccctctgcct cgtcgcggag agcagcgccg aggtcgtcag ccgcctcacc   9660
cgccgcgacg agcagccgcg gatcgacatc gccgccctgc ctccgtccgt ggtcgccagc   9720
cttccggacg attgcctgcc aggctcgag gtgctgctgg tcgcagggga gagctgcccg   9780
cggggtgtgg tggaccgctg gtctcggcgt acgcggatgt tcaacgccta tggcccgtgt   9840
gaagccagtg tgacgtcgac gatgttcgag ttcgatggca ctcgcggtgc gtcgaccatc   9900
gggcgtcctc tgcgcaactg cgatgtctac atcctggatg agcggatgct ccctgtccct   9960
ccaggagtgg ccggagagct ctgcatcgcg ggactgggac tcgcggaggg gtaccacaac   10020
cgggcggagg agacggagcg gcggttcgtc gaggcgagca tcggctcgga gaccgtgcgg   10080
atgtaccgca cgggtgatcg tgggcgttgg gcgagcgacg ggaacatcga gttcctgggc   10140
cgcctcgaca atcagatcaa gatccgcggg attcgcgtgg aaccggatga ggtccgcacg   10200
cagctcctcc aggtgcccgg tgtggcccag gcggctgtcg tcgtcgatcg ggaggggcag   10260
gagacgcggt tgctcgcata cgtcgtggcc tcgccggagg tcccgctcga cctggagcac   10320
gtgcgcaaac ggctacgggc cgcgctgccc gaggccctgg ttccctcgtg gttctgcccg   10380
gttgctacgc ttccgatgac gctcaatggg aagctcgatg tggaggccct tcccaggcca   10440
ggcgaggagc ggaccgaagc gcggttcgaa gagggtgcca cggaggtgga gcggaagctc   10500
```

```
caggccctca tcgcgggcgt gctggagggc aggcggctcg gccggcacga cgacttcttc  10560
cgaaacggag gtcattcgct caaggcgatc catctcgtcg cggagatccg gaaggaactc  10620
ggtgccgagt tggcggtgaa gaccatcttc gacgctccga cagtggccga gctggcccgg  10680
gtgatcgaat ccgaaagaag acaggaaggt ccgaccgcct cgcgtccccg cctggagggc  10740
tcccggttca cgctgtccgc cctgcagcgg cagatgtggc tggccgagaa ggtgttgcag  10800
cggagcggcg cctacaacat gccgctctgc ctggagcttc gtggcgcgcc ggatgcttcc  10860
gccctgcaga acgccgtcga catgctcctg cagcggcatg gtgtcttgcg gtggcagttc  10920
aaggaggagt cgggcgagcc ctatgcggag gattgtggcg tcgacacggt gacgctcgcc  10980
acgctcgact ggagggagct ggggcagcag gagaaggaca ccgcactcgc cgggctcatc  11040
gcgacgccgt tcaacctgtc tcaggggcct ttgtggcggg gcgcgctcat ccgaatcgga  11100
gaggagcgct tctggctcct gctctgcgcc catcacctgc tggcggatgg atggtcgctg  11160
ggactccttc tcggagagct ggccgagctc tacaacgcgc gagtaggtca tggcacggcc  11220
cggttgccgg cgcctggcac cgagtactcc cgctatgtcg agcagagtgt cggggatgag  11280
cgggagctcg agcgtcaact cgagttctgg cgtcatcagc tcgagggtgc tccgcagcgg  11340
ctggcgttgc ccatggagtt gaagcggtcc ctgtcacccg gaaaggccgg tgccgtcgac  11400
ttcgaggtgg gtccggagct gaccgctcgt ctccgtgagc tggcggaaca gcggggcagc  11460
agcctcgtca tggtgctcat gagcacgtat caggccgtgc tcgcccggtt cgcgggcgcc  11520
gatgacgtgc tcatcggaac gcctgtcgcg tgccggcaca agccggagct gttgaacacg  11580
atcgggctcc tggtgaatac cctccccatc cgtttgagcc tcaccccgcg tacgacattc  11640
gccgaggcgc tcgcgcaggt ccggcagcgg ttgctcgagg ggatggctca catggacgtt  11700
cccttcgagc gcatcgtctc cgcggtcgca caggagcgcg agcccggtgt ccccgcgctc  11760
tgtcaggcga tgttcgtctg ggaggagggc gctcgtggtg acctgaagct tcggggtctc  11820
gacgtctcac tgaaggcgac cccggtcacc tccgcgaaat acgacctcgc cctcttggcg  11880
agcgaacagg acggccgtgt cacggggcgg ctcgagtatc ccgaggggct ctatgaccgg  11940
gcatccgtgg agcagctcgc cctcagctac gtgaagctgc tctccgagat ggcgaaggat  12000
ctggagggga tcgtcgcgca ggccgagctg atgtcccagg agcagcggcg gcaattggag  12060
gcgtggttcg agtaccggcc ggagttcctc gaggctccca acctccacac gctgatcgag  12120
cgtcaggcgg ccaccgcgcc cgcgtcgtca gcgctgcgct acaagggtga gagctacagc  12180
tacgagtggt tgaataccca ggccaataga ctggcgcgct acctcggggc tcggggcatc  12240
gggcgcggca gcgtcgtcgc gctgtgcctc gcgcgctcgc cggagctcgt ggtcgcgtgg  12300
gtggccgtgc tcaagtccgg ggcggcgttc gtctcgctcg atccccatat gcctcaggcc  12360
aggaggcggt tcatcctgga tgacagcagg accgcgctcg tgctgtcgca cgccgccttc  12420
gcggaggagc tcgggaccgg tacggacatc gccgtctggg aagaggtggc gaagcagctg  12480
accgggctcc cggcggagaa cctggagctg gaggtccgtc aggaggagct ggcgtacctc  12540
atctacacct cggggaccac gggcaatccc aaggggacca tgctggcgca ccgggggatg  12600
atcaacctgg cggtcagcga gaagcagcgc agcggaatgg gtcctcagag caaggtcctc  12660
cagttcacca ccgccacctg tgacggttcg atctgggagt ggacctcggc cctggtgaat  12720
ggcgccgagc tctggctgtt ggatgcgagc aatccgcagg agcaggtggc tcaggccatg  12780
caactcctgt cggagcctgg gattaccacc gtcgcgctga cgccgagtgt ggtggagctc  12840
ctccccccgg aagcgatgcc cacggtgcaa tcactcaccc tggcgggtga ggcttgcccg  12900
```

```
ttggcgctgc tggagaagtg gtccgcgagg atccccggag tcgccaacgt ctatggtccg  12960
accgaagcaa cggtgaccac ggccacattc cccttccggc ccggctatcc cgcgaacacc  13020
atcggcaagc cgctggcgaa cgtgcaggtc tacatcctgg atgagcacgg caagctgctc  13080
cctccaggcg tcatcggcga gctctgcatc gcgggtgtgg gtctggctct gggctatctg  13140
gatcgcgacg agctgacaca acggaagttc gtcacccatc cgattggacc tcgaggcgag  13200
cccgttcgcg tctaccgctc gggtgacctg gcccgctatc tgccggatgg ccatatcgtg  13260
ttcgagggcc gcagggacaa tcaggtcaag gtgcgaggct atcgcgtcga gctggatgag  13320
gtggcctggg tcctcaagca gcacccgcag gttcagcagg cctcggtgat cgtctcgcag  13380
gccgggaagc ggtatccgta tctcgttgcc tacgtcgtgc cgcgcacccc gccgtcttct  13440
ccggccagcc tgcgggcgga gctgcgtgcg tacatggccg agcggttgag ccactacatg  13500
gttccggagg cctacgtctt catcgagtcg ctgccgctca atcgctccag catgaaggtg  13560
gaggtctcgc tgctgcctcc tcccgagggg gactccttcg ttcgtgacac gctggtgccg  13620
ccagagacgg ccgtggagaa ggagctggcc accctgtgga tggagctcct cggtgtgggg  13680
agcaccggcc gtcatgacag cttcttccgg ctcggcggca actccctgct cgccgtcaag  13740
ctgggtcacg ccatcggcga gcggtggggt tgtgacatct ccctcccacg tatcttcgag  13800
aacgacacgt tggcggcgct cgcgcggtgc atcgaggccg acgagagaag gagccatgac  13860
ctccagctcg ccagggccag tgagcgcgag agctggcccc tctcttttgc tcagggacgg  13920
atgtggttcc tcgagcatct gacccagggg agctccgcct accacgtgcc actcgtcctc  13980
cggctcatcg gcaaggtctc gttcgagcgg ctcgcccagg ccttgagcgc gttggtggtt  14040
cgccatgagg tcctgcgcac cgcctatgtc gaagacggga acacgctgag ccagaagatc  14100
ctcgacgccg ttgccgtcga gatggcgagc agcgacctga gcccgatcgc tcccagtgaa  14160
cggcaggcgg ccgtggatcg tctcctcggt gcggatctcg cgcggccgtt cgcactggcc  14220
gcgggcgaga acgtgagggc acggctcgtg cgcttctcgg aggacgagca cctgctctgc  14280
ctctgcctgc accacatcgc gttggatggt tggtcgatca gcgttcttct gcgggagctg  14340
ggttcgctgt accgggggca gccactccaa cccctgccgc tgcggtacgt ggacttcgcc  14400
tgctggcagc gcgacgtcct cgagaagcgc ttcgcggagc agctggacta ctggaaggcc  14460
gagctgcggg agctcccgcg gcagctcgag ctgccatggg atcatccccg tccgcccagg  14520
caggactacc gtggtgcttc cgcgcgtcgc ccactgtccg ggaactacg agccgcgttg  14580
aagcaggtgg ccgagcgcta cgatgtgacc gacttcatgc tctacctgac gtcgttccag  14640
ctctggctcg gacggctcag caacagctgc gatgtggtgg tcggcacacc ggtagccaat  14700
cgccactaca acggcgtcga gtccatcgtc ggcctgttcg tcaacacgct gccgctccgc  14760
cttcggtatg acggctccga gacgttcggc ggcgtcgttc gcaggatgaa gtcgaaggtg  14820
ctggaggcgt acagccacca ggatgtgccc ttcgagtacc tcgtggacca tctggaagtg  14880
cccagggagc tgagccacgc ccccatcttc caggcgatgt tcctgctgca ggacgagtcg  14940
gggcgcgaga tcgacctggg tgacgtccag gggcggatcg ctcccgtggc tggcacggtc  15000
gccagattcg atgtgtcgct cctggttgag ttcgatgagg aaggcgcgga gctgaatctc  15060
gagtacgcga gcgctctctt caggcccgag accatcgacg agtggttgga gagcttcgag  15120
ctgttcttgc gcgcgatcgc ggcggacgcg gaggctccgg ttcggcggtt cgagctgttg  15180
ccgccgcgga tgcggtcctt cctgtccgag gtgggcaccg gaccccggcg agagtatggg  15240
agccttcctc tgcccgagct cgtagcggag caggcgaagc atggcggaca gcggatcgcg  15300
```

```
gtcgagggtg tccgggaatc gtggacctat ggtgagctcc tcgccgccgc ggagcgtgtc  15360
gcggccggcc tgcagcgccg cggggttcgt cctggcgacg gggtggcgat cgcgctgcct  15420
cgcgaccatc ggttgccctc cgccatgctg ggcgtcctga aggcaggtgc cttctacgtt  15480
cccctggatc tcacgcatcc ggagcgcagg ctccagtaca tcgcggggga tgcgaaggcg  15540
cggttcgtca tcacgggagg cgagacccgg ttcggattcg acatccctcg tgtgaacctg  15600
gacgagctgt tggaggagac ctcggaagcg cggccggtgc ccatcgcacc gtcgagcctg  15660
gcgtacgtca tctacacctc gggctccacc ggtgaaccca agggcgtcat ggtgagccac  15720
gccagcctct cgaacttcct gcacgcgatg gtggaggagc tcggcttcgg gccggatgag  15780
cgtctgctgg ccatcacgac gatcgcgttc gacatctcgg gcctggagct gttcctgccg  15840
ctcatccgcg gggctcgcgt cgtgatcgcg gacgaggact ccacgaggga tccgcggctc  15900
ctgtccaggt ggatcgacga gcgacggatc tccgtcatgc aggccactcc ggcgacctgg  15960
cggatgctca tggatgcctc ctgggtggca cctggatcct tcaaggcgct ggtcggcgga  16020
gaggcgttgc cgcggaacct ggcggacttc atgacgagcc gggtgagcca ggtctggaat  16080
gtgtacggtc ccaccgaggc gacgatctgg agcacgatcg cgcggctgaa gtcgggtgag  16140
cgggtccaca tcgggcggcc cctggcgaac accgaggcct tcgtgctcga tgatgggttg  16200
cgagccgtgc ctcgcggaac cctgggcgag ctccatctcg gtggttccgg tctggccacg  16260
gggtacctgg gtagggagga gctcacccgg cagaagttcg tgcatcaccc ggagctcggc  16320
cggcggctct acaagaccgg agacctcgcc cgggtcttgc cctccggcga catcgagttc  16380
gtcgcccggc gggatgcgca gctgaagatc cgtggcttcc ggatcgagcc gggagaggtc  16440
gaggccgtcc tgagcagggt ccccggggtg gcgcgagtca cagtcctgcc cgtgggggag  16500
ggggagggca cccagctcgc cgcgttccta ttgacggggg atgagcggct ccaggcccag  16560
gcgagagcac tcgcggagca gcaactgccc gaatacatgc ggcctgcccg gtacgtggtc  16620
gtgcccgagt tcccgctgac gcccaacggc aaggtggata cgaaggcgct gcgggcgctg  16680
gtctcggagc aggtggaaga ggcggcgggt tccgcgccga aaaacccgat cgagttcagg  16740
atctcccggt tgtggtcggc gctcctgggc gtccgccatc cgggcacgcg ggacaacttc  16800
ttcgcgctcg gggggcacgtc actggccgcg gtccggctcg ctcgcgagct ggagagcgaa  16860
ttcggtatcg aggtgcgggt cggtgacatc ttccggaagc ccacgatcgc ggagctcgcg  16920
ggtctggtgg agacgcaagg ctcggagcgg gtcctcgagc ccctcgtcct cttgagccgg  16980
gagcagcaga agccgcccct cttcgtgatc caccccgcgg gtgggatggc gtactgctac  17040
gccgggctcg cacaggaact ctccggattc acggtccacg gcctgaatca accgcactac  17100
tacgagctgg agcaccgctt cgagacgttg gcggagatgg cggcggatta cgtcgccaga  17160
atcaagcggc tccagccgac cggaccctac cgtctcctgg gctggtcgtt tggtgggacc  17220
ctggcctatg agatggcgag gcagttggag caggcgggag aggccatctc cggcgtggtg  17280
atgctggacg cgcatcacgt ctcgccgctg ggcgcgaacc tgccaacggt cgatgtctcg  17340
gcgatgctgg ccaacctggg tctgggcggc gagatggccg acccctacct ggagaaggac  17400
atccgcgaga gcgagcggct ctcccgggac tacaaggcct cgcccgtgcg cttccccgtg  17460
ctcctgttca agcccaccga gcggaatggg ttcgaggaga ggctttacgc ggacctctac  17520
aacggttgga gggagtgcgc ggagaactcc gtggtgcgca gtgtcaccgg cgatcatggt  17580
ggagtcctgg accggcgcaa cgtcagcgag ctggccaggg tcgtcgaggc cttcctgtca  17640
ggaggttacg gagtgctcct gcgtgaagcg gttcagcccg ccctcgcgtt cgcgctcgcg  17700
```

gagcgtgacc gtttcgtcgc caggcggctg gtggagcaac tgccgcggga tctggtggag 17760
cgctggctga agtcggcgat cgactgtctg ccggagtcag tccggccaga ggggtcgttc 17820
gttcaggcgc tgctcgaata g 17841

<210> SEQ ID NO 5
<211> LENGTH: 1011
<212> TYPE: DNA
<213> ORGANISM: Artificial
<220> FEATURE:
<223> OTHER INFORMATION: Seq.-ID No. 5: arg4

<400> SEQUENCE: 5
atgattccca gcagcctcga aaaggccatc tacggtgtgt atgcaacgca tgccctgcac 60
ctggcggaca agcacaacgt cttcgcgtat ctggcggaga agggcgccgc ggcgcctgga 120
gagatcgcga aggcggtggc ggtcgatggg gagaccctcg agaggttgat gctcgtcctg 180
ggtgccttgg agctcgtcca ggccgggtcc gacgggaagt accggttgcg tgaggggatg 240
gggccctatc tggacaagaa ggatccccgc tacgtgggtg gtttcgtcac gcatctcatc 300
aacagcacgt ctggccggat gggacacctg gatgcatacc tgtccaaagg caaggcggtg 360
gtggacgcgg ctctgccttc gccgttcgac gtcatctaca aggacgaggc gtcgacgaag 420
gagttcatgg acgccatgtg gcagttgagc ttcgacgtct cacgggagct cgtgaagctg 480
gcgggtctgg attcctgccg gcagctcgtg gatgtgggcg gcgcgagtgg gcctttctcg 540
gtcgccgcgc tgcagcactc cagggagttg cggtccaccc tgttcgatct gcccaaggtc 600
gggcgctacg tcgatgagac ccgccggacc tacgggctcg aggagcggct gcgtttcgtc 660
ccgggcgact tcttccggga ggagctcccg gagggggact gtttcgcctt cgggtacatc 720
ctctcggatt gggacgatgc gacatgtctc gagctgcttc gaaaagccca tcgagcgtgt 780
agggcgggcg ggcgcgtgct cgtgatggag cggctgttcg atgaagacaa gcgagggcct 840
ttcgcgaccg ttttcatgaa cctctcgatg catgtcgaga cccagggcag gcacaggacc 900
gcccgggaat acgtgggcct gttggaggcc gcgggtttcc gtgggtgcga ggtgcggcgc 960
tcctcgcgcg acaagcatct ggtcatcggt ttgaaacacg tcaccacctg a 1011

<210> SEQ ID NO 6
<211> LENGTH: 1152
<212> TYPE: DNA
<213> ORGANISM: Artificial
<220> FEATURE:
<223> OTHER INFORMATION: Seq.-ID No. 6: arg5

<400> SEQUENCE: 6
atgcgggttc acctgccagg cgagtgcgaa gacattgtcc ggctgcaaaa gagagcgggc 60
cgtgctgccc tgctggagtc cgagtgcgag gcgctgtcgc tgctgtatga ccgggtctcg 120
gtggagggcc cctccgagga ggaggagatc ctggccctgc tgacgaggcc cttcagccgg 180
cgtctggcca tcccggagta ctaccagtac accagcctgc acgtgtacgg ctggttcctg 240
tcccactacc ggagggatcc gctccgcggg tccctcgtcg cactgcacac gaccctggtc 300
gatctgctgt cggtggagga gcagggagcc cggctcggcg aggccacgcc ggcctatatt 360
catgagcgga ttcgcgggtt gcgaggtctg ctcgggcagc tcgatgagat ccccgtggat 420
cggaacgggc ccctgttcgt cgcggacgtg ctcaagggca gcaagaagga tgctcaggag 480
cagtggcgcg ccttcgtcct ggcgcgttgt acgggattcc cgaagtcgca agtacacgat 540
gagtacatct tcctccggtc ggtccacgcc tgtgagatcg tcttcttcca ggtgcggtgg 600

```
ttggccctgc gcatctcgga gatgatcgcc gtggaccgga aggaagccgt cttcctcctg    660

gggcagttga cgagcttcgc agagctcctg aacaagatct tcgacgtgct gaagaccatg    720

tcgcccgagc gtttcatgag ctttcgagca caaacgggaa acgccagcgc agttcagtcc    780

ctgaatcatc acgcgatgga gatcgccgtc tttggcttcg accccgggcg ggcgagcgtg    840

ttcgatggct tcgagcatct gaagcggttg aacgagccgc tgtttcggga gcacgcgtcg    900

ttgcggagtg tcgtcgaagc cacggcggac ggggcgctgg cggaaggatt cgcgaaactc    960

gataggtgtc tcctccgctg gcggggaggg cactatgggt tcgcccggaa gtacctgccg   1020

gttgacatca agggctctgg aggaacggag ggggctccgt atctcaagag gttcatcaag   1080

aaggacgact gtcagtcagg cgggcagcgg ccgggtaccg acagcgagct ggcgcggttc   1140

ttcttctgct ga                                                       1152


<210> SEQ ID NO 7
<211> LENGTH: 682
<212> TYPE: PRT
<213> ORGANISM: Artificial
<220> FEATURE:
<223> OTHER INFORMATION: Seq.-ID No. 7: Arg1

<400> SEQUENCE: 7

Met Cys Cys Ser Arg Tyr Ala Ser Arg Ala Phe Leu Met Gly Gln Thr
1               5                   10                  15

Asp Leu Leu Leu Leu Asn Ala Ser Asn Leu Pro Gln Leu Pro Ile Tyr
            20                  25                  30

Pro Tyr Ala Phe Val Gln Val Ser Ala Ile Ala Arg Arg Phe Gly Leu
        35                  40                  45

Ser Val Arg Arg Leu Asp Leu Leu Gln Val Arg Arg Glu Phe Trp Arg
    50                  55                  60

Pro Met Leu Arg Glu Leu Ile Gln Arg His Arg Pro Arg Met Val Gly
65                  70                  75                  80

Ile His Leu Arg Gln Gln Asp Thr Val Leu His Phe Asp Tyr His Asn
                85                  90                  95

Pro Gln Met Gly Val Met Ala Gly Arg Tyr Phe Pro Val Gln Asp Thr
            100                 105                 110

Arg Ala Leu Ile Glu Val Leu Arg Glu Val Gly Asp Met Pro Ile Thr
        115                 120                 125

Met Gly Gly Phe Gly Phe Thr Ser His Ala His Leu Leu Leu Asp Tyr
    130                 135                 140

Leu Gly Ala Asp Phe Gly Val Gln Gly Asp Pro Asp Gly Phe Phe Ala
145                 150                 155                 160

Arg Phe Glu Asp Val Val Ala Arg Arg Asp Leu Glu Ser Val Pro Gly
                165                 170                 175

Leu Ala Tyr Arg Arg Asp Gly Thr Tyr Gln Phe Asn Pro Arg Gly Phe
            180                 185                 190

Tyr Pro Pro Ala Ala Glu Arg Glu Tyr Thr Asp Glu Ile Val Asp Glu
        195                 200                 205

Leu Ile Ser Phe Tyr Gly His Ala Gln Leu Tyr Gly Ser Asn Pro Pro
    210                 215                 220

Thr Val Ala Val Glu Ala Met Arg Gly Cys Pro Phe Ser Cys Gly Phe
225                 230                 235                 240

Cys Leu Glu Pro His Val Lys Gly Arg Arg Ile Ala Tyr Arg Asp Ile
                245                 250                 255

Glu Thr Ile Val Ser Glu Leu Glu Phe Leu Leu Ser Arg Asn Leu Arg
```

-continued

```
            260                 265                 270

Arg Phe Trp Phe Val Ala Ser Glu Leu Asn Ile Gln Gly Ser Glu Phe
        275                 280                 285

Ile Leu Lys Leu Ala Glu Arg Val Ile Arg Leu Asn Glu Thr His Pro
    290                 295                 300

Gly Ser Pro Ile Glu Trp Ser Gly Phe Thr Leu Pro Arg Phe Asn Glu
305                 310                 315                 320

Ser Asp Leu Arg Leu Leu Gln Arg Ala Gly Tyr Ala Gly Ala Leu Asn
                325                 330                 335

Asp Ile Leu Ser Leu Asp Asp Glu Asn Leu His Arg Met Arg Val Pro
            340                 345                 350

Tyr Arg Ser Gly Gln Ala Ile Thr Tyr Leu Lys Ala Met Ala Lys Met
        355                 360                 365

Ala Glu Glu Glu Ser Gln Ala Gln Ala Thr Ser Pro His Gly Val Glu
    370                 375                 380

Gly Leu Arg Gln Arg Leu Ala Gly Tyr Phe Thr Leu Phe Leu Gly Asn
385                 390                 395                 400

Ser His Ala Asp Glu Arg Thr Ile Arg Arg Ser Leu Gln Gln Val Asp
                405                 410                 415

Glu His Gly Leu Arg Glu Lys Tyr Arg Gly Ala Phe Val Met Ala Ala
            420                 425                 430

Thr Arg Val Tyr Asp Ile Glu Gly Lys Tyr Ile Cys Ala Thr Ser Glu
        435                 440                 445

Glu Glu Ala Lys Ser Ile Ile Ser Tyr Asp Glu Arg Gly Glu Arg Pro
    450                 455                 460

Phe Asn Leu Leu Trp Pro Ser Phe Tyr Tyr Pro Arg Phe Leu Met Gln
465                 470                 475                 480

Arg Leu Gly Ser Thr Ala Glu Ile Leu Lys Phe Phe Ser Phe Val Gly
                485                 490                 495

Asp Thr Phe Leu Ser Leu Ala His Arg Met Arg Lys Asp Trp Asn Trp
            500                 505                 510

Phe Leu Ser Arg Asn Thr Ser Val Glu Gln Leu Arg Glu Trp Leu Ala
        515                 520                 525

Gly Ala Ser Ser Val Pro Leu Gly Ala His Glu Ala Pro Pro His Val
    530                 535                 540

Leu Glu Lys Ala Ala His Val Leu Gly Glu Pro Arg Thr Pro Ala Leu
545                 550                 555                 560

Val Ser Met Met Ala Pro Glu Pro Glu Gln Lys Pro Leu Trp Asn Glu
                565                 570                 575

Val Ala Arg Val Leu Leu Glu His Leu Phe Arg Val His Gly Lys Ser
            580                 585                 590

Val Ala Ala Val Thr Thr His Leu Gly Ile Gln Ala Asp Glu Arg Gly
        595                 600                 605

Ile Pro Arg Leu Ser Glu Tyr Arg Leu Met Glu Arg Leu Tyr Gln Arg
    610                 615                 620

Tyr Asp Ser Val Glu Gln Leu Ile Glu Glu Ala Gly Ser Cys Leu Asp
625                 630                 635                 640

Val Thr Gly Asp Ser Leu Ala Met Leu Tyr Leu Gln Trp Leu Leu Tyr
                645                 650                 655

Ala Asn Asn Val Thr Ile Arg Pro Glu Tyr Arg Glu Leu Leu Phe Glu
            660                 665                 670

Pro Pro Val Glu Pro Ala Ser Ala Val Gly
        675                 680
```

<210> SEQ ID NO 8
<211> LENGTH: 3538
<212> TYPE: PRT
<213> ORGANISM: Artificial
<220> FEATURE:
<223> OTHER INFORMATION: Seq.-ID No. 8: Arg2

<400> SEQUENCE: 8

```
Met Ser Arg Cys Glu Gln Arg Leu Arg Asp Arg Thr Lys Met Asp Thr
1               5                   10                  15

Arg Lys Gln Ala Ser Gly Glu Val Cys Phe Leu Asp Leu Phe Leu Arg
            20                  25                  30

Gln Ala Glu Leu His Pro Ser Lys Ser Ala Val Glu Cys Gly Ser Ala
        35                  40                  45

Arg Leu Thr Tyr Gln Ala Leu Val Ala Arg Ser Glu Arg Leu Ala Ser
    50                  55                  60

Ala Leu Gly Ala Ser Gly Val His Pro Gly Asp Arg Val Ala Val Val
65                  70                  75                  80

Leu His Arg Gly Leu Asp Thr Val Val Ala Met Val Ala Val Leu Arg
                85                  90                  95

Thr Gly Ala Val Tyr Val Pro Ile Asp Val Thr Trp Pro Asp Asn Arg
            100                 105                 110

Ile Arg Tyr Ile Leu Asp Asp Leu Gln Pro Gly Ala Ile Leu Cys Asp
        115                 120                 125

Glu Glu Asn Ser Arg Arg Ala Cys Phe Thr Ser Asp Asp Arg Leu Leu
    130                 135                 140

Leu Ala Ser Ser Glu Gly Thr Gly Gly Ser Asp Phe Arg Pro Gly Pro
145                 150                 155                 160

Met Ala Pro Ala Tyr Phe Met Tyr Thr Ser Gly Ser Thr Gly Arg Pro
                165                 170                 175

Lys Gly Val Val Leu Ala His Gly Gly Leu Ala Ser Arg Leu His Ala
            180                 185                 190

Phe Ser Arg Ala Tyr Glu Ile Gln Pro Glu Asp Arg Phe Leu Ala Leu
        195                 200                 205

Ser Ser Val Ser Phe Asp Val Ser Val Leu Asp Leu Met Leu Pro Leu
    210                 215                 220

Val Asn Gly Cys Cys Thr Phe Ile Ala Ser Asp Glu Gln Arg Arg Asp
225                 230                 235                 240

Pro Asp Ala Leu Arg Asn Leu Phe Glu Glu Arg Ala Leu Asn Val Ala
                245                 250                 255

Phe Ala Thr Pro Thr Thr Met Arg Ala Leu Val Ser Val Gly Trp Lys
            260                 265                 270

Gly Ser Pro Arg Thr Lys Ile Leu Cys Gly Gly Glu Ala Ile Pro Gln
        275                 280                 285

Ser Leu Met Asn Glu Leu Val Ala Arg Gly Arg Leu Phe Asn Val Tyr
    290                 295                 300

Gly Pro Thr Glu Ala Thr Val Ala Val Thr Ser Pro Glu Leu Phe Ala
305                 310                 315                 320

Gly Asp Ser Val His Leu Gly Arg Ala Leu Pro Gly Val Glu Leu Leu
                325                 330                 335

Val Leu Asp Glu Ala Gly Ala Ile Cys Gly Pro Arg Gln Pro Gly Glu
            340                 345                 350

Leu Val Ile Gly Gly Ile Gly Val Ala Leu Gly Tyr Trp Lys Asn Asp
        355                 360                 365

Glu Leu Thr Arg Lys Lys Phe Val Asp Gly Lys Tyr Arg Thr Gly Asp
```

```
    370                 375                 380

Leu Val Ser Trp Gly Glu Asp Gly Asn Leu Tyr Tyr His Gly Arg Met
385                 390                 395                 400

Asp Glu Gln Val Lys Leu His Gly His Arg Ile Glu Leu Leu Glu Ile
                405                 410                 415

Glu Glu Met Ala Arg Ser Leu Gly Leu Val Arg Asp Ile Lys Val Leu
            420                 425                 430

Ile Gln Glu Asn Ala Ala Ser Pro Arg Leu Val Ala Phe Phe Ile Gly
        435                 440                 445

Asp Glu Ala Ala Ala Gln Ser Leu Arg Arg Arg Leu Ala Ser Glu Leu
    450                 455                 460

Pro Ala Tyr Met Val Pro Ser Val Trp Val Gly Val Glu Gly Phe Pro
465                 470                 475                 480

Gln Thr Ser Thr Gly Lys Leu Asp Arg Lys Ala Leu Leu Ala Lys Val
                485                 490                 495

Asp Glu Arg Ala Glu Gly Leu Asp Ser Pro Pro Glu Ala Ala Pro Ser
            500                 505                 510

Gly Gly Arg Glu Ala Thr Leu Leu Gly Ile Trp Arg Glu Val Leu Gln
        515                 520                 525

Arg Pro Asp Leu Ser Pro Asp Asp Asp Phe Phe Ala Ser Gly Gly Asp
    530                 535                 540

Ser Ile Leu Ala Met Arg Thr Leu Ser Arg Ala Arg Glu Ala Gly Ile
545                 550                 555                 560

Asn Tyr Arg Ala Val His Ile Phe Gln His Pro Thr Val Arg Ser Leu
                565                 570                 575

Leu Glu Thr Val Val Gln Ala His Glu Gly Pro Arg Pro Glu Leu Pro
            580                 585                 590

Glu Leu Thr Thr Ser Gly Leu Thr Pro Val Gln Arg Trp Phe Phe Glu
        595                 600                 605

Gln Pro Leu Val Asn Arg Gly Phe Trp Asn Gln Ser Ile Leu Leu Arg
    610                 615                 620

Leu Thr Arg Pro Met Glu Leu Arg Glu Leu Arg Glu Ile Ala Asp Cys
625                 630                 635                 640

Leu Thr Arg Thr His Gln Ile Leu Ala Cys Glu Ile Asp Glu Lys Gly
                645                 650                 655

Met Arg Leu Gly Ser Arg Asp Ala Asp Ala Cys Cys Ala Gln Val Ser
            660                 665                 670

Leu Thr Thr Gly Ser Gly Thr Ser Ser Pro Glu Phe Ala Arg Ile Ile
        675                 680                 685

Asp Asp Ala His Arg Ser Leu Arg Pro Glu Glu Gly Arg Leu His Arg
    690                 695                 700

Leu Val Leu Ile Glu Ser Arg Gly Ser Gly Glu Trp Tyr Leu Phe Trp
705                 710                 715                 720

Thr Ile His His Leu Val Ile Asp Gly Val Ser Trp Arg Ile Leu Leu
                725                 730                 735

Ser Asp Leu Gly Thr Leu Leu Gln Gln Lys Ala Ser Gly Asp Ala Leu
            740                 745                 750

His Leu Glu Lys Ala Pro Val Ser Phe Leu His Cys Ser Glu Arg Met
        755                 760                 765

Arg Ala Leu His Gly Lys Val Arg Glu Ala Glu Leu Ser Tyr Trp Arg
    770                 775                 780

Lys Leu Pro Glu Ala Pro Leu Pro Trp Ser Ser Glu Val Arg Gln Glu
785                 790                 795                 800
```

```
Val Pro Glu Ala Ala Arg Thr Glu Leu Val Leu Ser Leu Ser Gln Glu
                805                 810                 815

Ala Thr Arg Gly Leu Leu Gln Asp Val Leu Ala Gly Thr Gly Lys Gly
            820                 825                 830

Ile Asn Asp Val Leu Leu Ser Ala Leu Leu Gln Ala Val Tyr Asp Val
        835                 840                 845

Ser Gly Glu Arg Arg Leu Ser Leu Trp Leu Glu Gly His Gly Arg Glu
    850                 855                 860

Glu Gly Leu Leu Glu Leu Asp Thr Ser Arg Thr Val Gly Trp Phe Thr
865                 870                 875                 880

Ser Met Phe Pro Val Tyr Leu Glu Ser Pro Ser Pro Glu Asp Phe Gln
                885                 890                 895

Ser Thr Leu Glu Ala Thr Arg Ala Ser Leu Gly Ala Met Pro Asn Arg
            900                 905                 910

Gly Val Gly Tyr Gly Ile Val Arg Tyr Leu Gly Glu Asp Ala Arg Gly
        915                 920                 925

Glu Gly Leu Arg Thr Gly Asn Glu Pro Arg Ile Ser Phe Asn Tyr Leu
    930                 935                 940

Gly Gln Trp Asp Asp Val Ala Ser Asp His Phe Ser Val Val Ser Glu
945                 950                 955                 960

Pro Gly Leu Asp Asp Ile Ala Pro Glu Asn Lys Trp His Arg Glu Val
                965                 970                 975

Asp Ile Asn Cys Leu Val Ala Gln Gly Ile Phe Lys Val His Leu Thr
            980                 985                 990

Phe Val Arg Arg Leu Gln Asp Lys  Glu Lys Leu Glu Ser  Leu Leu Arg
        995                 1000                1005

Arg Phe  Ile Ala Arg Leu Glu  Ser Ala Ile Asp Ala  Tyr Lys Gly
    1010                1015                1020

Ala Gly  Glu Phe Arg Arg Lys  Phe Pro Leu Leu Ser  Ile Pro Pro
    1025                1030                1035

Glu Ala  Phe Ala Arg Asn Gly  Ile Asp Leu Gln Ser  Val Gln Asp
    1040                1045                1050

Ala Tyr  Pro Leu Thr Pro Met  Gln Glu Gly Met Leu  Leu Arg Ala
    1055                1060                1065

Leu Thr  Val Pro Glu Ser Gly  Asn Tyr Ile Val Arg  Thr Phe Phe
    1070                1075                1080

Asp Leu  Thr Gly Glu Leu His  Pro Asp Ala Trp Arg  Glu Ala Trp
    1085                1090                1095

Arg Arg  Glu Leu Ala Glu Gln  Glu Leu Leu Arg Ser  Ala Phe Phe
    1100                1105                1110

Trp Glu  His Ser Pro Thr Pro  Phe Gln Val Val Phe  Ser His Val
    1115                1120                1125

Asp Leu  Asp Trp Arg Thr His  Asp Trp Gly His Leu  Gly Pro Glu
    1130                1135                1140

Glu Gln  Gln Gln Ala Phe Ser  Lys Leu Glu Lys Ala  Arg His Ala
    1145                1150                1155

Glu Gly  Phe Ser Leu Ser Lys  Ala Pro Leu Leu Arg  Ile Asp Phe
    1160                1165                1170

Ile Ala  Arg Gly Gly Ser Asp  Tyr Arg Leu Leu Leu  Ser Phe His
    1175                1180                1185

His Leu  Ile Leu Asp Gly Trp  Ser Leu Gln Val Leu  Leu Glu Arg
    1190                1195                1200

Val Leu  Lys Arg Tyr Gly Gln  Ala Arg Gly Gly Gly  Glu Glu Arg
    1205                1210                1215
```

```
Leu Thr  Pro Ala Phe Arg Phe  Arg Asp Tyr Val Ala  Trp Asn Arg
    1220                 1225                 1230

Asn His  Glu Ser Ser Asp Ala  Leu Arg Phe Trp Arg  Glu His Leu
    1235                 1240                 1245

Glu Gly  Val Glu Glu Pro Thr  Leu Leu Gly Asp Glu  Gln Gly Thr
    1250                 1255                 1260

Arg His  Glu Tyr Ala Glu Thr  Val Leu Arg Leu Glu  Glu Ala Arg
    1265                 1270                 1275

Trp Ser  Gly Leu Gly Ala Arg  Cys Arg Arg Gln Gly  Met Thr Lys
    1280                 1285                 1290

Ser Ser  Leu Ile Gln Ala Val  Trp Cys Trp Val Ala  Lys Ser Tyr
    1295                 1300                 1305

Gly Arg  Lys Ser His Val Val  Tyr Gly Leu Thr Gln  Ala Gly Arg
    1310                 1315                 1320

Ala Ala  Ala Ile Gly Asp Ile  Glu Asn Gly Val Gly  Leu Phe Ile
    1325                 1330                 1335

Thr Thr  Ser Pro Val Ala Val  Asp Leu Asp Lys His  Ser Lys Leu
    1340                 1345                 1350

Ser Thr  Val Gly Arg Phe Ile  Gln Gln Val Asn Ala  Gln Ala Leu
    1355                 1360                 1365

His His  Asp Arg Leu Pro Leu  Ser Glu Ile Gln Arg  Ile Ser Gly
    1370                 1375                 1380

Arg Glu  Ile Gly Gln Pro Leu  Phe Asp Cys Leu Leu  Val Phe Glu
    1385                 1390                 1395

Gln Glu  Pro Ile Pro Glu Leu  Ala Gly Gly Val Ser  Gly Gly Leu
    1400                 1405                 1410

Ser Val  Ala Gly Thr Arg Thr  Tyr Glu Ser Thr Glu  Tyr Pro Leu
    1415                 1420                 1425

Thr Leu  Ser Ile Leu Glu Lys  Arg Asp Gly Ser Cys  Asp Leu Arg
    1430                 1435                 1440

Phe Tyr  Phe Asn Lys Lys Asn  Phe Ser Glu Phe Arg  Val Glu Gly
    1445                 1450                 1455

Leu Arg  Leu Leu Phe Glu Glu  Ile Leu Ala Ala Trp  Glu Arg Glu
    1460                 1465                 1470

Gln Glu  Leu Glu Leu Ser Ser  Leu Pro Ala Phe Pro  Ser Arg Asp
    1475                 1480                 1485

Gly Ala  Leu Leu Ser Arg Trp  Asn Ala Thr Gly Ser  Asp Tyr Pro
    1490                 1495                 1500

Ala Gln  Ser Leu Thr Glu Leu  Phe Leu Gln Gln Ala  Arg Arg Thr
    1505                 1510                 1515

Pro Asn  His Arg Ala Val Arg  Tyr Gly Glu Arg Glu  Leu Ser Tyr
    1520                 1525                 1530

Ala Glu  Leu Ala Glu Arg Thr  Gly Thr Leu Ala Arg  Arg Leu Glu
    1535                 1540                 1545

Ala Leu  Gly Val Arg Pro Gly  Thr Pro Val Ala Val  His Met His
    1550                 1555                 1560

Arg Ser  Leu Glu Met Val Ile  Ala Leu His Ala Ile  Val Arg Ala
    1565                 1570                 1575

Gly Gly  Ala Tyr Val Pro Ile  Asp Pro Glu Tyr Pro  Ala Ala Arg
    1580                 1585                 1590

Val Arg  Thr Ile Leu Glu Asp  Val Ala Ala Pro Val  Val Ile Phe
    1595                 1600                 1605

His Asp  Ala Ala Pro Leu Lys  Cys Gln Val Gly Gly  Thr Val Leu
```

```
    1610                1615                1620

Asp Val  Thr Arg Ile Val Glu  Glu Gly His Gly Gly  Ala Asp His
    1625                1630                1635

Arg Ala  Ala Glu Tyr Asp Pro  Glu Arg Leu Met Tyr  Ile Ile Tyr
    1640                1645                1650

Thr Ser  Gly Ser Thr Gly Arg  Pro Lys Gly Val Lys  Cys Arg His
    1655                1660                1665

Glu Gly  Ala Val Asn Arg Ile  Cys Trp Met Gln Arg  Ser Tyr Pro
    1670                1675                1680

Leu Ser  Ser Asp Asp Val Val  Leu Gln Lys Thr Pro  Tyr Thr Phe
    1685                1690                1695

Asp Val  Ser Val Trp Glu Phe  Phe Trp Pro Leu Ala  Val Gly Ala
    1700                1705                1710

Ser Leu  Val Val Ala Ala Pro  Gly Val His Gln Asp  Ala Ser Ala
    1715                1720                1725

Leu Ala  Ala Leu Ile Glu Arg  Glu Gly Val Thr His  Leu His Phe
    1730                1735                1740

Val Pro  Ser Met Leu Asp Val  Phe Leu Ala Ser Lys  Gly Gly Ala
    1745                1750                1755

Arg Cys  Ala Ser Leu Arg Arg  Val Phe Cys Ser Gly  Glu Ala Leu
    1760                1765                1770

Pro Ser  Pro Val Val Lys Glu  Phe Phe Arg Ser Val  Pro His Ala
    1775                1780                1785

Glu Leu  His Asn Leu Tyr Gly  Pro Thr Glu Ala Ser  Ile Asp Val
    1790                1795                1800

Thr Ala  Trp Asp Cys Arg Ser  Asp Ser Pro Val Ala  Ser Ile Pro
    1805                1810                1815

Ile Gly  Tyr Ala Ile Gln Asn  Val Arg Leu His Val  Leu Asp Glu
    1820                1825                1830

Lys Gln  Ala Pro Val Pro His  Gly Val Pro Gly Glu  Leu Cys Ile
    1835                1840                1845

Ala Gly  Ile Ala Leu Ala Glu  Gly Tyr Val Asn Arg  Pro Glu Glu
    1850                1855                1860

Thr Ala  Lys Arg Phe Val Gln  Ser Ser Trp Asp Ala  Arg Glu Arg
    1865                1870                1875

Leu Tyr  Arg Thr Gly Asp Leu  Ala Arg Tyr Leu Pro  Asn Gly Ala
    1880                1885                1890

Ile Glu  Tyr Leu Gly Arg Leu  Asp Gln Gln Val Lys  Leu Arg Gly
    1895                1900                1905

Leu Arg  Ile Glu Leu Asp Glu  Val Ser Ser Val Leu  Leu Arg Asp
    1910                1915                1920

Ala Arg  Val Arg Gln Ala Val  Val Arg Val Val Ala  Gly Pro Ala
    1925                1930                1935

Gly Gln  Pro Val Leu Ala Ala  Tyr Val Val Ala His  Glu Gly Ser
    1940                1945                1950

Ala Gly  Thr Leu Glu Glu Ala  Leu Lys Ala Glu Leu  Glu Arg Ser
    1955                1960                1965

Leu Pro  Arg Tyr Met Val Pro  Glu Phe Phe Phe Phe  Leu Glu Ala
    1970                1975                1980

Leu Pro  Val Asn Arg Asn Gly  Lys Leu Asp Ala Asp  Ala Leu Pro
    1985                1990                1995

Arg Pro  Gly Ala Ser Ser Ser  Arg Glu Trp Glu Pro  Pro Gln Thr
    2000                2005                2010
```

```
Glu Val  Glu Lys Asp Leu Ala  Ala Ile Trp Gln Arg  Val Leu Gly
    2015                 2020                 2025

Val Glu  Arg Val Gly Arg Asn  Asp Ser Phe Phe Ala  Leu Gly Gly
    2030                 2035                 2040

Asp Ser  Ile Leu Ser Ile Arg  Ile Leu Ala Leu Ala  Lys Glu Arg
    2045                 2050                 2055

Gly Trp  Asp Val Ser Leu Gly  Glu Leu Phe Arg Ser  Pro Arg Leu
    2060                 2065                 2070

Ser Asp  Phe Ala Arg Thr Ala  Lys Ala Ala Ala His  Thr Pro Val
    2075                 2080                 2085

Leu Ala  Arg Ser Ala Phe Ser  Leu Ile Ser Ala Arg  Asp Arg Ala
    2090                 2095                 2100

Ala Met  Pro Ala Ser Val Val  Asp Ala Leu Pro Ile  Ala Ala Leu
    2105                 2110                 2115

Gln Ala  Gly Met Leu Phe His  Thr Lys Leu Ala Glu  Glu Gly Val
    2120                 2125                 2130

Met Tyr  Arg Asp Ser Phe Leu  Tyr Val Ile Gly Gly  Glu Phe Asn
    2135                 2140                 2145

Glu Gln  Ala Phe Arg Gln Ala  Leu Lys Glu Leu Val  His Arg His
    2150                 2155                 2160

Pro Met  Leu Arg Thr Ser Phe  Glu Leu Gly Ala Tyr  Ser Glu Pro
    2165                 2170                 2175

Leu Gln  Arg Val Glu Arg Glu  Val Glu Leu Pro Leu  Arg Leu Glu
    2180                 2185                 2190

Asp Trp  Arg Asp Ser Gln Asp  Gln Glu Gln Arg Leu  Ser Ala Trp
    2195                 2200                 2205

His Glu  Ser Tyr Arg Pro Thr  Phe Asp Ile Thr Arg  Ala Pro Leu
    2210                 2215                 2220

Phe Lys  Met Glu Val Lys Leu  Leu Ser Gly Ala Arg  Phe Ala Leu
    2225                 2230                 2235

Gly Leu  Cys Phe His His Ala  Ile Leu Asp Gly Trp  Ser Ile Ala
    2240                 2245                 2250

Ser Met  Met Thr Glu Leu Leu  Leu Asp Tyr Gln Arg  Leu Leu Thr
    2255                 2260                 2265

Gly Arg  Gly Arg Ala Ile Glu  Pro Leu Gly Ser Gly  Tyr Ala Asp
    2270                 2275                 2280

Tyr Leu  Glu Leu Glu Lys Arg  Val Val Glu Asp Pro  Gln Gln Lys
    2285                 2290                 2295

Ala Phe  Trp Ser Thr Tyr Leu  Asn Asp Ala Gln Ser  Leu Arg Leu
    2300                 2305                 2310

Pro Val  Lys Gln Glu Val Glu  His Arg Asn Arg Arg  Gly Thr Ser
    2315                 2320                 2325

Val His  Gly Arg Phe Asp Ile  Pro Glu Glu Leu Val  Gly Gln Leu
    2330                 2335                 2340

Glu Arg  Ile Ala Arg Ser Leu  Glu Ile Thr Lys Arg  His Leu Phe
    2345                 2350                 2355

Leu Ala  Ala His Phe Arg Val  Leu Ala Met Ile Cys  Gly His Lys
    2360                 2365                 2370

Asp Ile  Val Ser Gly Val Val  Thr Asn Gly Arg Pro  Glu Thr Val
    2375                 2380                 2385

Asp Ala  Glu Arg Ile Val Gly  Leu Phe Leu Asn Ala  Pro Pro Met
    2390                 2395                 2400

Arg Leu  Thr Leu Gly Gly Gly  Ser Trp Arg Gln Leu  Ile Gln Ala
    2405                 2410                 2415
```

```
Ile Val  Glu Glu Glu Arg Asn  Ile Leu Pro His Arg  Arg Tyr Pro
    2420                 2425                 2430

Val Ser  Glu Met Lys Arg His  Cys Val Gln Ala Asp  Leu Phe Asp
    2435                 2440                 2445

Val Ala  Phe Asn Tyr Val Asp  Phe His Val Tyr Ser  Arg Ala Gly
    2450                 2455                 2460

Glu Leu  Ala Ser Val Gly Ile  Gln Thr Leu Lys Ala  Lys Glu Val
    2465                 2470                 2475

Thr Asn  Phe Gly Leu Tyr Val  Thr Phe Tyr Gln Gly  Trp Pro Tyr
    2480                 2485                 2490

Ser Asn  Gln Phe Thr Leu Ala  Tyr Asp Pro Asp Leu  Phe Asp Arg
    2495                 2500                 2505

Glu Gln  Val Asp Gln Phe Ala  Arg Tyr Tyr Leu Ala  Ala Leu Arg
    2510                 2515                 2520

Ala Met  Ala Gln Ser Leu Glu  Gly Arg Tyr Glu Leu  Ser Leu Leu
    2525                 2530                 2535

Thr Pro  Glu Glu Arg Ser Ala  Leu Leu Ile Ser Gly  Glu Pro Pro
    2540                 2545                 2550

Ala Ser  Lys Pro Ala Leu Val  Glu Lys Ile Trp Ser  Asn Ala Arg
    2555                 2560                 2565

Ala His  Pro Glu Arg Gln Ala  Leu Thr Asp Gly Ser  Arg Ser Leu
    2570                 2575                 2580

Ser Tyr  Arg Glu Leu Ala Ser  Leu Ser Asp Ser Leu  Ala Arg Ala
    2585                 2590                 2595

Leu His  Gln Ala Glu Val Lys  Pro Gly Asp Ile Val  Ala Val Asn
    2600                 2605                 2610

Leu Arg  Arg Asp Val His Leu  Pro Val Ala Leu Leu  Gly Val Met
    2615                 2620                 2625

Arg Ala  Gly Ala Thr Tyr Leu  Pro Leu Asp Asn Arg  Phe Pro Leu
    2630                 2635                 2640

Glu Arg  Gln Ala Phe Met Leu  Gln Asp Ser Gly Ala  Lys Leu Val
    2645                 2650                 2655

Leu Cys  Asp Asn Glu Thr Arg  Pro Ala Ser Gly Gly  Thr Ala Arg
    2660                 2665                 2670

Leu Phe  Asn Leu Asp Glu Glu  Lys Trp Gln Asp His  Gly Gly Glu
    2675                 2680                 2685

Arg Pro  Leu Pro Glu Leu His  Ala Glu Ser Ile Ala  Tyr Leu Ile
    2690                 2695                 2700

Tyr Thr  Ser Gly Ser Thr Gly  Lys Pro Lys Gly Val  Leu Ile Arg
    2705                 2710                 2715

His Arg  Asn Leu Asp Asn Phe  Ile Ala Ser Met Glu  Arg Ser Pro
    2720                 2725                 2730

Gly Phe  Ser Gln Gly Asp Arg  Leu Leu Ala Val Thr  Thr Val Ala
    2735                 2740                 2745

Phe Asp  Ile Ala Ala Leu Glu  Leu Phe Leu Pro Leu  Ser Cys Gly
    2750                 2755                 2760

Gly Gln  Val Val Leu Ala Pro  Glu Gln Val Gly Lys  Asp Ala Thr
    2765                 2770                 2775

Leu Leu  Met Glu Trp Leu Lys  Arg His Asp Ile Thr  Val Met Gln
    2780                 2785                 2790

Ala Thr  Pro Ala Thr Trp Gln  Gln Phe Val Asp Leu  Gly Trp Arg
    2795                 2800                 2805

Gly Lys  Pro Asp Leu Lys Ile  Leu Val Gly Gly Glu  Ala Leu Pro
```

```
    2810                2815                2820

Pro Ala  Leu Ala Arg Gly Leu  Leu Thr Arg Cys Arg  Glu Leu Trp
    2825                2830                2835

Asn Met  Tyr Gly Pro Thr Glu  Thr Thr Val Trp Ser  Ser Cys Met
    2840                2845                2850

Arg Ile  Ala Asp Ser Thr Arg  Ile Arg Ile Gly Gln  Pro Ile Ala
    2855                2860                2865

Asp Thr  Arg Leu Tyr Val Leu  Asp Ala Tyr Gly Asn  Pro Ala Pro
    2870                2875                2880

Arg Gln  Thr Val Gly Glu Leu  Tyr Ile Ala Gly Gly  Gly Val Ala
    2885                2890                2895

Ala Gly  Tyr Trp Arg Arg Pro  Asp Leu Thr Arg Glu  Arg Phe Gln
    2900                2905                2910

Asp Asp  Pro Phe Phe Gly Gly  Pro Met Tyr Arg Thr  Gly Asp Leu
    2915                2920                2925

Ala Arg  Ile Asp Ser Arg Asn  Glu Val Glu Cys Leu  Gly Arg Thr
    2930                2935                2940

Asp His  Gln Val Lys Leu Arg  Gly Tyr Arg Ile Glu  Leu Gly Glu
    2945                2950                2955

Ile Asp  Ala Ala Ile Gln Glu  His Pro Asp Val Ser  Gln Ser Ala
    2960                2965                2970

Val Ile  Leu Arg Arg His Ser  Glu Arg Gly Asp Glu  Leu Ala Gly
    2975                2980                2985

Tyr Tyr  Thr Leu His Asp Glu  Ala Leu Ser Arg Arg  Ala Asn Glu
    2990                2995                3000

Leu Tyr  Gly Glu Gln Val Val  Arg Trp Glu Ala Val  Trp Ser Glu
    3005                3010                3015

Thr Tyr  Gly Arg Ser Lys Glu  Asn Arg Gly Ala Leu  Asn Leu Ala
    3020                3025                3030

Gly Trp  Asn Ser Ser Tyr Thr  Gly Gln Pro Met Pro  Glu Ala Glu
    3035                3040                3045

Met Arg  Glu Trp Ile Asp Glu  Thr Val Ala Arg Ile  Arg Ser Leu
    3050                3055                3060

Gly Ala  Lys Arg Ile Leu Glu  Ile Gly Cys Gly Thr  Gly Leu Leu
    3065                3070                3075

Leu Ala  Arg Leu Ala Pro His  Cys Glu Arg Tyr Thr  Ala Thr Asp
    3080                3085                3090

Phe Ser  Pro Ala Ala Leu Glu  Tyr Val Gln Ser Ala  Ile Val Pro
    3095                3100                3105

Gln Leu  Ser His Leu Asp Cys  Glu Val Gln Leu Val  Arg Ala Thr
    3110                3115                3120

Ala Asp  Arg Leu Glu Gly Val  Glu Asp Gly Gln Phe  Asp Leu Val
    3125                3130                3135

Ile Leu  Asn Ser Val Val Gln  Tyr Phe Pro Ser Arg  Glu Tyr Leu
    3140                3145                3150

Asp Lys  Val Leu Ala Ala Ala  Ile Arg Lys Thr Arg  Gln Pro Gly
    3155                3160                3165

Arg Ile  Phe Val Gly Asp Val  Arg His Phe Gly Leu  Gly Arg Ala
    3170                3175                3180

Phe His  Ala Ser Ile Ala Asp  Tyr Gln Ser Lys Gly  Ala Leu Ala
    3185                3190                3195

Pro Ala  Ala Leu Glu Glu Lys  Val Ala Gln Gly Leu  Arg Lys Glu
    3200                3205                3210
```

```
Thr Glu  Leu Leu Leu Ser Pro  Arg Tyr Phe Leu Ser  Leu Ser Ser
    3215                 3220                 3225

Leu Gly  Val Ala His Ala Glu  Ile Glu Leu Arg Arg  Gly Thr His
    3230                 3235                 3240

His Asn  Glu Leu Thr Arg Phe  Arg Tyr Asp Ala Val  Leu Ser Ile
    3245                 3250                 3255

Gly Gln  Arg Pro Glu Gln Leu  Glu Thr Arg Trp Tyr  Glu Trp Glu
    3260                 3265                 3270

Thr His  Pro Leu Ser Gly Asp  Glu Leu Ser Thr Lys  Leu Lys Gln
    3275                 3280                 3285

Ala Gly  Glu Cys Phe Gly Leu  Arg Ala Val Gly Asn  Ala Arg Leu
    3290                 3295                 3300

Ala Arg  Glu Arg Glu Leu Leu  Gly Ala Arg Ser Asp  Glu Thr Gln
    3305                 3310                 3315

Gly Ser  Ala Gly Ala Gly Ala  Gly Leu Asp Pro Glu  Gln Leu Tyr
    3320                 3325                 3330

Arg Leu  Ala Glu Ala His Gly  Tyr Arg Ala Lys Thr  Ser Trp Ala
    3335                 3340                 3345

Ser Glu  His Ala Tyr Gly Ala  Phe Asp Val Ala Phe  Ile Pro Ala
    3350                 3355                 3360

Gly Lys  Asn Ala Thr Pro Leu  Phe Glu Leu Ala Gln  Gly Ser Ala
    3365                 3370                 3375

Arg Leu  Ser Asn Ala Pro Leu  Leu Ser Gln Ile Asp  Val Arg Val
    3380                 3385                 3390

Gly Ala  Glu Ile Arg Arg Ala  Leu Gln Lys Asn Leu  Pro Glu Tyr
    3395                 3400                 3405

Met Val  Pro Ala Arg Leu Val  Leu Leu Asp Ser Met  Pro His Thr
    3410                 3415                 3420

Pro Asn  Gly Lys Val Asp Arg  Ser Arg Leu Pro Asp  Val Gly Arg
    3425                 3430                 3435

Asn Ala  Val Ser Ser Glu Phe  Val Glu Pro Arg Asn  Glu Asn Glu
    3440                 3445                 3450

Arg Lys  Leu Cys Gln Met Trp  Gln Glu Leu Leu Gly  Leu Glu Arg
    3455                 3460                 3465

Val Gly  Val Arg Asp Asp Phe  Phe Ala Leu Gly Gly  His Ser Leu
    3470                 3475                 3480

Leu Ala  Thr Gln Leu Ile Thr  Arg Ile Asn Lys Gln  Phe Glu Cys
    3485                 3490                 3495

Asn Leu  Ser Leu Arg Ala Leu  Phe Asp Phe Pro Thr  Ile Glu Gln
    3500                 3505                 3510

Leu Val  Arg Glu Ile Glu Arg  Ser Arg Thr Leu Gln  Gly Pro Ala
    3515                 3520                 3525

Met Pro  Lys Ile Gln Arg Arg  Lys Lys Asn
    3530                 3535
```

<210> SEQ ID NO 9
<211> LENGTH: 5946
<212> TYPE: PRT
<213> ORGANISM: Artificial
<220> FEATURE:
<223> OTHER INFORMATION: Seq.-ID No. 9: Arg3

<400> SEQUENCE: 9

```
Met His Leu Pro Glu Leu Leu Pro Leu Ser Phe Ala Gln Thr Arg Leu
1               5                   10                  15

Trp Phe Leu Glu Gln Leu Phe Pro Gly Arg Ala Thr Tyr His Ile Pro
```

-continued

```
            20                  25                  30

Gln Phe Trp Arg Leu Arg Gly Gly Val Asn Val Ser Ala Leu Val Lys
        35                  40                  45

Ala Leu Lys Asn Thr Ala Ala Arg His Glu Ser Leu Arg Thr Thr Phe
    50                  55                  60

Val Thr Glu Asn Gly Glu Pro Arg Gln Ala Ile His Glu Asp Met Ala
65                  70                  75                  80

Leu Asp Phe Glu Cys Glu Thr Leu Asp Glu Arg Gly Gly Glu Thr Leu
                85                  90                  95

Asp Ser Tyr Leu Ser Ala Leu Thr Ala Arg Thr Phe Ser Val Ser Glu
            100                 105                 110

Gly Pro Leu Trp Arg Val Arg Leu Val Arg Thr Ser Ala Arg Glu Gln
        115                 120                 125

Val Leu Ala Val Val Phe His His Ile Ile Cys Asp Gly Trp Ser Met
    130                 135                 140

Gly Ile Phe Ser Arg Glu Val Ser His His Tyr Asn Gln Ala Ile Gly
145                 150                 155                 160

Glu Ser Leu Gly Glu Leu Ser Glu Pro Pro Ile Gln Phe Gly Asp Phe
                165                 170                 175

Ala Gln Trp Gln Arg Glu Trp Leu Gln Gly Glu Arg Leu Glu Leu Gln
            180                 185                 190

Leu Ser Tyr Trp Ala Glu Lys Leu Lys Gly Ala Pro Asp Leu Leu Ala
        195                 200                 205

Leu Pro Thr Asp Phe Ser Arg Pro Pro Ala Ala Ser Asn Lys Gly Lys
    210                 215                 220

Leu Tyr Gly Thr Phe Val Pro Pro Glu Val Val Gln Arg Leu Lys Asp
225                 230                 235                 240

Leu Ala Arg Gln Glu Lys Ala Thr Leu Phe Met Val Leu Met Ala Ala
                245                 250                 255

Phe Lys Val Leu Leu Arg Arg Tyr Ser Gly Ser Asp Asp Ile Val Val
            260                 265                 270

Gly Thr Pro Ile Ala Asn Arg His Tyr Pro Asp Val Glu Glu Val Phe
        275                 280                 285

Gly Tyr Phe Ala Asn Thr Leu Ala Leu Arg Thr Pro Leu Glu Gly Ser
    290                 295                 300

Ala Ser Phe Arg Gln Val Leu Gln Arg Val Lys His Ser Thr Leu Glu
305                 310                 315                 320

Ala Tyr Glu His Gln Asp Leu Pro Leu Glu Leu Val Val Asp Lys Leu
                325                 330                 335

Gly Val Glu Arg Asp Leu Ser Arg His Pro Val Phe Gln Val Met Phe
            340                 345                 350

Ala Leu Leu Thr Glu Gly Arg Ser Thr Leu Gly Val Gly Lys Thr Glu
        355                 360                 365

Leu Arg Leu Glu Gly Leu Glu Val Glu Ser Leu Arg Gly Val Gly Asp
    370                 375                 380

Cys Ala Lys Phe Asp Leu Ala Leu Leu Ala Glu Glu Thr Glu Gln Gly
385                 390                 395                 400

Leu Phe Leu Glu Phe Glu Tyr Ser Thr Asp Leu Phe Glu Gln Ala Thr
                405                 410                 415

Ile Glu Arg Val Ala Arg His Phe Gln Asn Leu Leu Val Glu Val Val
            420                 425                 430

Ala Gly Pro Gly Ser Ser Ile Asp Asp Tyr Phe Val Leu Ser Asp Ala
        435                 440                 445
```

```
Glu Ile Ala Glu Arg Ile Ala Cys Leu Asp Gly Tyr Gly Leu Pro His
    450                 455                 460

Asp Thr Glu Ile Cys Leu His Gln Trp Val Glu Arg Phe Ala Ala Arg
465                 470                 475                 480

Thr Pro Gln Ala Ile Ala Leu Arg Asp Gln Thr Gly Ser Met Thr Tyr
                485                 490                 495

Arg Glu Leu Asn Glu Glu Ala Asn Arg Leu Ala Arg Cys Leu Leu Glu
            500                 505                 510

Arg Gly Leu Gly His Gly Gln Ile Val Gly Leu Ala Leu Pro Arg Thr
        515                 520                 525

Arg Glu Leu Ile Val Ala Met Val Ala Ala Leu Lys Ala Arg Ala Ala
    530                 535                 540

Tyr Leu Pro Leu Asp Leu Gly Tyr Pro Ser Gln Arg Leu Arg Phe Ile
545                 550                 555                 560

Leu Glu Asp Ala Glu Thr Ala Ala Val Leu Thr Thr Arg Ala His Val
                565                 570                 575

Glu Ser Leu Arg Gly His Cys Lys His Ile Ile Ala Leu Glu Asp Val
            580                 585                 590

Ala Ala Glu Val Ala Gly Gln Ser Ala Gly Asn Leu Asp Leu Asp Tyr
        595                 600                 605

Ala Ser Gly Asp Leu Ala Tyr Leu Ile Tyr Thr Ser Gly Ser Thr Gly
    610                 615                 620

Lys Pro Lys Gly Ala Thr Ile Cys His Arg Asn Val Thr Arg Leu Phe
625                 630                 635                 640

Pro Asp Pro Glu Pro Leu Tyr Arg Phe Arg Pro Asp Asp Cys Trp Thr
                645                 650                 655

Phe Phe His Ser Cys Ala Phe Asp Leu Ser Val Trp Glu Ile Trp Gly
            660                 665                 670

Ala Leu Ser His Gly Ser Thr Leu Ser Val Val Pro Ala Glu Val Ala
        675                 680                 685

Arg Ser Thr Asp Glu Phe Arg Glu Trp Leu Val Ala His Arg Val Thr
    690                 695                 700

Val Leu Asn Gln Thr Pro Ser Ala Tyr Glu Gln Leu Leu Ser Tyr Ile
705                 710                 715                 720

Ser Arg Glu Gly Gly Ser Asp Gly Leu Arg Leu His Thr Val Met Leu
                725                 730                 735

Gly Gly Glu Gly Trp Gly Glu Ala Leu Ala Glu Arg His Arg Gln Leu
            740                 745                 750

Leu Pro His Val Ser Leu Tyr Asn Glu Tyr Gly Pro Ala Glu Cys Ala
        755                 760                 765

Val Trp Thr Thr His Gly Cys Val Tyr Asp Ala Glu Thr Val Gln Ser
    770                 775                 780

Tyr Pro Leu Asp Leu Gly Ile Ala His Ser Gln Ser Leu Ala Leu Ile
785                 790                 795                 800

Leu Asn Asp Gly His Arg Val Thr Pro Thr Gly Val Val Gly Glu Leu
                805                 810                 815

Tyr Leu Gly Gly Glu Gly Val Thr Gln Gly Tyr Trp Lys Arg Pro Glu
            820                 825                 830

Leu Asn Lys Glu Lys Phe Val His Val Ser Leu Pro Gly Lys Gly Asn
        835                 840                 845

Val Arg Leu Tyr Lys Thr Gly Asp Leu Gly Arg Tyr Lys Ser Asn Gly
    850                 855                 860

Arg Ile Glu Phe Ile Gly Arg Arg Asp His Gln Val Lys Val Arg Gly
865                 870                 875                 880
```

```
Tyr Arg Ile Glu Leu Gly Glu Ile Glu Ser Ile Leu Arg Ser Leu Pro
                885                 890                 895

Gly Val Arg Asp Ala Leu Val Met Leu Ser Glu Ser Gly Arg Gln Leu
            900                 905                 910

Val Ala Tyr Val Val Val Gly Glu Gly Gly Thr Leu Thr Gln Glu Thr
        915                 920                 925

Ile Ala Tyr Gln Leu Lys Asp Ala Leu Pro Ala Tyr Met Val Pro Ser
    930                 935                 940

Phe Phe Val Leu Leu Glu Arg Phe Pro Met Thr Asn Asn Gly Lys Val
945                 950                 955                 960

Asp Arg Ala Ala Leu Pro Lys Pro His Ala Thr Thr Gly Gln Ser Val
                965                 970                 975

Gly Ala Gln Ala Phe Val Ala Pro Ser Gly Pro Leu Glu Glu Gly Ile
            980                 985                 990

Ala Ser Val Phe Ser Glu Leu Leu  Ala Ile Thr Pro Phe  Ser Ala Glu
        995                 1000                1005

Gly Asn  Phe Phe Ser Leu Gly  Gly His Ser Leu Leu  Ala Thr Gln
    1010                 1015                1020

Ala Ala  Ala Lys Ile His Gln  Arg Leu Gly Ile Ala  Cys Pro Val
    1025                 1030                1035

Arg Thr  Leu Phe Glu Ser Ser  Thr Pro Arg Ala Leu  Ala Trp Lys
    1040                 1045                1050

Leu Gly  Gln Glu Gly Thr Lys  Gln Ala Val Ala Gly  Ala Ala Leu
    1055                 1060                1065

Pro Val  Leu Gln Pro Asn Glu  Gln Asp Arg His Gln  Pro Phe Pro
    1070                 1075                1080

Leu Thr  Asp Ile Gln Glu Ala  Tyr Trp Ile Gly Arg  Lys Gly Ala
    1085                 1090                1095

Leu Thr  Leu Gly Glu Val Ser  Val His Cys Tyr Ile  Glu Tyr Asp
    1100                 1105                1110

Met Asp  Glu Leu Asp Val Gly  Arg Leu Glu Arg Ala  Leu Asn Arg
    1115                 1120                1125

Leu Val  Gln Arg His Glu Ala  Met Arg Leu Val Val  Glu Glu Ser
    1130                 1135                1140

Gly Gln  Gln Arg Val Leu Glu  Ser Val Pro Phe Tyr  Lys Ile Glu
    1145                 1150                1155

Val Thr  Glu Leu Ser Arg Gly  Ser Arg Glu Glu Glu  Ala Arg Ala
    1160                 1165                1170

Leu Ala  Ser Val Arg Glu Arg  Met Ala His Gln Val  Leu Pro Ala
    1175                 1180                1185

Asp Arg  Trp Pro Leu Phe Glu  Ile Arg Ala Ser Arg  Ala His Gly
    1190                 1195                1200

Phe Trp  Arg Leu His Val Ser  Leu Asp Ala Leu Val  Leu Asp Ala
    1205                 1210                1215

Trp Ser  Leu Asn Leu Ile Phe  Asn Glu Trp Ala Arg  Leu Tyr Arg
    1220                 1225                1230

Asp Glu  Glu Thr Arg Leu Glu  Pro Leu Asn Val Ser  Phe Arg Asp
    1235                 1240                1245

Tyr Val  Ile Ala Glu Lys Ala  Phe Lys Ser Thr Gln  Thr Trp Gln
    1250                 1255                1260

Lys Ala  Lys Asp Tyr Trp Leu  Ala Arg Val Ala Thr  Leu Pro Asp
    1265                 1270                1275

Ala Pro  Gln Leu Pro Leu Ala  Gln Ser Gln Thr Arg  Leu Asp Ala
```

```
    1280                1285                1290

Gln His  Phe Asn Arg Glu Gln  Lys Arg Leu Thr Pro  Glu Ala Leu
    1295                1300                1305

Arg Ser  Leu Arg Lys Leu Ala  Asp Lys His Lys Val  Ser Leu Ser
    1310                1315                1320

Ser Val  Leu Gly Ala Val Phe  Ala Asp Val Leu Ser  Leu Trp Ser
    1325                1330                1335

Ser Lys  Pro His Phe Thr Leu  Asn Met Thr Leu Phe  Asn Arg Leu
    1340                1345                1350

Pro Val  His Glu Gln Ile Asn  Asp Ile Ala Gly Asp  Phe Thr Ser
    1355                1360                1365

Leu Asn  Leu Leu Glu Val Asp  Trp Arg Gly Ser Asp  Val Pro Phe
    1370                1375                1380

Ile Glu  Arg Val Arg Lys Val  Gln Glu Gln Leu Trp  Ser Asp Leu
    1385                1390                1395

Asp His  Arg Phe Phe Ser Gly  Val Gln Val Leu Arg  Glu Leu Ala
    1400                1405                1410

Arg Ala  Arg Asn Asn Pro Ala  Val Ala Met Pro Val  Val Phe Thr
    1415                1420                1425

Cys Leu  Leu Gly Ser Thr Glu  Gly Glu Gly Gln Ala  His Glu Trp
    1430                1435                1440

Glu Arg  Leu Phe Pro Asn Glu  Val Phe Asn Ile Thr  Gln Thr Pro
    1445                1450                1455

Gln Val  Trp Leu Asp Tyr Gln  Val Tyr Glu Ser Gln  Gly Glu Leu
    1460                1465                1470

Val Val  Cys Trp Asp Tyr Val  Glu Gly Leu Phe Pro  Glu Gly Leu
    1475                1480                1485

Val Gly  Ala Met His Glu Ala  Tyr Ile Thr Ser Leu  Glu Arg Leu
    1490                1495                1500

Leu Arg  Glu Glu Ser Ala Trp  Asn Glu Thr Arg Leu  Thr Asn Leu
    1505                1510                1515

Pro Glu  Ser Gln Arg Ile Arg  Arg Glu Glu Ala Asn  Ala Thr Ala
    1520                1525                1530

Trp Arg  Glu Pro Glu Leu Leu  Met His Gln Leu Phe  Glu Arg Gln
    1535                1540                1545

Val Gly  Val Ala Pro Asp Ala  Thr Ala Val Ile Asp  Ser Glu Gly
    1550                1555                1560

Ser Tyr  Thr Tyr Arg Gln Leu  Asn Val Ala Ala Asn  Arg Ile Ala
    1565                1570                1575

Arg Arg  Leu Ala Ser Leu Gly  Leu Glu Pro Asn Glu  Arg Val Ala
    1580                1585                1590

Val Leu  Ala Pro Lys Gly Trp  Arg Gln Val Val Ala  Cys Leu Gly
    1595                1600                1605

Ile Gln  Lys Ala Gly Ala Ala  Tyr Leu Pro Val Asp  Gly Ser Ala
    1610                1615                1620

Pro Ala  Glu Arg Ile Asn Lys  Val Leu Glu Leu Gly  Arg Val Arg
    1625                1630                1635

Ala Ala  Val Val Ala Ser Leu  Glu Tyr Gly Gly Ala  Phe Gly Ser
    1640                1645                1650

Asn Ala  Leu Ile Val Leu Asp  Asp Gly Leu Leu Ala  Pro Ala Ser
    1655                1660                1665

Gly Thr  Glu Asp Val Ser Asn  Pro Ala Pro Lys Gln  Thr Leu Ala
    1670                1675                1680
```

```
Asp Leu  Ala Tyr Val Ile Phe  Thr Ser Gly Ser Thr  Gly Thr Pro
    1685                 1690                 1695

Lys Gly  Val Met Ile Asp His  Arg Gly Ala Val Asn  Thr Leu Leu
    1700                 1705                 1710

Asp Ile  Asn Glu Arg Phe Gly  Val Arg Gln Asp Asp  Arg Val Leu
    1715                 1720                 1725

Ala Leu  Ser Ser Leu Thr Phe  Asp Leu Ser Val Tyr  Asp Ile Phe
    1730                 1735                 1740

Gly Leu  Leu Ala Ala Gly Gly  Ala Val Val Ile Pro  Pro Glu Ala
    1745                 1750                 1755

His Val  Lys Glu Pro Ala Glu  Trp Cys His Trp Leu  Val Gln His
    1760                 1765                 1770

Gln Val  Thr Val Trp Asn Thr  Val Pro Met Phe Met  Gln Met Leu
    1775                 1780                 1785

Met Glu  Phe Val Gly Ala Leu  Pro Val Ala Glu Arg  Glu Ala Leu
    1790                 1795                 1800

Ser Arg  Thr Leu Arg Leu Val  Met Met Ser Gly Asp  Trp Ile Pro
    1805                 1810                 1815

Val Glu  Leu Pro Asn Thr Ile  Lys Arg Val Phe Gln  Arg Glu Asp
    1820                 1825                 1830

Leu Arg  Val Met Ser Leu Gly  Gly Ala Thr Glu Ala  Ser Ile Trp
    1835                 1840                 1845

Ser Ile  Ala Tyr Glu Ile Lys  Asp Val Ala Lys Asp  Trp Thr Ser
    1850                 1855                 1860

Ile Pro  Tyr Gly Lys Pro Leu  Arg Asn Gln Thr Phe  His Val Leu
    1865                 1870                 1875

Asp Glu  Gly Met Arg Pro Arg  Pro Asp Phe Val Pro  Gly Gln Leu
    1880                 1885                 1890

Tyr Ile  Gly Gly Met Gly Val  Ala Leu Gly Tyr Phe  Gly Asp Glu
    1895                 1900                 1905

Ala Lys  Thr Ala Ala Ser Phe  Leu Arg His Pro His  Thr Gly Glu
    1910                 1915                 1920

Arg Leu  Tyr Arg Thr Gly Asp  Leu Gly Arg Tyr Leu  Ala Asp Gly
    1925                 1930                 1935

Asn Ile  Glu Phe Leu Gly Arg  Glu Asp Leu Gln Val  Lys Val Gly
    1940                 1945                 1950

Gly His  Arg Ile Glu Leu Gly  Glu Ile Asp His His  Leu His Lys
    1955                 1960                 1965

Cys Gly  Trp Ile Arg Gln Gly  Leu Thr His Val Phe  Lys Pro Asp
    1970                 1975                 1980

Gly Arg  Asn Pro Gln Leu Val  Ala Tyr Leu Val Pro  Glu Gly Val
    1985                 1990                 1995

Thr Gly  Lys Ser Glu Gln Glu  Arg Ala Glu Glu Leu  Ser Phe Lys
    2000                 2005                 2010

Leu Ala  Gly His Asn Leu Arg  Lys Thr Gly Gly Ala  Gly His Arg
    2015                 2020                 2025

Leu Val  Thr Glu Leu Glu Pro  Lys Val Tyr Phe Gln  Arg Lys Ser
    2030                 2035                 2040

Tyr Arg  Val Phe Ala Gly Glu  Glu Ser Arg Leu Ser  Gln Leu Glu
    2045                 2050                 2055

Ala Trp  Leu Arg Ser Ala Leu  Leu Pro Gly Lys Pro  Leu Ala Thr
    2060                 2065                 2070

Glu Arg  Arg Glu Trp Thr Val  Ala Glu Met Leu Ala  Pro Leu Leu
    2075                 2080                 2085
```

```
Ala Leu  Arg Glu Asp Gly Leu  Leu Leu Pro Lys Tyr  Arg Tyr Gly
    2090                 2095                 2100

Ser Ala  Gly Ser Leu Tyr Pro  Val Gln Thr Tyr Leu  Val Met Gly
    2105                 2110                 2115

Glu Gly  Arg Lys Glu Leu Ala  Pro Gly Val Tyr Tyr  Leu Asp Pro
    2120                 2125                 2130

Val Lys  His Glu Leu Val Arg  Leu Ala Asp Gly Ala  Leu Ala Cys
    2135                 2140                 2145

Ser Trp  Leu Ser Arg Arg Gly  Val Pro Leu Ala Leu  Cys Phe Val
    2150                 2155                 2160

Glu Lys  Arg Ser Ala Ile Glu  Pro Leu Tyr Gly Thr  Arg Ser Asp
    2165                 2170                 2175

Leu Tyr  Ser Ala Ile Glu Ala  Gly Ser Met Ala Ala  Leu Val Ala
    2180                 2185                 2190

Ser Ser  Thr Ala Ala Ala Gly  Ile Ser Trp Arg Thr  Arg Ser Ala
    2195                 2200                 2205

Pro Asp  Leu Glu Glu Leu Ala  Pro Val Val Leu Glu  Ser Ala Asp
    2210                 2215                 2220

Cys Ser  Ala Ile Ala Val Leu  Glu Pro Arg Glu Leu  Gln Ala Leu
    2225                 2230                 2235

Asp Glu  Arg Gly Lys Asp Ser  Asp Val Ser Val Leu  Met Tyr Val
    2240                 2245                 2250

Met Arg  Gly Ser Glu His Gly  Pro Arg Thr Gly Trp  Tyr Arg Trp
    2255                 2260                 2265

Ser Gly  Asp His Phe Glu Ala  Phe Ser Ala Pro Ala  Leu Ser Met
    2270                 2275                 2280

Val Pro  Ser Asn Pro Ala Asn  Trp Ser Ile Cys Gln  Asn Ala Ser
    2285                 2290                 2295

Phe Ala  Leu Phe Val Met Glu  Gly Lys Ala Gln Pro  Arg Thr Ser
    2300                 2305                 2310

Ser Ala  Leu Phe Thr Gly Arg  Leu Ile Gln Ser Leu  Met Glu Lys
    2315                 2320                 2325

Gly Val  Gly Leu Gly Leu Gly  Gly Cys Ser Ile Gly  Glu Met Asp
    2330                 2335                 2340

Pro Glu  Gly Gly Arg Leu Leu  Arg Glu Val His Asp  Gly Glu Phe
    2345                 2350                 2355

Val His  Ala Phe Phe Gly Gly  Pro Val Asp Ser Ala  Gln Ile Ser
    2360                 2365                 2370

Ala Val  Gly Thr Ser Glu Ala  Glu Pro Phe Glu Gln  Leu Val Lys
    2375                 2380                 2385

Arg Lys  Thr Arg Ser Val Leu  Glu Gly Ser Leu Pro  Gly Tyr Met
    2390                 2395                 2400

Val Pro  Asp His Tyr Val Leu  Leu Asp Ser Phe Pro  Leu Ser Ser
    2405                 2410                 2415

Asn Gly  Lys Val Asp Arg Ser  Arg Leu Ala Ala Pro  Glu Leu Glu
    2420                 2425                 2430

Arg Pro  Gln Lys Gln Asp Ala  Leu Val Arg Pro Trp  Asn Ser Thr
    2435                 2440                 2445

Glu Ala  Val Ile Ala Ser Ile  Trp Ala Gln Leu Leu  Gly Val Glu
    2450                 2455                 2460

Pro Asp  Ala Ala Asp Asn Phe  Phe Ala Leu Gly Gly  His Ser Leu
    2465                 2470                 2475

Thr Ala  Thr Gln Leu Cys Thr  Arg Leu Arg Glu Ala  Phe Gly Val
```

```
    2480                2485                2490

Glu Val  Pro Leu Arg Glu Val  Phe Gly Arg Ala Asp  Val Arg Ser
    2495                2500                2505

Gln Ala  Ser Met Val Glu Gly  Leu Leu Lys Gln His  Val Gly Arg
    2510                2515                2520

Gly Ala  Ser Ile Pro Arg Arg  Ala Gly Thr Gly Arg  Ser Val Ala
    2525                2530                2535

Ser Tyr  Ala Gln Lys Arg Leu  Trp Phe Val Glu Gln  Leu Ala Glu
    2540                2545                2550

Asn Gly  Ser Val Tyr Gly Met  Pro Val Ala Val Ala  Leu Gln Gly
    2555                2560                2565

Pro Met  Asp Trp Asp Ala Phe  Lys Lys Ala Leu Ala  Gly Val Val
    2570                2575                2580

Ala Arg  His Glu Ile Leu Arg  Thr Thr Phe His Met  Glu Gln Gly
    2585                2590                2595

Glu Leu  Trp Gln Val Ile His  Glu Glu Ile Thr Ala  Pro Phe Glu
    2600                2605                2610

Thr Glu  Gln Cys Pro Glu Gly  Ser Val Met Glu Lys  Arg Ala Tyr
    2615                2620                2625

Val Arg  Lys Arg Met Arg Glu  Leu Ala Arg Val Pro  Phe Asp Leu
    2630                2635                2640

Ser Thr  Gly Pro Leu Leu Arg  Phe His Ala Phe Ala  Leu Ser Arg
    2645                2650                2655

Glu Gln  His Ile Leu Phe Gly  Ala Met His His Ile  Ile Ser Asp
    2660                2665                2670

Gly Trp  Ser Val Asp Val Phe  Gln Ser Glu Leu Ser  Ala Leu Tyr
    2675                2680                2685

Asn Ala  Ala Leu Ser Gly Ser  Thr Pro Gln Phe Gln  Glu Leu Ser
    2690                2695                2700

Ile Gln  Tyr Ala Asp Phe Ala  Ala Trp Gln Arg Asp  Trp Leu Arg
    2705                2710                2715

Gly Pro  Arg Ser Glu Lys Gln  Leu Gln Phe Trp Lys  Asp Ser Leu
    2720                2725                2730

Ala Gly  Ala Pro Glu Leu Leu  Gln Leu Pro Thr Asp  Leu Pro Arg
    2735                2740                2745

Pro Glu  Arg Gln Ser Phe Arg  Gly Gly Val Val Arg  Arg Thr Leu
    2750                2755                2760

Asp Ala  Gln Leu Thr Ala Glu  Ile Asp Ser Arg Cys  Arg Glu Trp
    2765                2770                2775

Gly Val  Thr Pro Phe Met Phe  Tyr Leu Ala Ala Tyr  Lys Val Leu
    2780                2785                2790

Leu Ser  Lys Leu Ser Gly Gln  Ala Asp Ile Leu Val  Gly Thr Pro
    2795                2800                2805

Ala Ala  Asn Arg His Tyr Ser  Gln Val Glu Arg Leu  Ile Gly Tyr
    2810                2815                2820

Phe Ala  Asn Thr Leu Ala Ile  Arg Ser Arg Val Glu  Gly Gln Arg
    2825                2830                2835

Ser Phe  Ala Glu Tyr Val Gln  Ala Val Arg Glu Gly  Val Leu Ala
    2840                2845                2850

Ala Asn  Glu Asn Gln Asp Val  Pro Phe Glu Gln Val  Val Glu Ser
    2855                2860                2865

Leu Gln  Leu Arg Arg Ser Leu  Ala Tyr Gln Pro Val  Phe Gln Val
    2870                2875                2880
```

```
Met Phe Val Phe Glu Asn Glu Gly Arg Ser Ser Leu Ser Leu Asn
    2885                2890                2895

Gly Val Ser Val Gln Pro Val Ser Leu Asp Ala Gln Val Ala Arg
    2900                2905                2910

Phe Asp Leu Thr Leu Leu Ile Arg Asn Ala Gly Asp Ala Arg Glu
    2915                2920                2925

Ile Ser Phe Glu Tyr Ser Glu Asp Leu Phe Lys Arg Glu Thr Ala
    2930                2935                2940

Ala Glu Trp Leu Asp Gly Val Ile Ser Leu Val Glu Ala Ala Thr
    2945                2950                2955

Arg Asp Ser Ser Gln Pro Leu Ala Ala Leu Pro Ser Met Ser Glu
    2960                2965                2970

Ala Thr Leu Glu Lys Val Leu Gly Gln Phe Ser Arg Gly Glu Arg
    2975                2980                2985

Thr Ala Ser Pro Lys Leu Cys Leu His Glu Gln Phe Glu Arg Val
    2990                2995                3000

Val Ala Arg Gln Gly Glu Leu Cys Ala Ile Gln Thr Pro Arg Ser
    3005                3010                3015

Glu Ile Thr Tyr Glu Gln Leu Asn Asp Arg Ala Asn Arg Val Ala
    3020                3025                3030

Arg Leu Leu Ser Ser His Gly Ile Arg Lys Gly Asp Val Val Ala
    3035                3040                3045

Leu Cys Leu Lys Arg Ser Pro Asp Leu Phe Ala Cys Tyr Leu Ala
    3050                3055                3060

Val Leu Lys Leu Gly Ala Val Tyr Val Ala Ile Asp Gly Glu Tyr
    3065                3070                3075

Pro Glu Arg Arg Ile Gln His Met Leu Thr Asp Ala Gly Ala Lys
    3080                3085                3090

Leu Val Val Ala Ser Pro Val Tyr Ala Asp Lys Leu Gly Thr Ala
    3095                3100                3105

Pro Val Leu Val Thr Leu Glu Glu Cys Glu Asp Arg Leu Glu Ser
    3110                3115                3120

Met Ala Gly Ser Asn Leu Ser Val Lys Val Ser Pro Glu Asp Val
    3125                3130                3135

Ala Tyr Ile Ile Tyr Thr Ser Gly Thr Thr Gly Leu Pro Lys Gly
    3140                3145                3150

Ala Arg Val Lys His Arg Gly Val Ser Asn Leu Val Leu Ala Gln
    3155                3160                3165

Gln Glu Tyr Phe Val Ala Gly Pro Gly Lys Arg Leu Leu Gln Phe
    3170                3175                3180

Ala Ser Cys Ser Phe Asp Gly Ala Ile Trp Glu Trp Thr Thr Ala
    3185                3190                3195

Leu Leu Asn Gly Ala Thr Leu Cys Leu Val Ala Glu Ser Ser Ala
    3200                3205                3210

Glu Val Val Ser Arg Leu Thr Arg Arg Asp Glu Gln Pro Arg Ile
    3215                3220                3225

Asp Ile Ala Ala Leu Pro Pro Ser Val Val Ala Ser Leu Pro Asp
    3230                3235                3240

Asp Cys Leu Pro Gly Leu Glu Val Leu Leu Val Ala Gly Glu Ser
    3245                3250                3255

Cys Pro Arg Gly Val Val Asp Arg Trp Ser Arg Arg Thr Arg Met
    3260                3265                3270

Phe Asn Ala Tyr Gly Pro Cys Glu Ala Ser Val Thr Ser Thr Met
    3275                3280                3285
```

```
Phe Glu  Phe Asp Gly Thr Arg  Gly Ala Ser Thr Ile  Gly Arg Pro
    3290                 3295                 3300

Leu Arg  Asn Cys Asp Val Tyr  Ile Leu Asp Glu Arg  Met Leu Pro
    3305                 3310                 3315

Val Pro  Pro Gly Val Ala Gly  Glu Leu Cys Ile Ala  Gly Leu Gly
    3320                 3325                 3330

Leu Ala  Glu Gly Tyr His Asn  Arg Ala Glu Glu Thr  Glu Arg Arg
    3335                 3340                 3345

Phe Val  Glu Ala Ser Ile Gly  Ser Glu Thr Val Arg  Met Tyr Arg
    3350                 3355                 3360

Thr Gly  Asp Arg Gly Arg Trp  Ala Ser Asp Gly Asn  Ile Glu Phe
    3365                 3370                 3375

Leu Gly  Arg Leu Asp Asn Gln  Ile Lys Ile Arg Gly  Ile Arg Val
    3380                 3385                 3390

Glu Pro  Asp Glu Val Arg Thr  Gln Leu Leu Gln Val  Pro Gly Val
    3395                 3400                 3405

Ala Gln  Ala Ala Val Val Val  Asp Arg Glu Gly Gln  Glu Thr Arg
    3410                 3415                 3420

Leu Leu  Ala Tyr Val Val Ala  Ser Pro Glu Val Pro  Leu Asp Leu
    3425                 3430                 3435

Glu His  Val Arg Lys Arg Leu  Arg Ala Ala Leu Pro  Glu Ala Leu
    3440                 3445                 3450

Val Pro  Ser Trp Phe Cys Pro  Val Ala Thr Leu Pro  Met Thr Leu
    3455                 3460                 3465

Asn Gly  Lys Leu Asp Val Glu  Ala Leu Pro Arg Pro  Gly Glu Glu
    3470                 3475                 3480

Arg Thr  Glu Ala Arg Phe Glu  Glu Gly Ala Thr Glu  Val Glu Arg
    3485                 3490                 3495

Lys Leu  Gln Ala Leu Ile Ala  Gly Val Leu Glu Gly  Arg Arg Leu
    3500                 3505                 3510

Gly Arg  His Asp Asp Phe Phe  Arg Asn Gly Gly His  Ser Leu Lys
    3515                 3520                 3525

Ala Ile  His Leu Val Ala Glu  Ile Arg Lys Glu Leu  Gly Ala Glu
    3530                 3535                 3540

Leu Ala  Val Lys Thr Ile Phe  Asp Ala Pro Thr Val  Ala Glu Leu
    3545                 3550                 3555

Ala Arg  Val Ile Glu Ser Glu  Arg Arg Gln Glu Gly  Pro Thr Ala
    3560                 3565                 3570

Ser Arg  Pro Arg Leu Glu Gly  Ser Arg Phe Thr Leu  Ser Ala Leu
    3575                 3580                 3585

Gln Arg  Gln Met Trp Leu Ala  Glu Lys Val Leu Gln  Arg Ser Gly
    3590                 3595                 3600

Ala Tyr  Asn Met Pro Leu Cys  Leu Glu Leu Arg Gly  Ala Pro Asp
    3605                 3610                 3615

Ala Ser  Ala Leu Gln Asn Ala  Val Asp Met Leu Leu  Gln Arg His
    3620                 3625                 3630

Gly Val  Leu Arg Trp Gln Phe  Lys Glu Glu Ser Gly  Glu Pro Tyr
    3635                 3640                 3645

Ala Glu  Asp Cys Gly Val Asp  Thr Val Thr Leu Ala  Thr Leu Asp
    3650                 3655                 3660

Trp Arg  Glu Leu Gly Gln Gln  Glu Lys Asp Thr Ala  Leu Ala Gly
    3665                 3670                 3675

Leu Ile  Ala Thr Pro Phe Asn  Leu Ser Gln Gly Pro  Leu Trp Arg
```

```
    3680                3685                3690

Gly Ala  Leu Ile Arg Ile Gly  Glu Glu Arg Phe Trp  Leu Leu Leu
    3695                3700                3705

Cys Ala  His His Leu Leu Ala  Asp Gly Trp Ser Leu  Gly Leu Leu
    3710                3715                3720

Leu Gly  Glu Leu Ala Glu Leu  Tyr Asn Ala Arg Val  Gly His Gly
    3725                3730                3735

Thr Ala  Arg Leu Pro Ala Pro  Gly Thr Glu Tyr Ser  Arg Tyr Val
    3740                3745                3750

Glu Gln  Ser Val Gly Asp Glu  Arg Glu Leu Glu Arg  Gln Leu Glu
    3755                3760                3765

Phe Trp  Arg His Gln Leu Glu  Gly Ala Pro Gln Arg  Leu Ala Leu
    3770                3775                3780

Pro Met  Glu Leu Lys Arg Ser  Leu Ser Pro Gly Lys  Ala Gly Ala
    3785                3790                3795

Val Asp  Phe Glu Val Gly Pro  Glu Leu Thr Ala Arg  Leu Arg Glu
    3800                3805                3810

Leu Ala  Glu Gln Arg Gly Ser  Ser Leu Val Met Val  Leu Met Ser
    3815                3820                3825

Thr Tyr  Gln Ala Val Leu Ala  Arg Phe Ala Gly Ala  Asp Asp Val
    3830                3835                3840

Leu Ile  Gly Thr Pro Val Ala  Cys Arg His Lys Pro  Glu Leu Leu
    3845                3850                3855

Asn Thr  Ile Gly Leu Leu Val  Asn Thr Leu Pro Ile  Arg Leu Ser
    3860                3865                3870

Leu Thr  Pro Arg Thr Thr Phe  Ala Glu Ala Leu Ala  Gln Val Arg
    3875                3880                3885

Gln Arg  Leu Leu Glu Gly Met  Ala His Met Asp Val  Pro Phe Glu
    3890                3895                3900

Arg Ile  Val Ser Ala Val Ala  Gln Glu Arg Glu Pro  Gly Val Pro
    3905                3910                3915

Ala Leu  Cys Gln Ala Met Phe  Val Trp Glu Glu Gly  Ala Arg Gly
    3920                3925                3930

Asp Leu  Lys Leu Arg Gly Leu  Asp Val Ser Leu Lys  Ala Thr Pro
    3935                3940                3945

Val Thr  Ser Ala Lys Tyr Asp  Leu Ala Leu Leu Ala  Ser Glu Gln
    3950                3955                3960

Asp Gly  Arg Val Thr Gly Arg  Leu Glu Tyr Pro Glu  Gly Leu Tyr
    3965                3970                3975

Asp Arg  Ala Ser Val Glu Gln  Leu Ala Leu Ser Tyr  Val Lys Leu
    3980                3985                3990

Leu Ser  Glu Met Ala Lys Asp  Leu Glu Gly Ile Val  Ala Gln Ala
    3995                4000                4005

Glu Leu  Met Ser Gln Glu Gln  Arg Arg Gln Leu Glu  Ala Trp Phe
    4010                4015                4020

Glu Tyr  Arg Pro Glu Phe Leu  Glu Ala Pro Asn Leu  His Thr Leu
    4025                4030                4035

Ile Glu  Arg Gln Ala Ala Thr  Ala Pro Ala Ser Ser  Ala Leu Arg
    4040                4045                4050

Tyr Lys  Gly Glu Ser Tyr Ser  Tyr Glu Trp Leu Asn  Thr Gln Ala
    4055                4060                4065

Asn Arg  Leu Ala Arg Tyr Leu  Gly Ala Arg Gly Ile  Gly Arg Gly
    4070                4075                4080
```

```
Ser Val  Val Ala Leu Cys Leu  Ala Arg Ser Pro Glu  Leu Val Val
    4085                 4090                 4095

Ala Trp  Val Ala Val Leu Lys  Ser Gly Ala Ala Phe  Val Ser Leu
    4100                 4105                 4110

Asp Pro  His Met Pro Gln Ala  Arg Arg Arg Phe Ile  Leu Asp Asp
    4115                 4120                 4125

Ser Arg  Thr Ala Leu Val Leu  Ser His Ala Ala Phe  Ala Glu Glu
    4130                 4135                 4140

Leu Gly  Thr Gly Thr Asp Ile  Ala Val Trp Glu Glu  Val Ala Lys
    4145                 4150                 4155

Gln Leu  Thr Gly Leu Pro Ala  Glu Asn Leu Glu Leu  Glu Val Arg
    4160                 4165                 4170

Gln Glu  Glu Leu Ala Tyr Leu  Ile Tyr Thr Ser Gly  Thr Thr Gly
    4175                 4180                 4185

Asn Pro  Lys Gly Thr Met Leu  Ala His Arg Gly Met  Ile Asn Leu
    4190                 4195                 4200

Ala Val  Ser Glu Lys Gln Arg  Ser Gly Met Gly Pro  Gln Ser Lys
    4205                 4210                 4215

Val Leu  Gln Phe Thr Thr Ala  Thr Cys Asp Gly Ser  Ile Trp Glu
    4220                 4225                 4230

Trp Thr  Ser Ala Leu Val Asn  Gly Ala Glu Leu Trp  Leu Leu Asp
    4235                 4240                 4245

Ala Ser  Asn Pro Gln Glu Gln  Val Ala Gln Ala Met  Gln Leu Leu
    4250                 4255                 4260

Ser Glu  Pro Gly Ile Thr Thr  Val Ala Leu Thr Pro  Ser Val Val
    4265                 4270                 4275

Glu Leu  Leu Pro Pro Glu Ala  Met Pro Thr Val Gln  Ser Leu Thr
    4280                 4285                 4290

Leu Ala  Gly Glu Ala Cys Pro  Leu Ala Leu Leu Glu  Lys Trp Ser
    4295                 4300                 4305

Ala Arg  Ile Pro Gly Val Ala  Asn Val Tyr Gly Pro  Thr Glu Ala
    4310                 4315                 4320

Thr Val  Thr Thr Ala Thr Phe  Pro Phe Arg Pro Gly  Tyr Pro Ala
    4325                 4330                 4335

Asn Thr  Ile Gly Lys Pro Leu  Ala Asn Val Gln Val  Tyr Ile Leu
    4340                 4345                 4350

Asp Glu  His Gly Lys Leu Leu  Pro Pro Gly Val Ile  Gly Glu Leu
    4355                 4360                 4365

Cys Ile  Ala Gly Val Gly Leu  Ala Leu Gly Tyr Leu  Asp Arg Asp
    4370                 4375                 4380

Glu Leu  Thr Gln Arg Lys Phe  Val Thr His Pro Ile  Gly Pro Arg
    4385                 4390                 4395

Gly Glu  Pro Val Arg Val Tyr  Arg Ser Gly Asp Leu  Ala Arg Tyr
    4400                 4405                 4410

Leu Pro  Asp Gly His Ile Val  Phe Glu Gly Arg Arg  Asp Asn Gln
    4415                 4420                 4425

Val Lys  Val Arg Gly Tyr Arg  Val Glu Leu Asp Glu  Val Ala Trp
    4430                 4435                 4440

Val Leu  Lys Gln His Pro Gln  Val Gln Gln Ala Ser  Val Ile Val
    4445                 4450                 4455

Ser Gln  Ala Gly Lys Arg Tyr  Pro Tyr Leu Val Ala  Tyr Val Val
    4460                 4465                 4470

Pro Arg  Thr Pro Pro Ser Ser  Pro Ala Ser Leu Arg  Ala Glu Leu
    4475                 4480                 4485
```

```
Arg Ala  Tyr Met Ala Glu Arg  Leu Ser His Tyr Met  Val Pro Glu
    4490                 4495                 4500

Ala Tyr  Val Phe Ile Glu Ser  Leu Pro Leu Asn Arg  Ser Ser Met
    4505                 4510                 4515

Lys Val  Glu Val Ser Leu Leu  Pro Pro Pro Glu Gly  Asp Ser Phe
    4520                 4525                 4530

Val Arg  Asp Thr Leu Val Pro  Pro Glu Thr Ala Val  Glu Lys Glu
    4535                 4540                 4545

Leu Ala  Thr Leu Trp Met Glu  Leu Leu Gly Val Gly  Ser Thr Gly
    4550                 4555                 4560

Arg His  Asp Ser Phe Phe Arg  Leu Gly Gly Asn Ser  Leu Leu Ala
    4565                 4570                 4575

Val Lys  Leu Gly His Ala Ile  Gly Glu Arg Trp Gly  Cys Asp Ile
    4580                 4585                 4590

Ser Leu  Pro Arg Ile Phe Glu  Asn Asp Thr Leu Ala  Ala Leu Ala
    4595                 4600                 4605

Arg Cys  Ile Glu Ala Asp Glu  Arg Arg Ser His Asp  Leu Gln Leu
    4610                 4615                 4620

Ala Arg  Ala Ser Glu Arg Glu  Ser Trp Pro Leu Ser  Phe Ala Gln
    4625                 4630                 4635

Gly Arg  Met Trp Phe Leu Glu  His Leu Thr Gln Gly  Ser Ser Ala
    4640                 4645                 4650

Tyr His  Val Pro Leu Val Leu  Arg Leu Ile Gly Lys  Val Ser Phe
    4655                 4660                 4665

Glu Arg  Leu Ala Gln Ala Leu  Ser Ala Leu Val Val  Arg His Glu
    4670                 4675                 4680

Val Leu  Arg Thr Ala Tyr Val  Glu Asp Gly Asn Thr  Leu Ser Gln
    4685                 4690                 4695

Lys Ile  Leu Asp Ala Val Ala  Val Glu Met Ala Ser  Ser Asp Leu
    4700                 4705                 4710

Ser Pro  Ile Ala Pro Ser Glu  Arg Gln Ala Ala Val  Asp Arg Leu
    4715                 4720                 4725

Leu Gly  Ala Asp Leu Ala Arg  Pro Phe Ala Leu Ala  Ala Gly Glu
    4730                 4735                 4740

Asn Val  Arg Ala Arg Leu Val  Arg Phe Ser Glu Asp  Glu His Leu
    4745                 4750                 4755

Leu Cys  Leu Cys Leu His His  Ile Ala Leu Asp Gly  Trp Ser Ile
    4760                 4765                 4770

Ser Val  Leu Leu Arg Glu Leu  Gly Ser Leu Tyr Arg  Gly Gln Pro
    4775                 4780                 4785

Leu Gln  Pro Leu Pro Leu Arg  Tyr Val Asp Phe Ala  Cys Trp Gln
    4790                 4795                 4800

Arg Asp  Val Leu Glu Lys Arg  Phe Ala Glu Gln Leu  Asp Tyr Trp
    4805                 4810                 4815

Lys Ala  Glu Leu Arg Glu Leu  Pro Arg Gln Leu Glu  Leu Pro Trp
    4820                 4825                 4830

Asp His  Pro Arg Pro Pro Arg  Gln Asp Tyr Arg Gly  Ala Ser Ala
    4835                 4840                 4845

Arg Arg  Pro Leu Ser Gly Glu  Leu Arg Ala Ala Leu  Lys Gln Val
    4850                 4855                 4860

Ala Glu  Arg Tyr Asp Val Thr  Asp Phe Met Leu Tyr  Leu Thr Ser
    4865                 4870                 4875

Phe Gln  Leu Trp Leu Gly Arg  Leu Ser Asn Ser Cys  Asp Val Val
```

```
    4880                4885                4890

Val Gly  Thr Pro Val Ala Asn  Arg His Tyr Asn Gly  Val Glu Ser
    4895                4900                4905

Ile Val  Gly Leu Phe Val Asn  Thr Leu Pro Leu Arg  Leu Arg Tyr
    4910                4915                4920

Asp Gly  Ser Glu Thr Phe Gly  Gly Val Val Arg Arg  Met Lys Ser
    4925                4930                4935

Lys Val  Leu Glu Ala Tyr Ser  His Gln Asp Val Pro  Phe Glu Tyr
    4940                4945                4950

Leu Val  Asp His Leu Glu Val  Pro Arg Glu Leu Ser  His Ala Pro
    4955                4960                4965

Ile Phe  Gln Ala Met Phe Leu  Leu Gln Asp Glu Ser  Gly Arg Glu
    4970                4975                4980

Ile Asp  Leu Gly Asp Val Gln  Gly Arg Ile Ala Pro  Val Ala Gly
    4985                4990                4995

Thr Val  Ala Arg Phe Asp Val  Ser Leu Leu Val Glu  Phe Asp Glu
    5000                5005                5010

Glu Gly  Ala Glu Leu Asn Leu  Glu Tyr Ala Ser Ala  Leu Phe Arg
    5015                5020                5025

Pro Glu  Thr Ile Asp Glu Trp  Leu Glu Ser Phe Glu  Leu Phe Leu
    5030                5035                5040

Arg Ala  Ile Ala Ala Asp Ala  Glu Ala Pro Val Arg  Arg Phe Glu
    5045                5050                5055

Leu Leu  Pro Pro Arg Met Arg  Ser Phe Leu Ser Glu  Val Gly Thr
    5060                5065                5070

Gly Pro  Arg Arg Glu Tyr Gly  Ser Leu Pro Leu Pro  Glu Leu Val
    5075                5080                5085

Ala Glu  Gln Ala Lys His Gly  Gly Gln Arg Ile Ala  Val Glu Gly
    5090                5095                5100

Val Arg  Glu Ser Trp Thr Tyr  Gly Glu Leu Leu Ala  Ala Ala Glu
    5105                5110                5115

Arg Val  Ala Ala Gly Leu Gln  Arg Arg Gly Val Arg  Pro Gly Asp
    5120                5125                5130

Gly Val  Ala Ile Ala Leu Pro  Arg Asp His Arg Leu  Pro Ser Ala
    5135                5140                5145

Met Leu  Gly Val Leu Lys Ala  Gly Ala Phe Tyr Val  Pro Leu Asp
    5150                5155                5160

Leu Thr  His Pro Glu Arg Arg  Leu Gln Tyr Ile Ala  Gly Asp Ala
    5165                5170                5175

Lys Ala  Arg Phe Val Ile Thr  Gly Gly Glu Thr Arg  Phe Gly Phe
    5180                5185                5190

Asp Ile  Pro Arg Val Asn Leu  Asp Glu Leu Leu Glu  Glu Thr Ser
    5195                5200                5205

Glu Ala  Arg Pro Val Pro Ile  Ala Pro Ser Ser Leu  Ala Tyr Val
    5210                5215                5220

Ile Tyr  Thr Ser Gly Ser Thr  Gly Glu Pro Lys Gly  Val Met Val
    5225                5230                5235

Ser His  Ala Ser Leu Ser Asn  Phe Leu His Ala Met  Val Glu Glu
    5240                5245                5250

Leu Gly  Phe Gly Pro Asp Glu  Arg Leu Leu Ala Ile  Thr Thr Ile
    5255                5260                5265

Ala Phe  Asp Ile Ser Gly Leu  Glu Leu Phe Leu Pro  Leu Ile Arg
    5270                5275                5280
```

```
Gly Ala  Arg Val Val Ile Ala  Asp Glu Asp Ser Thr  Arg Asp Pro
    5285                 5290                 5295

Arg Leu  Leu Ser Arg Trp Ile  Asp Glu Arg Arg Ile  Ser Val Met
    5300                 5305                 5310

Gln Ala  Thr Pro Ala Thr Trp  Arg Met Leu Met Asp  Ala Ser Trp
    5315                 5320                 5325

Val Ala  Pro Gly Ser Phe Lys  Ala Leu Val Gly Gly  Glu Ala Leu
    5330                 5335                 5340

Pro Arg  Asn Leu Ala Asp Phe  Met Thr Ser Arg Val  Ser Gln Val
    5345                 5350                 5355

Trp Asn  Val Tyr Gly Pro Thr  Glu Ala Thr Ile Trp  Ser Thr Ile
    5360                 5365                 5370

Ala Arg  Leu Lys Ser Gly Glu  Arg Val His Ile Gly  Arg Pro Leu
    5375                 5380                 5385

Ala Asn  Thr Glu Ala Phe Val  Leu Asp Asp Gly Leu  Arg Ala Val
    5390                 5395                 5400

Pro Arg  Gly Thr Leu Gly Glu  Leu His Leu Gly Gly  Ser Gly Leu
    5405                 5410                 5415

Ala Thr  Gly Tyr Leu Gly Arg  Glu Glu Leu Thr Arg  Gln Lys Phe
    5420                 5425                 5430

Val His  His Pro Glu Leu Gly  Arg Arg Leu Tyr Lys  Thr Gly Asp
    5435                 5440                 5445

Leu Ala  Arg Val Leu Pro Ser  Gly Asp Ile Glu Phe  Val Ala Arg
    5450                 5455                 5460

Arg Asp  Ala Gln Leu Lys Ile  Arg Gly Phe Arg Ile  Glu Pro Gly
    5465                 5470                 5475

Glu Val  Glu Ala Val Leu Ser  Arg Val Pro Gly Val  Ala Arg Val
    5480                 5485                 5490

Thr Val  Leu Pro Val Gly Glu  Gly Glu Gly Thr Gln  Leu Ala Ala
    5495                 5500                 5505

Phe Leu  Leu Thr Gly Asp Glu  Arg Leu Gln Ala Gln  Ala Arg Ala
    5510                 5515                 5520

Leu Ala  Glu Gln Gln Leu Pro  Glu Tyr Met Arg Pro  Ala Arg Tyr
    5525                 5530                 5535

Val Val  Val Pro Glu Phe Pro  Leu Thr Pro Asn Gly  Lys Val Asp
    5540                 5545                 5550

Thr Lys  Ala Leu Arg Ala Leu  Val Ser Glu Gln Val  Glu Glu Ala
    5555                 5560                 5565

Ala Gly  Ser Ala Pro Lys Asn  Pro Ile Glu Phe Arg  Ile Ser Arg
    5570                 5575                 5580

Leu Trp  Ser Ala Leu Leu Gly  Val Arg His Pro Gly  Thr Arg Asp
    5585                 5590                 5595

Asn Phe  Phe Ala Leu Gly Gly  Thr Ser Leu Ala Ala  Val Arg Leu
    5600                 5605                 5610

Ala Arg  Glu Leu Glu Ser Glu  Phe Gly Ile Glu Val  Arg Val Gly
    5615                 5620                 5625

Asp Ile  Phe Arg Lys Pro Thr  Ile Ala Glu Leu Ala  Gly Leu Val
    5630                 5635                 5640

Glu Thr  Gln Gly Ser Glu Arg  Val Leu Glu Pro Leu  Val Leu Leu
    5645                 5650                 5655

Ser Arg  Glu Gln Gln Lys Pro  Pro Leu Phe Val Ile  His Pro Ala
    5660                 5665                 5670

Gly Gly  Met Ala Tyr Cys Tyr  Ala Gly Leu Ala Gln  Glu Leu Ser
    5675                 5680                 5685
```

```
Gly Phe  Thr Val His Gly Leu  Asn Gln Pro His Tyr  Tyr Glu Leu
    5690                 5695                 5700

Glu His  Arg Phe Glu Thr Leu  Ala Glu Met Ala Ala  Asp Tyr Val
    5705                 5710                 5715

Ala Arg  Ile Lys Arg Leu Gln  Pro Thr Gly Pro Tyr  Arg Leu Leu
    5720                 5725                 5730

Gly Trp  Ser Phe Gly Gly Thr  Leu Ala Tyr Glu Met  Ala Arg Gln
    5735                 5740                 5745

Leu Glu  Gln Ala Gly Glu Ala  Ile Ser Gly Val Val  Met Leu Asp
    5750                 5755                 5760

Ala His  His Val Ser Pro Leu  Gly Ala Asn Leu Pro  Thr Val Asp
    5765                 5770                 5775

Val Ser  Ala Met Leu Ala Asn  Leu Gly Leu Gly Gly  Glu Met Ala
    5780                 5785                 5790

Asp Pro  Tyr Leu Glu Lys Asp  Ile Arg Glu Ser Glu  Arg Leu Ser
    5795                 5800                 5805

Arg Asp  Tyr Lys Ala Ser Pro  Val Arg Phe Pro Val  Leu Leu Phe
    5810                 5815                 5820

Lys Pro  Thr Glu Arg Asn Gly  Phe Glu Glu Arg Leu  Tyr Ala Asp
    5825                 5830                 5835

Leu Tyr  Asn Gly Trp Arg Glu  Cys Ala Glu Asn Ser  Val Val Arg
    5840                 5845                 5850

Ser Val  Thr Gly Asp His Gly  Gly Val Leu Asp Arg  Arg Asn Val
    5855                 5860                 5865

Ser Glu  Leu Ala Arg Val Val  Glu Ala Phe Leu Ser  Gly Gly Tyr
    5870                 5875                 5880

Gly Val  Leu Leu Arg Glu Ala  Val Gln Pro Ala Leu  Ala Phe Ala
    5885                 5890                 5895

Leu Ala  Glu Arg Asp Arg Phe  Val Ala Arg Arg Leu  Val Glu Gln
    5900                 5905                 5910

Leu Pro  Arg Asp Leu Val Glu  Arg Trp Leu Lys Ser  Ala Ile Asp
    5915                 5920                 5925

Cys Leu  Pro Glu Ser Val Arg  Pro Glu Gly Ser Phe  Val Gln Ala
    5930                 5935                 5940

Leu Leu  Glu
    5945


<210> SEQ ID NO 10
<211> LENGTH: 336
<212> TYPE: PRT
<213> ORGANISM: Artificial
<220> FEATURE:
<223> OTHER INFORMATION: Seq.-ID No. 10: Arg4

<400> SEQUENCE: 10

Met Ile Pro Ser Ser Leu Glu Lys Ala Ile Tyr Gly Val Tyr Ala Thr
1               5                   10                  15

His Ala Leu His Leu Ala Asp Lys His Asn Val Phe Ala Tyr Leu Ala
            20                  25                  30

Glu Lys Gly Ala Ala Ala Pro Gly Glu Ile Ala Lys Ala Val Ala Val
        35                  40                  45

Asp Gly Glu Thr Leu Glu Arg Leu Met Leu Val Leu Gly Ala Leu Glu
    50                  55                  60

Leu Val Gln Ala Gly Ser Asp Gly Lys Tyr Arg Leu Arg Glu Gly Met
65                  70                  75                  80
```

```
Gly Pro Tyr Leu Asp Lys Lys Asp Pro Arg Tyr Val Gly Gly Phe Val
                85                  90                  95

Thr His Leu Ile Asn Ser Thr Ser Gly Arg Met Gly His Leu Asp Ala
            100                 105                 110

Tyr Leu Ser Lys Gly Lys Ala Val Val Asp Ala Ala Leu Pro Ser Pro
        115                 120                 125

Phe Asp Val Ile Tyr Lys Asp Glu Ala Ser Thr Lys Glu Phe Met Asp
    130                 135                 140

Ala Met Trp Gln Leu Ser Phe Asp Val Ser Arg Glu Leu Val Lys Leu
145                 150                 155                 160

Ala Gly Leu Asp Ser Cys Arg Gln Leu Val Asp Val Gly Gly Ala Ser
                165                 170                 175

Gly Pro Phe Ser Val Ala Ala Leu Gln His Ser Arg Glu Leu Arg Ser
            180                 185                 190

Thr Leu Phe Asp Leu Pro Lys Val Gly Arg Tyr Val Asp Glu Thr Arg
        195                 200                 205

Arg Thr Tyr Gly Leu Glu Glu Arg Leu Arg Phe Val Pro Gly Asp Phe
    210                 215                 220

Phe Arg Glu Glu Leu Pro Glu Gly Asp Cys Phe Ala Phe Gly Tyr Ile
225                 230                 235                 240

Leu Ser Asp Trp Asp Asp Ala Thr Cys Leu Glu Leu Leu Arg Lys Ala
                245                 250                 255

His Arg Ala Cys Arg Ala Gly Gly Arg Val Leu Val Met Glu Arg Leu
            260                 265                 270

Phe Asp Glu Asp Lys Arg Gly Pro Phe Ala Thr Val Phe Met Asn Leu
        275                 280                 285

Ser Met His Val Glu Thr Gln Gly Arg His Arg Thr Ala Arg Glu Tyr
    290                 295                 300

Val Gly Leu Leu Glu Ala Ala Gly Phe Arg Gly Cys Glu Val Arg Arg
305                 310                 315                 320

Ser Ser Arg Asp Lys His Leu Val Ile Gly Leu Lys His Val Thr Thr
                325                 330                 335


<210> SEQ ID NO 11
<211> LENGTH: 383
<212> TYPE: PRT
<213> ORGANISM: Artificial
<220> FEATURE:
<223> OTHER INFORMATION: Seq.-ID No. 11: Arg5

<400> SEQUENCE: 11

Met Arg Val His Leu Pro Gly Glu Cys Glu Asp Ile Val Arg Leu Gln
1               5                   10                  15

Lys Arg Ala Gly Arg Ala Ala Leu Leu Glu Ser Glu Cys Glu Ala Leu
            20                  25                  30

Ser Leu Leu Tyr Asp Arg Val Ser Val Glu Gly Pro Ser Glu Glu Glu
        35                  40                  45

Glu Ile Leu Ala Leu Leu Thr Arg Pro Phe Ser Arg Arg Leu Ala Ile
    50                  55                  60

Pro Glu Tyr Tyr Gln Tyr Thr Ser Leu His Val Tyr Gly Trp Phe Leu
65                  70                  75                  80

Ser His Tyr Arg Arg Asp Pro Leu Arg Gly Ser Leu Val Ala Leu His
                85                  90                  95

Thr Thr Leu Val Asp Leu Leu Ser Val Glu Glu Gln Gly Ala Arg Leu
            100                 105                 110

Gly Glu Ala Thr Pro Ala Tyr Ile His Glu Arg Ile Arg Gly Leu Arg
```

```
        115                 120                 125

Gly Leu Leu Gly Gln Leu Asp Glu Ile Pro Val Asp Arg Asn Gly Pro
    130                 135                 140

Leu Phe Val Ala Asp Val Leu Lys Gly Ser Lys Lys Asp Ala Gln Glu
145                 150                 155                 160

Gln Trp Arg Ala Phe Val Leu Ala Arg Cys Thr Gly Phe Pro Lys Ser
                165                 170                 175

Gln Val His Asp Glu Tyr Ile Phe Leu Arg Ser Val His Ala Cys Glu
            180                 185                 190

Ile Val Phe Phe Gln Val Arg Trp Leu Ala Leu Arg Ile Ser Glu Met
        195                 200                 205

Ile Ala Val Asp Arg Lys Glu Ala Val Phe Leu Leu Gly Gln Leu Thr
    210                 215                 220

Ser Phe Ala Glu Leu Leu Asn Lys Ile Phe Asp Val Leu Lys Thr Met
225                 230                 235                 240

Ser Pro Glu Arg Phe Met Ser Phe Arg Ala Gln Thr Gly Asn Ala Ser
                245                 250                 255

Ala Val Gln Ser Leu Asn His His Ala Met Glu Ile Ala Val Phe Gly
            260                 265                 270

Phe Asp Pro Gly Arg Ala Ser Val Phe Asp Gly Phe Glu His Leu Lys
        275                 280                 285

Arg Leu Asn Glu Pro Leu Phe Arg Glu His Ala Ser Leu Arg Ser Val
    290                 295                 300

Val Glu Ala Thr Ala Asp Gly Ala Leu Ala Glu Gly Phe Ala Lys Leu
305                 310                 315                 320

Asp Arg Cys Leu Leu Arg Trp Arg Gly Gly His Tyr Gly Phe Ala Arg
                325                 330                 335

Lys Tyr Leu Pro Val Asp Ile Lys Gly Ser Gly Gly Thr Glu Gly Ala
            340                 345                 350

Pro Tyr Leu Lys Arg Phe Ile Lys Lys Asp Asp Cys Gln Ser Gly Gly
        355                 360                 365

Gln Arg Pro Gly Thr Asp Ser Glu Leu Ala Arg Phe Phe Phe Cys
    370                 375                 380


<210> SEQ ID NO 12
<211> LENGTH: 27
<212> TYPE: DNA
<213> ORGANISM: Artificial
<220> FEATURE:
<223> OTHER INFORMATION: primer fw1

<400> SEQUENCE: 12

ctcgatatcc cagcgcaaga gctatcg                                          27


<210> SEQ ID NO 13
<211> LENGTH: 27
<212> TYPE: DNA
<213> ORGANISM: Artificial
<220> FEATURE:
<223> OTHER INFORMATION: primer bw1

<400> SEQUENCE: 13

ctcggatccg gtcgggaacc atgtacc                                          27
```

SYNTHETIC PATHWAY ENZYMES FOR THE PRODUCTION OF ARGYRINS

The invention relates to nucleic acid sequences encoding synthetic pathway enzymes, which catalyze the production of Argyrins. Accordingly, the invention also relates to the synthetic pathway enzymes, to microorganisms expressing the synthetic pathway enzymes and to a method for production of Argyrins, making use of the synthetic pathway enzymes, preferably expressed in a micro-organism. The invention provides the proteins forming part of or constituting the non-ribosomal peptide synthetases (NRPS) having the activity to catalyse at least one conversion step in the synthesis of Argyrins, including the NRPS constituting the enzymes having the activity to catalyse the synthesis of pre-Argyrin, and additional enzymes having the activity which catalyse the conversion of pre-Argyrin to at least one derivative having the core structure I of Argyrin, including e.g. natural derivatives thereof comprising Argyrin A, Argyrin B, Argyrin C, Argyrin D, Argyrin E, Argyrin F, Argyrin G, and Argyrin H. Synthetic derivatives of Argyrin contain different substituents as R1, R2, R3, and R4 to common structure I.

The synthetic pathway enzymes catalyzing the synthesis of at least one Argyrin comprising the core structure I are encoded by nucleic acid sequences of the invention, containing the structural genes for the synthetic pathway enzymes.

Argyrins share the common core structure I:

(I)

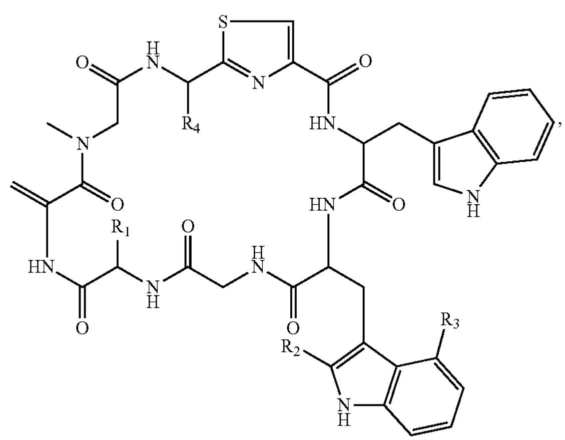

wherein substituents to R1, R2, R3, and R4 can vary, giving e.g. rise to natural derivatives designated Argyrins A-H. Generally, R1 can be selected from an alkyl group, preferably methyl and ethyl, R2 preferably is hydrogen or methyl, R3 preferably is hydrogen or methoxy, and R4 preferably is selected from hydrogen, methyl and hydroxymethyl, as described in Vollbrecht et al. (Journal of Antibiotics 8, 715-721 (2002)) for Argyrins obtained from *Archangium gephyra*. In dependence on the pattern of substitution, natural Argyrins are designated as follows:

Argyrin A $R_1{=}CH_3$; $R_2{=}H$; $R_3{=}OCH_3$; $R_4{=}CH_3$
Argyrin B $R_1{=}C_2H_5$; $R_2{=}H$; $R_3{=}OCH_3$; $R_4{=}CH_3$
Argyrin C $R_1{=}CH_3$; $R_2{=}CH_3$; $R_3{=}OCH_3$; $R_4{=}CH_3$
Argyrin D $R_1{=}C_2H_5$; $R_2{=}CH_3$; $R_3{=}OCH_3$; $R_4{=}CH_3$
Argyrin E $R_1{=}CH_3$; $R_2{=}H$; $R_3{=}H$; $R_4{=}CH_3$
Argyrin F $R_1{=}CH_3$; $R_2{=}H$; $R_3{=}OCH_3$; $R_4{=}CH_2OH$
Argyrin G $R_1{=}C_2H_5$; $R_2{=}H$; $R_3{=}OCH_3$; $R_4{=}CH_2OH$
Argyrin H $R_1{=}CH_3$; $R_2{=}H$; $R_3{=}OCH_3$; $R_4{=}H$ To-date, Argyrins are obtained from the natural producer organism *Archangium gephyra*, e.g. as a mixture of one or more of the above mentioned Argyrins, collectively referred to as Argyrins A-H, e.g. by isolation from the fermentation broth, and purification by standard methods, e.g. using partition and chromatography.

The use of the original producer strain in production only allows to influence the production rate of Argyrins or the predominant synthesis of one specific Argyrin by altering culture conditions.

U.S. Pat. No. 6,833,447 describes a nucleic acid sequence which encodes a nitrite reductase.

Sasse et al. in The Journal of Antibiotics 543-551 (2002) describe the production of the cell inhibiting compound termed Argyrin B in an *Archangium* strain. No nucleic acid sequence or amino acid sequences for synthetic pathway enzymes for the production of an Argyrin is given.

Rachid et al. in the Journal of Biotechnology 429-441 (2006) describe that *Cytobacter fuscus* is a producer of Argyrin. No nucleic acid sequence or amino acid sequences for synthetic pathway enzymes for the production of an Argyrin is given.

OBJECTS OF THE INVENTION

In view of the limited influence on the production of Argyrin in production methods using cultivation of a natural producer organism, it is an object of the present invention to provide for an alternative production method, and to provide the basis for manipulating the synthetic pathway for the production of Argyrins in micro-organisms, including producer strains and non-producer strains.

GENERAL DESCRIPTION OF THE INVENTION

The invention achieves the above-mentioned objects by providing the amino acid sequences comprised in or constituting the synthetic pathway enzymes participating in the production of Argyrins, as well as the nucleic acid sequences encoding the synthetic pathway enzymes participating in the production of Argyrins, as well as genetically manipulated micro-organisms containing nucleic acid sequences encoding the synthetic pathway enzymes for the production of Argyrins, the use of nucleic acid sequences hybridizing to the nucleic acid sequences encoding synthetic pathway enzymes participating in the production of Argyrins, e.g. for inserting one or more of these coding sequences, mutating in a targeted manner one or more of these coding nucleic acid sequences, in a wild type producer micro-organism or in a heterologous micro-organism, for production of at least one Argyrin. The invention also comprises nucleic acid sequences having a homology of at least 90%, preferably of at least 95%, more preferably of at least 99% to the coding nucleic acid sequences and encoding synthetic pathway enzymes with a catalytic activity essentially corresponding to the catalytic activity of the coding sequences given below, or which have a nucleotide sequence reverse complementary to the coding sequences given below.

The terminology of the invention includes proteins, peptides, and enzymes in respect of catalytically active proteins for amino acid sequences, as well as oligonucleotides, e.g. DNA and/or RNA, also referred to as coding sequences or genes, for nucleic acid sequences, respectively, as equivalent terms. Unless indicated otherwise, nucleic acid sequences are given from 5' to 3', and amino acid sequences are given from N-terminus to C-terminus. Accordingly, in one embodiment of the invention, a micro-organism is provided, which is genetically manipulated to contain nucleic acid sequences encoding synthetic pathway enzymes for the production of Argyrins, and a method for production of the Argyrins comprising the step of cultivating the genetically manipulated micro-organism. Preferably, the genetically manipulated heterologous micro-organism contains one or more expression cassettes containing the nucleic acid sequences encoding synthetic pathway enzymes for the production of Argyrins, which expression cassettes can be monocistronic or polycistronic.

In a second embodiment, the present invention provides the use of the nucleic acid sequences encoding synthetic pathway enzymes for the production of Argyrins for targeted mutation of these nucleic acid sequences encoding the synthetic pathway enzymes within natural producer strains of Argyrins, e.g. for site directed mutagenesis or for example for inserting one or more additional copies of the least one coding sequence within a monocistronic or polycistronic expression cassette, for altering the amino acid sequence encoded by the nucleic acid sequences of the invention, e.g. for changing the enzymatic activity of the synthetic pathway enzymes, or for inactivating one or more coding sequences encoding a synthetic pathway enzyme. The targeted inactivation of at least one coding sequence results in the change of the synthetic products, e.g. for directing Argyrin synthesis to the preferred production of one or more of Argyrins A to H. Generally, mutations, e.g. insertions, deletions and base exchanges of coding sequences encoding the Argyrins' synthetic pathway enzymes include the targeted mutation of the coding sequence, i.e. a mutation of the translated nucleic acid sections, as well as targeted mutation of the regulatory nucleic acid sections, e.g. of promoters and/or terminators. Mutations preferably cause for example the inactivation, alteration or increase of the catalytic activity of one or more enzymes, resulting in a change of the synthesis of Argyrins, e.g. in an increased Argyrin production or in the production of a different compound of Argyrins A to H when compared to the non-mutated strain.

In the alternative to or in addition to use of the synthetic pathway enzymes as expression products in genetically manipulated micro-organisms, the synthetic pathway enzymes can be expressed from the respective coding sequences and used for synthesis of Argyrins, e.g. in a production process for Argyrins using the synthetic pathway enzymes in a cell-free reaction composition, e.g. in solution or as immobilized enzymes, e.g. bound to the surface of a carrier. Accordingly, the invention provides the use of the amino acid sequences constituting at least one of the synthetic pathway enzymes for the cell-bound and/or cell-free conversion reaction of chemical compounds, e.g. of an Argyrin precursor compound, to an another precursor compound of Argyrin or at least one of the Argyrins.

Further, the invention also relates to the nucleic acid sequences encoding the synthetic pathway enzymes having activity to catalyse the synthesis of at least one Argyrin, the nucleic acid sequences being in substantially purified form, optionally contained in a synthetic nucleic acid construct suitable for genetic manipulation of at least one micro-organism.

DETAILED DESCRIPTION OF THE INVENTION

Figure 2:
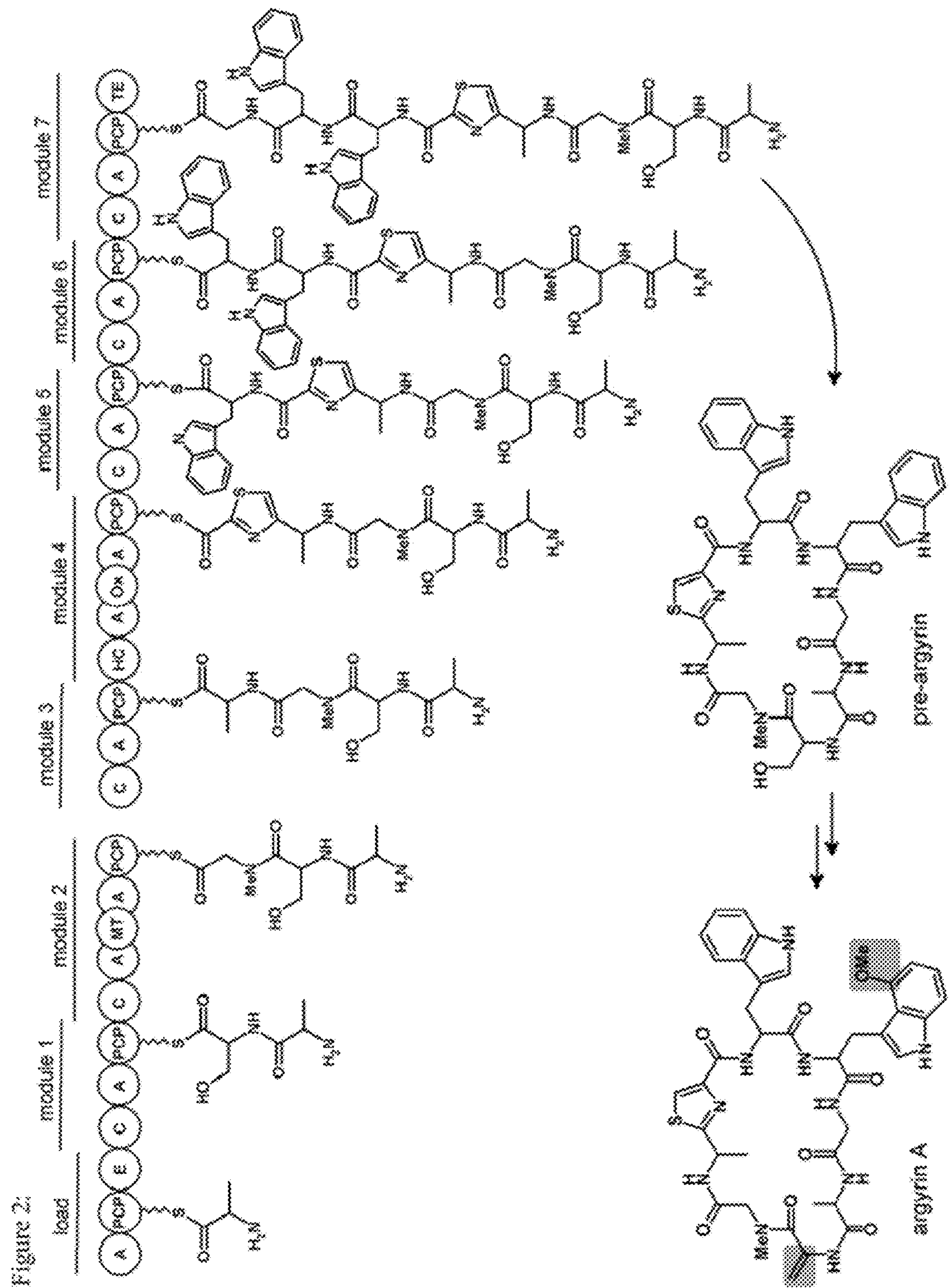
Figure 3:
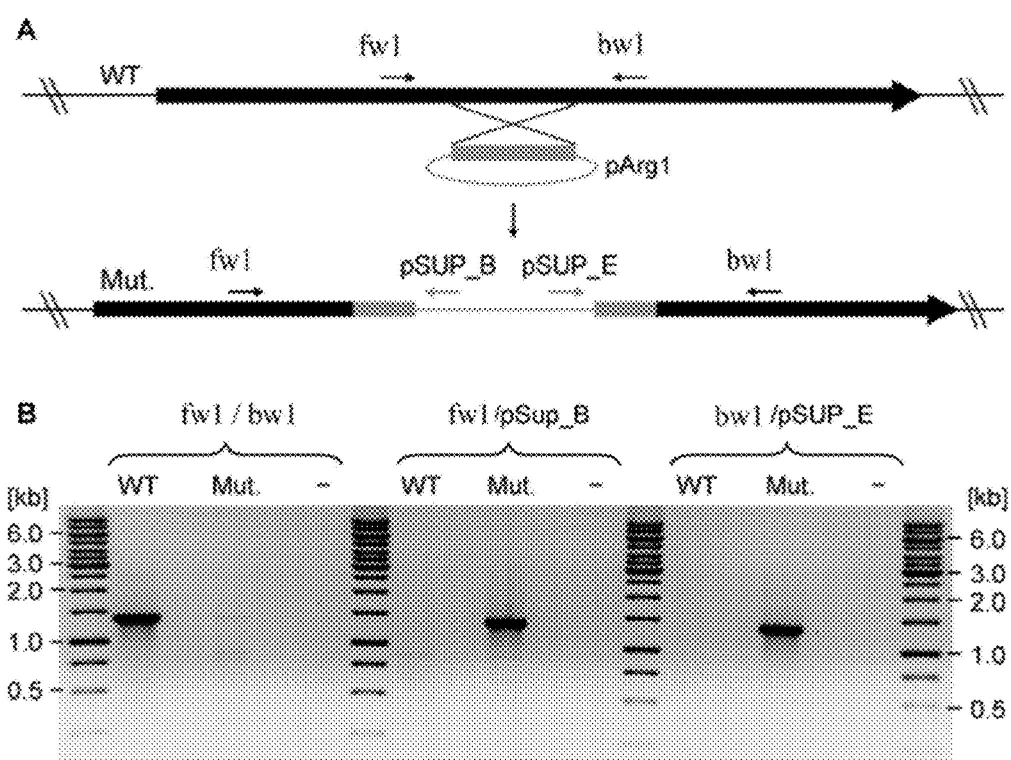
Figure 4:
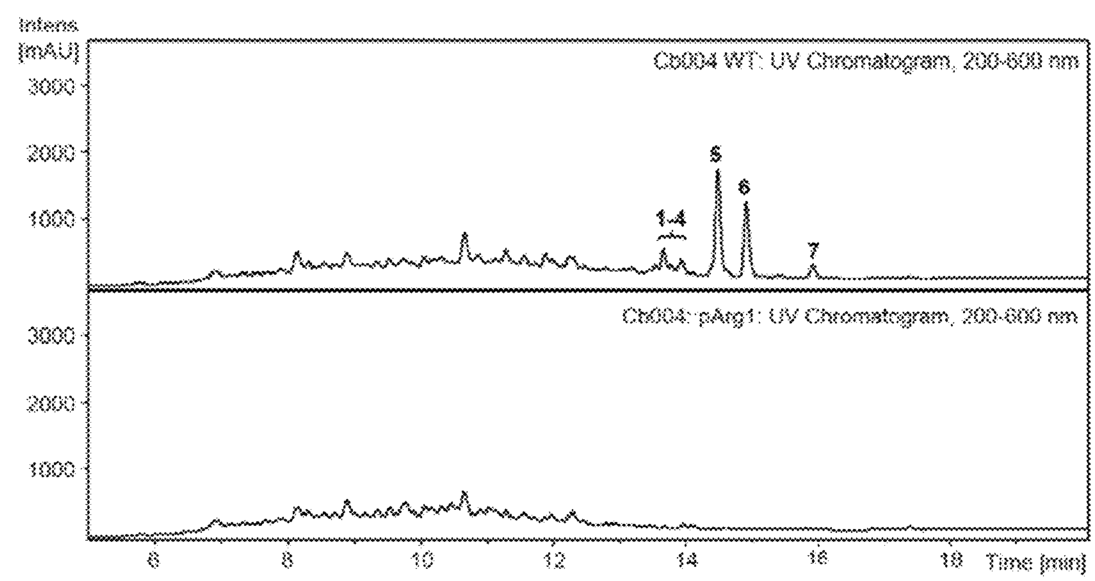

The invention is described in further detail by way of examples and with reference to the figures, wherein FIG. 1 schematically shows the arrangement of nucleic acid sequences encoding catalytically active amino acid sequences participating in the synthetic pathway of Argyrins, FIG. 2 schematically shows the synthetic steps catalysed by amino acid sequences, i.e. enzymes translated from nucleic acids of FIG. 1, FIG. 3 A shows a schematic representation of the targeted mutation of genes encoding synthetic pathway enzymes, FIG. 3 B shows a gel electrophoresis of PCR products confirming the mutation achieved according to FIG. 3 A, and FIG. 4 shows chromatogramms of HPLC of Argyrins synthesized, namely in A) by the non-mutated wild-type strain, and B) by a mutant obtained according to FIG. 3 A.

The invention provides coding sequences, the translation products of which are synthetic pathway enzymes participating in the production of Argyrins, which coding sequences are contained in SEQ ID NO: 1.

FIG. 1 gives a schematic overview of the arrangement of coding sequences which are contained in a wild-type Argyrin producer isolate that was identified as *Cystobacter* sp., termed strain SB-Cb004. Each nucleic acid sequence constituting an orf and encoding a catalytically active protein is indicated as an arrow, the arrow head designating the 3"-end.

From an analysis of catalytic domains encoded by the orf5 identified, it is concluded that the genes designated arg2 and arg3 (black arrows) comprise catalytically active domains for synthesis of pre-Argyrin from amino acids, in co-operation with a radical SAM-domain protein encoded by arg1. Accordingly, genes arg2 and arg3, preferably in combination with arg3, encode the core enzymes for synthesis of pre-Argyrin. Adjacent the genes arg1, arg2, and arg3, there are located genes orf1, orf2, orf3, orf4, orf5, orf6, orf7, orf8, orf9, orf10, orf11, orf12, orf13, and orf14, (orfs1-14) which in FIG. 1 are designated with their numbers only. Orfs1-14 encode enzymes having catalytic activities catalysing the synthesis of at least one of Argyrins A-H, e.g. from pre-Argyrin or another one of Argyrins A-H as a precursor. The following table gives the genes identified, which participate in the production of the least one Argyrin.

TABLE

Genes encoding amino acid sequences participating in the synthetic pathway of Argyrins and proposed catalytic activity of the encoded amino acid sequences

| gene | | | encoded protein | | |
|---|---|---|---|---|---|
| name | localization in Seq.-ID No. 1 (nt number) | GC [%] | size [aa] | amino acid sequence | proposed function (domain arrangement) |
| orf1 | 1608-4 | 66.3 | 534 | | ABC transporter |
| orf2 | 3615-1687 | 69.4 | 642 | | ABC transporter |

TABLE-continued

Genes encoding amino acid sequences participating in the synthetic pathway of Argyrins and proposed catalytic activity of the encoded amino acid sequences

| gene | | | encoded protein | | |
|---|---|---|---|---|---|
| name | localization in Seq.-ID No. 1 (nt number) | GC [%] | size [aa] | amino acid sequence | proposed function (domain arrangement) |
| orf3 | 5139-3661 | 71.1 | 492 | | ATP-dependent RNA helicase |
| orf4 | 7388-5274 | 64.3 | 704 | | elongation factor G |
| orf5 | 7710-8048 | 72.6 | 112 | | |
| orf6 | 8870-8043 | 71.7 | 275 | | pseudouridine synthase |
| orf7 | 9293-10282 | 69.2 | 329 | | |
| orf8 | 11057-10320 | 72.1 | 245 | | RNA methyltransferase |
| arg1 | 11545-13593 (Seq.-ID No. 2) | 62.6 | 682 | SEQ ID NO: 7 | radical SAM domain protein |
| arg2 | 13706-24322 (Seq.-ID No. 3) | 64.8 | 3538 | SEQ ID NO: 8 | NRPS loading module and modules 1-2 (A-PCP-E-C-A-PCP-C-A`-MT-A``-PCP) |
| arg3 | 24361-42201 (Seq.-ID No. 4) | 66.0 | 5946 | SEQ ID NO: 9 | NRPS modules 3-7 (C-A-PCP-HC-A`-Ox-A``-PCP-C-A-PCP-C-A-PCP-C-A-PCP-TE) |
| arg4 | 42239-43249 (Seq.-ID No. 5) | 63.7 | 336 | SEQ ID NO: 10 | O-methyl transferase |
| arg5 | 43309-44460 (Seq.-ID No. 6) | 63.5 | 383 | SEQ ID NO: 11 | tryptophane 2,3-dioxygenase |
| orf9 | 45620-44706 | 62.7 | 304 | | |
| orf10 | 46507-45617 | 59.8 | 296 | | |
| orf11 | 47244-46504 | 85.9 | 246 | | N6-DNA methylase |
| orf12 | 47547-47975 | 67.8 | 142 | | |
| orf13 | 48288-49268 | 69.0 | 326 | | |
| orf14 | 49483-55209 | 69.7 | 1908 | | large extracellular alpha-helical protein |
| orf15 | 55212-55565 | 61.9 | 117 | | |

nt = nucleotide;
orf = open reading frame;
aa = amino acid

From the above coding sequences, arg2 and arg3 are considered as essential for the production of Argyrins, e.g. for synthesis of pre-Argyrin, preferably in connection with one or both of arg4 and arg5, more preferably further in addition with a radical SAM domain protein, preferably encoded by arg1.

The nucleic acid sequences for all genes are contained in SEQ ID NO: 1, wherein the genes are located from 5' to 3' and from 3' to 5', as indicated in the sequence listing. Further, genes arg1 to arg5 are given in 5' to 3', as well as their translation products, i.e. the amino acid sequences of the enzymes Arg1 to Arg5.

Accordingly, the present invention in one aspect relates to isolated nucleic acid sequences encoding synthetic pathway enzymes for the production of the least one Argyrins, which nucleic acid sequences comprise at least coding sequences for Argyrin synthetic pathway enzymes, including or consisting of genes encoding enzymes Arg2 (SEQ ID NO: 8) and arg3 (SEQ ID NO: 9), preferably for enzyme Arg1 (SEQ ID NO: 7), and more preferably nucleic acids coding for at least one of enzymes encoded by at least one of orfs1-14, a heterologous micro-organism containing nucleic acid sequences encoding at least one Argyrin synthetic pathway enzyme, e.g. introduced into a micro-organism by genetic manipulation, preferably integrated into the genome of a heterologous host micro-organism or integrated by genetic manipulation into the genome of an Argyrin producer micro-organism, nucleic acid molecules having a sequence complementary to at least one nucleic acid sequence encoding a synthetic pathway enzyme participating in the production of at least one Argyrin, a nucleic acid molecule capable of hybridizing, especially under stringent conditions, to a nucleic acid molecule encoding at least one Argyrin synthetic pathway enzyme, especially to the sequence of arg2 and arg3, preferably in combination with arg1, the translation products of which nucleic acid sequences are synthetic pathway enzymes for the production of Argyrins, and/or which translation products have the activity of at least one synthetic pathway enzyme in the production of Argyrins.

Further, the invention relates to micro-organisms containing nucleic acid sequences encoding at least one synthetic pathway enzyme for the production of at least one Argyrin, preferably nucleic acid sequences comprising arg1, arg2, arg3, arg4, more preferably additionally including arg5. Preferably, the micro-organisms are genetically manipulated to contain these nucleic acid sequences for use in the production of Argyrins, preferably for use in the production of pre-Argyrin.

FIG. 2 depicts the synthesis of pre-Argyrin by synthetic pathway enzymes of the invention, wherein the following activities are identifiable in domains of enzymes: A=adenylation domain, PCP=peptidyl carrier protein domain, C=condensation domain, HC=heterocyclization domain, E=epimerization domain, MT=methyl transferase domain, Ox=oxidation domain, and TE=thioesterase domain. However, the arrangement of domains shown in FIG. 2 is arbitrary and does not necessarily reflect their arrangement in the enzyme.

The core biosynthetic genes are encoded by arg2 and arg3, which are preferably arranged in one common transcriptional unit with arg1, which encodes a radical SAM protein, and more preferably in combination with arg4 and arg5 which encode a O-methyl transferase and a tryptophane 2,3-dioxygenase. In accordance with the natural arrangement of arg2 and arg3 in one transcriptional unit, preferably in combination with arg1, it is preferred that in the nucleic acids of the invention, the coding sequences for arg2 and arg3 are arranged in one transcriptional unit, preferably in combination with arg1 within the same one transcriptional unit. Genes arg4 and arg5 can be contained in the same or a different transcriptional unit.

In detail, FIG. 2 shows the assignment of catalytic domains as derived from the sequence of arg2, comprising the load-module, module 1 and module 2, as well as of arg3 comprising module 3, module 4, module 5, module 6, and module 7, which in co-operation catalyse step-wise synthesis of pre-Argyrin. Initially, the PCP-domain of the load-module, the coding sequence of which is contained in arg2, is charged with the initial alanine by the A domain. The synthesis of the Argyrin core structure I is obtainable by the combination of translation products of coding sequences comprising, preferably consisting of arg2, arg3, arg4, preferably including arg5, more preferably further including arg1.

As shown on the example of derivatisation of pre-Argyrine to Argyrin A, the derivatisation, i.e. introduction of substituents R1, R2, R3 and/or R4 to the Argyrin of core structure I is catalysed e.g. by the translation products of one or more of orfs1-15. Analyses of the enzymes show that the translation product of arg1 (Arg1) catalyses the methylation of Argyrin A to form Argyrin B, that the translation product of arg5 (Arg5) catalyses the hydroxylation of the tryptophane ring, and that the translation product of arg4 (Arg4) catalyses the methylation of the OH-group of the tryptophane ring that was introduced by Arg5.

The catalytic activities of translation products of each of orfs1-15 and of arg1, arg4 and arg5 can be identified according to standard methods, e.g. by comparison of their amino acid sequences to known proteins, or preferably by analysis of reaction products generated in the presence of the translation products using defined substrates as precursor compounds for enzymatic catalysis. In the alternative, the catalytic activities of the translation products can be determined by generating mutant micro-organisms containing the genes encoding the enzymes for Argyrine synthesis, which micro-organisms are genetically manipulated to contain a non-functional copy of one or more of these genes replacing the functional gene copies, and analysing the resultant Argyrins synthesized by the micro-organism. For generating one or more non-functional genes, the respective gene copies in a wild-type Argyrin producer strain can be destroyed, e.g. by insertional site-directed mutagenesis as shown below, or a homologous or heterologous non-producer strain can be provided with the genes encoding the synthetic pathway enzymes but lacking one or more of these genes. Analysis of the resultant Argyrin production can be done by standard methods, e.g. by high-pressure liquid chromatography (HPLC), preferably coupled with a mass-spectrometer.

EXAMPLE 1

Site-Directed Mutagenesis of an Argyrin Producer and Analysis of Changes in Synthesis of Argyrins On the basis of nucleic acid sequences of genes encoding synthetic pathway enzymes for Argyrin synthesis, a first oligonucleotide fw1 (5'-CTCGATATCCCAGCGCAAGAGCT ATCG-3', SEQ ID NO: 12; the EcoRI restriction site is underlined), and a second oligonucleotide bw1 (5'-CTC GGATCCGGTCGGGAACCATGTACC-3', SEQ ID NO: 13, including a BamHI restriction site, underlined) were constructed and used for amplification of a 1.1 kbp DNA fragment of arg3 by PCR (3 min at 95° C., 30 cycles of 30 s at 95° C., 50 s at 56° C., 90 s at 72° C.). The fragment was isolated and ligated into the EcoRI and BamHI restriction sites of an *E. coli-Cystobacter* shuttle vector pSUP carrying transposon sections and a kanamycin resistance gene, giving vector pArg, schematically shown in FIG. 3A. For conjugational transfer of pArg1, methylation deficient *E. coli* SCS110 harbouring pArg1 and helper plasmid pRK600 for conjugation was grown in LB medium with kanamycin and chloramphenicol (pRK600) to 0.6 $OD_{600}$. *E. coli* cells were washed and combined with cells of *Cystobacter* cultured in 1 mL M medium under shaking at 30° C. for 30 min, collected and resuspended in M medium and plated on M agar containing 100 μg/mL kanamycin and 120 μg/mL tobramycin. Incubation was at 30° C. until transconjugants appeared, usually after about 3 to 4 days.

Upon conjugational transfer of the vector pArg1 into wild-type isolate Argyrin producer *Cystobacter* sp., integration of the vector into chromosomal DNA was confirmed by PCR on total DNA isolated from different transformants. An electrophoresis gel of PCR amplificates is shown in FIG. 3B, namely for total DNA isolated from the wild-type (WT), transformant (Mut.), and negative control (*E. coli*) using primers fw1 and bw1 (indicated as fw1/bw1), primers fw1 and a reverse primer (pSup_B) specific for a section of the original shuttle vector, and primers bw1 and a reverse primer specific for a section of the original shuttle vector (pSup_E).

The analysis by gel electrophoresis shown in FIG. 3B demonstrates that the vector was integrated in a site-directed manner within the genomic arg3.

For analysis of the effect of the inactivation of arg3 by insertional site-directed mutagenesis using the nucleotide sequences of the invention, the production of Argyrins was analysed for the wild-type and for the mutated *Cystobacter* sp. by HPLC. Production of Argyrins was by incubation in M medium in shake flasks in the presence of 2% adsorber resin XAD for 4 days at 30° C. Cells and adsorber resin were collected and extracted with methanol, the extract was concentrated 1:50 and analysed by HPLC-MS (reverse phase 125×2 mm, 3 μm particle size C18 column Nucleodur, Macherey-Nagel, using a 8×3 mm, 5 μm pre-column C18 with diode array detection at 200-600 nm, followed by a HCTplus ion trap mass spectrometer, Bruker, positive and negative ionization detection at 100-1100 amu). HPLC was with a liner gradient 5% B (0.1% formic acid in water) at 2 min to 95% B in A (0.1% formic acid in acetonitrile) by 4 min at 0.4 mL/min. As shown in FIG. 4 A, the wild-type culture produced Argyrin A (peak 5), Argyrin B (peak 6), Argyrin D (peak 7), and Argyrins E to H (peaks 1-4, respectively). In contrast to the wild-type, the mutated strain did not produce any of the Argyrins A, B, D-H, demonstrating the effect of this site-directed mutagenesis by the example of disruption of one gene in a site-directed manner by insertional mutagenesis, and the central role of the enzyme encoded by arg3 for Argyrin synthesis.

EXAMPLE 2

Production of Argyrin Using an Original Non-Producer Strain by Expression of Genes Encoding the Pathway Enzymes for Argyrin Synthesis For demonstrating the synthesis of Argyrins from the genes encoding the synthetic pathway enzymes, a non-producer micro-organism was provided with the gene cluster comprising the complete synthetic pathway enzymes for Argyrin synthesis including arg1 to arg5 and, optionally, orfs1-15. For transfer of the genes, Seq.-ID No. 1, which contains all of the genes, was transferred into the host organism of the genus myxobacteria, e.g. *Myxococcus xanthus* (described in Perlova et al., AEM 2006, 72, 7485-7494) by the method according to Pradella et al., *Arch. Microbiol.* 178, 484-492 (2002) using conjugational transfer from *E. coli*, preferably according to the genetic modification system using electroporation of myxobacteria in the presence of a carbohydrate as described in EP 1 619 241 A1.

Generally, production of Argyrins by heterologous expression of the nucleic acid sequences in a host micro-organism was monitored by analytical methods as described in Vollbrecht et al. (loc. cit.), preferably by chromatographic purification of an extract from the fermentation broth, with MS coupling and/or NMR of purified fractions. Using these analyses, the Argyrin derivates synthesized by the micro-organism were identified including changes in product spectra, e.g. indicating preferred or reduced synthesis of a specific Argyrin derivate in the heterologous expression host or in a natural producer micro-organism following genetic manipulation of the synthetic pathway genes.

Alternatively, using the method as e.g. described in Gross et al. (Chemistry and Biology 13, 1253-1264 (2006)), *Pseudomonas* spec. could be used for heterologous expression of the synthetic pathway enzymes of the invention, yielding synthesis of Argyrins. Further, the synthetic pathway enzymes could be expressed in *Pseudomonas putida* by adapting the method of Wenzel et al. (Chemistry and Biology 12, 349-356 (2005)), resulting in Argyrin synthesis.

Cultivation of micro-organisms and analysis of Argyrins was according to Example 1, optionally using SM medium containing 5 g/L asparagine, 0.5 g/L $MgSO_4.7H_2O$, 100 mM HEPES, 10 mg/L Fe-EDTA, 0.5 g/L $CaCl_2$, 0.06 g/L $K_2HPO_4$, 10 g/L maltose, pH 7.2, instead of M medium (1.0% soy tryptone, 1.0% maltose, 0.1% $CaCl_2$, 0.1% $MgSO_4.7H_2O$, 50 mM HEPES and 8 mg/L Na—Fe-EDTA, adjusted to pH 7.2).

The wild-type strain without genetic modification did not produce any detectable amount of Argyrins, whereas the transformant produced pre-Argyrin, Argyrin A and Argyrin B, with detectable levels of Argyrins D-H.

The product spectrum of Argyrins could be altered by transformation with a nucleic acid containing at least arg1, arg2 and arg3 with one or more of arg4, arg5, and of orf 1 to orf 15.

The invention claimed is:

1. An isolated nucleic acid molecule, encoding an amino acid sequence having enzymatic activity of a synthetic pathway enzyme for the production of Argyrins, wherein the amino acid sequence comprises the amino acid sequences of SEQ ID NO: 8 (Arg2) and SEQ ID NO: 9 (Arg3).

2. The isolated nucleic acid molecule of claim 1, wherein the nucleic acid molecule comprises the nucleotide sequence of SEQ ID NO: 3 that encodes Arg2 and comprises the nucleotide sequence of SEQ ID NO: 4 that encodes Arg3.

3. A genetically manipulated microorganism that comprises a nucleic acid molecule encoding an amino acid sequence having enzymatic activity of a synthetic pathway enzyme for the production of Argyrins, wherein the amino acid sequence is Arg2 (SEQ ID NO: 8) and Arg3 (SEQ ID NO: 9).

4. The genetically manipulated microorganism of claim 3, wherein the microorganism is genetically manipulated to comprise SEQ ID NO:3, that encodes Arg2 and SEQ ID NO:4 that encodes Arg3.

5. A process for producing Argyrins comprising cultivating a genetically manipulated microorganism which is genetically manipulated to comprise a nucleic acid molecule encoding an amino acid sequence having enzymatic activity of a synthetic pathway enzyme for the production of Argyrins, wherein the encoded amino acid sequence comprises the amino acid sequences of SEQ ID NO: 8 and SEQ ID NO: 9.

6. The process of claim 5, wherein the genetically manipulated microorganism is genetically manipulated to comprise a nucleic acid molecule comprising the nucleotide sequence of SEQ ID NO: 3 that encodes Arg2 and the nucleotide sequence of SEQ ID NO: 4 that encodes Arg3.

* * * * *